(12) United States Patent
Tanaka et al.

(10) Patent No.: US 8,474,449 B2
(45) Date of Patent: *Jul. 2, 2013

(54) VARIABLE LENGTH PNEUMOSTOMA MANAGEMENT SYSTEM FOR TREATMENT OF CHRONIC OBSTRUCTIVE PULMONARY DISEASE

(75) Inventors: Don Tanaka, Saratoga, CA (US); Joshua P. Wiesman, Boston, MA (US); David C. Plough, Portola Valley, CA (US)

(73) Assignee: Portaero, Inc., Cupertino, CA (US)

( * ) Notice: Subject to any disclaimer, the term of this patent is extended or adjusted under 35 U.S.C. 154(b) by 1171 days.

This patent is subject to a terminal disclaimer.

(21) Appl. No.: 12/388,469

(22) Filed: Feb. 18, 2009

(65) Prior Publication Data
US 2009/0205650 A1 Aug. 20, 2009

Related U.S. Application Data

(60) Provisional application No. 61/029,830, filed on Feb. 19, 2008, provisional application No. 61/062,877, filed on Feb. 29, 2008, provisional application No. 61/038,371, filed on Mar. 20, 2008, provisional application No. 61/082,892, filed on Jul. 23, 2008, provisional application No. 61/083,573, filed on Jul. 25, 2008, provisional application No. 61/084,559, filed on Jul. 29, 2008, provisional application No. 61/088,118, filed on Aug. 12, 2008, provisional application No. 61/143,298, filed on Jan. 8, 2009, provisional application No. 61/151,581, filed on Feb. 11, 2009.

(51) Int. Cl.
*A61M 16/00* (2006.01)
*A61M 5/00* (2006.01)

(52) U.S. Cl.
USPC ............ 128/200.24; 128/202.27; 128/205.12; 128/205.19; 128/205.24; 604/45; 604/174; 604/175; 604/180; 604/304; 604/307; 604/386

(58) Field of Classification Search
USPC ............ 128/200.24, 200.25, 202.27, 205.12, 128/205.19, 205.24; 604/45, 174, 175, 180, 604/304, 307, 386
See application file for complete search history.

(56) References Cited

U.S. PATENT DOCUMENTS

| | | | |
|---|---|---|---|
| 733,152 | A | 7/1903 | Chisholm |
| 953,922 | A | 4/1910 | Rogers |

(Continued)

FOREIGN PATENT DOCUMENTS

| | | |
|---|---|---|
| EP | 0260543 A1 | 3/1988 |
| EP | 1358904 | 5/2003 |

(Continued)

OTHER PUBLICATIONS

Rendina et al., "Feasibility and safety of the airway bypass procedure for patients with emphysema", The Journal of Thoracic and Cardiovascular Surgery 2003; 125: 1294-1299.

(Continued)

*Primary Examiner* — Clinton T Ostrup
(74) *Attorney, Agent, or Firm* — Fliesler Meyer LLP

(57) ABSTRACT

A flexible pneumostoma management device maintains the patency of a pneumostoma while controlling the flow of material through the pneumostoma. The pneumostoma management device includes flange attaches to the chest of the patient to secure the device in position. The pneumostoma management device also includes a tube which enters the pneumostoma to allow gases to escape the lung. The length of the tube is selected to match the dimensions of the pneumostoma of a patient. In order to manufacture devices having different tube lengths, the tube is formed at a longer length than required, cut to size and tipped. The tube may be formed by molding or extrusion.

19 Claims, 24 Drawing Sheets

U.S. PATENT DOCUMENTS

| | | |
|---|---|---|
| 2,206,687 A | 7/1940 | Bloomheart |
| 2,599,521 A * | 6/1952 | Berman .................. 128/207.14 |
| 2,867,213 A | 1/1959 | Thomas, Jr. |
| 2,873,742 A | 2/1959 | Shelden |
| 2,991,787 A | 7/1961 | Shelden et al. |
| 3,253,594 A | 5/1966 | Matthews et al. |
| 3,384,087 A | 5/1968 | Brummelkamp |
| 3,463,159 A | 8/1969 | Heimlich |
| 3,511,243 A | 5/1970 | Toy |
| 3,556,103 A | 1/1971 | Calhoun et al. |
| 3,638,649 A | 2/1972 | Ersek |
| 3,682,166 A | 8/1972 | Jacobs |
| 3,688,773 A | 9/1972 | Weiss |
| 3,707,146 A | 12/1972 | Cook et al. |
| 3,766,920 A | 10/1973 | Greene |
| 3,777,757 A | 12/1973 | Gray et al. |
| 3,788,326 A | 1/1974 | Jacobs |
| 3,817,250 A | 6/1974 | Weiss et al. |
| 3,908,704 A | 9/1975 | Clement et al. |
| 3,916,903 A | 11/1975 | Pozzi |
| 4,153,058 A | 5/1979 | Nehme |
| 4,291,694 A | 9/1981 | Chai |
| 4,439,189 A | 3/1984 | Sargeant et al. |
| 4,465,062 A | 8/1984 | Versaggi et al. |
| 4,502,482 A | 3/1985 | DeLuccia et al. |
| 4,583,977 A | 4/1986 | Shishov et al. |
| 4,664,660 A | 5/1987 | Goldberg et al. |
| 4,717,385 A * | 1/1988 | Cameron et al. .............. 604/174 |
| 4,799,494 A | 1/1989 | Wang |
| 4,813,929 A | 3/1989 | Semrad |
| 4,826,495 A | 5/1989 | Petersen |
| 4,828,553 A | 5/1989 | Nielsen |
| 4,869,717 A | 9/1989 | Adair |
| 4,872,869 A | 10/1989 | Johns |
| 4,889,534 A | 12/1989 | Mohiuddin et al. |
| 4,931,045 A | 6/1990 | Steer |
| 4,944,724 A | 7/1990 | Goldberg et al. |
| 4,959,054 A | 9/1990 | Heimke et al. |
| 4,976,688 A | 12/1990 | Rosenblum |
| 5,004,456 A | 4/1991 | Botterbusch et al. |
| 5,060,645 A | 10/1991 | Russell |
| 5,078,689 A | 1/1992 | Keller |
| 5,137,509 A | 8/1992 | Freitas |
| 5,139,485 A | 8/1992 | Smith et al. |
| 5,207,652 A * | 5/1993 | Kay ................. 604/180 |
| 5,218,957 A | 6/1993 | Strickland |
| 5,230,332 A | 7/1993 | Strickland |
| 5,230,350 A | 7/1993 | Fentress |
| 5,261,708 A | 11/1993 | Steer |
| 5,263,939 A | 11/1993 | Wortrich |
| 5,312,331 A | 5/1994 | Knoepfler |
| 5,315,992 A | 5/1994 | Dalton |
| 5,336,206 A | 8/1994 | Shichman |
| 5,354,283 A | 10/1994 | Bark et al. |
| 5,356,386 A | 10/1994 | Goldberg et al. |
| 5,366,478 A | 11/1994 | Brinkerhoff et al. |
| 5,370,625 A | 12/1994 | Shichman |
| 5,376,376 A | 12/1994 | Li |
| 5,389,077 A | 2/1995 | Melinyshyn et al. |
| 5,401,262 A | 3/1995 | Karwoski et al. |
| 5,403,264 A | 4/1995 | Wohlers et al. |
| 5,431,633 A | 7/1995 | Fury |
| 5,478,333 A | 12/1995 | Asherman, Jr. |
| 5,484,401 A | 1/1996 | Rodriguez et al. |
| 5,487,382 A * | 1/1996 | Bezicot .................... 128/207.14 |
| 5,496,297 A | 3/1996 | Olsen |
| 5,501,677 A | 3/1996 | Jensen |
| 5,501,678 A | 3/1996 | Olsen |
| 5,588,424 A | 12/1996 | Insler et al. |
| 5,616,131 A | 4/1997 | Sauer et al. |
| 5,660,175 A | 8/1997 | Dayal |
| 5,662,629 A | 9/1997 | Steer et al. |
| 5,728,066 A | 3/1998 | Daneshvar |
| 5,730,735 A | 3/1998 | Holmberg et al. |
| 5,738,661 A | 4/1998 | Larice |
| 5,807,341 A | 9/1998 | Heim |
| 5,830,200 A | 11/1998 | Steer et al. |
| 5,843,053 A | 12/1998 | Steer |
| 5,897,531 A | 4/1999 | Amirana |
| 5,931,821 A | 8/1999 | Weilbacher et al. |
| 5,954,636 A | 9/1999 | Schwartz et al. |
| 5,971,962 A | 10/1999 | Kojima et al. |
| 5,972,026 A | 10/1999 | Laufer et al. |
| 6,056,744 A | 5/2000 | Edwards |
| 6,059,816 A | 5/2000 | Moenning |
| 6,083,255 A | 7/2000 | Laufer et al. |
| 6,174,323 B1 | 1/2001 | Biggs et al. |
| 6,197,010 B1 | 3/2001 | Leise, Jr. et al. |
| 6,200,333 B1 | 3/2001 | Laufer |
| 6,258,100 B1 | 7/2001 | Alferness et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,287,290 B1 | 9/2001 | Perkins et al. |
| 6,293,930 B1 | 9/2001 | Brunsgaard et al. |
| 6,293,951 B1 | 9/2001 | Alferness et al. |
| 6,299,633 B1 | 10/2001 | Laufer |
| 6,322,536 B1 | 11/2001 | Rosengart et al. |
| 6,328,689 B1 | 12/2001 | Gonzalez et al. |
| 6,330,882 B1 | 12/2001 | French |
| 6,334,441 B1 | 1/2002 | Zowtiak et al. |
| 6,358,269 B1 | 3/2002 | Aye |
| 6,398,775 B1 | 6/2002 | Perkins et al. |
| 6,402,754 B1 | 6/2002 | Gonzalez |
| 6,411,852 B1 | 6/2002 | Danek et al. |
| 6,416,554 B1 | 7/2002 | Alferness et al. |
| 6,432,100 B1 | 8/2002 | Affeld |
| 6,443,156 B1 | 9/2002 | Niklason et al. |
| 6,468,292 B1 | 10/2002 | Mollenauer et al. |
| 6,485,407 B2 | 11/2002 | Alferness et al. |
| 6,488,673 B1 | 12/2002 | Laufer et al. |
| 6,491,706 B1 | 12/2002 | Alferness et al. |
| 6,514,290 B1 | 2/2003 | Loomas |
| 6,517,519 B1 | 2/2003 | Rosen et al. |
| 6,520,183 B2 | 2/2003 | Amar |
| 6,527,761 B1 | 3/2003 | Soltesz et al. |
| 6,550,475 B1 | 4/2003 | Oldfield |
| 6,569,121 B1 | 5/2003 | Purow et al. |
| 6,569,166 B2 | 5/2003 | Gonzalez |
| 6,585,639 B1 | 7/2003 | Kotmel et al. |
| 6,589,161 B2 | 7/2003 | Corcoran |
| 6,592,594 B2 | 7/2003 | Rimbaugh et al. |
| 6,599,311 B1 | 7/2003 | Biggs et al. |
| 6,609,521 B1 | 8/2003 | Belani et al. |
| 6,629,951 B2 | 10/2003 | Laufer et al. |
| 6,632,239 B2 | 10/2003 | Snyder et al. |
| 6,632,243 B1 | 10/2003 | Zadno-Azizi et al. |
| 6,634,360 B1 | 10/2003 | Flodin |
| 6,634,363 B1 | 10/2003 | Danek et al. |
| 6,638,253 B2 | 10/2003 | Breznock |
| 6,653,525 B2 | 11/2003 | Ingenito et al. |
| 6,659,961 B2 | 12/2003 | Robinson |
| 6,679,264 B1 | 1/2004 | Deem et al. |
| 6,682,506 B1 | 1/2004 | Navarro |
| 6,692,494 B1 | 2/2004 | Cooper et al. |
| 6,694,979 B2 | 2/2004 | Deem et al. |
| 6,695,791 B2 | 2/2004 | Gonzalez |
| 6,709,401 B2 | 3/2004 | Perkins et al. |
| 6,712,812 B2 | 3/2004 | Roschak et al. |
| 6,736,797 B1 | 5/2004 | Larsen et al. |
| 6,749,606 B2 | 6/2004 | Keast et al. |
| 6,770,063 B2 | 8/2004 | Goldberg et al. |
| 6,770,070 B1 | 8/2004 | Balbierz |
| 6,790,172 B2 | 9/2004 | Alferness et al. |
| 6,827,086 B2 | 12/2004 | Shuman |
| 6,837,906 B2 | 1/2005 | Ginn |
| 6,840,243 B2 | 1/2005 | Deem et al. |
| 6,843,767 B2 | 1/2005 | Corcoran et al. |
| 6,846,292 B2 | 1/2005 | Bakry |
| 6,849,061 B2 | 2/2005 | Wagner |
| 6,852,108 B2 | 2/2005 | Barry et al. |
| 6,860,847 B2 | 3/2005 | Alferness et al. |
| 6,878,141 B1 | 4/2005 | Perkins et al. |
| 6,886,558 B2 | 5/2005 | Tanaka |
| 6,901,927 B2 | 6/2005 | Deem et al. |
| 6,904,909 B2 | 6/2005 | Andreas et al. |
| 6,905,518 B2 | 6/2005 | Ginn |

| | | |
|---|---|---|
| 6,916,310 B2 | 7/2005 | Sommerich |
| 6,929,637 B2 | 8/2005 | Gonzalez et al. |
| 6,941,950 B2 | 9/2005 | Wilson et al. |
| 6,997,189 B2 | 2/2006 | Biggs et al. |
| 6,997,918 B2 | 2/2006 | Soltesz et al. |
| 7,011,094 B2 | 3/2006 | Rapacki et al. |
| 7,014,628 B2 | 3/2006 | Bousquet |
| 7,022,088 B2 | 4/2006 | Keast et al. |
| 7,033,387 B2 | 4/2006 | Zadno-Azizi et al. |
| 7,036,509 B2 | 5/2006 | Rapacki et al. |
| 7,086,398 B2 | 8/2006 | Tanaka |
| 7,100,616 B2 | 9/2006 | Springmeyer |
| 7,135,010 B2 | 11/2006 | Buckman et al. |
| 7,141,046 B2 | 11/2006 | Perkins et al. |
| 7,165,548 B2 | 1/2007 | Deem et al. |
| 7,172,581 B2 | 2/2007 | Ciok et al. |
| 7,175,644 B2 | 2/2007 | Cooper et al. |
| 7,182,772 B2 | 2/2007 | Alferness et al. |
| 7,186,259 B2 | 3/2007 | Perkins et al. |
| 7,192,420 B2 | 3/2007 | Whiteford |
| 7,195,016 B2 | 3/2007 | Loyd et al. |
| 7,195,017 B2 | 3/2007 | Tanaka |
| 7,207,946 B2 | 4/2007 | Sirokman |
| 7,232,414 B2 | 6/2007 | Gonzalez |
| 7,244,245 B2 | 7/2007 | Purow et al. |
| 7,252,086 B2 | 8/2007 | Tanaka |
| 7,377,278 B2 | 5/2008 | Tanaka |
| 7,398,782 B2 | 7/2008 | Tanaka |
| 7,406,963 B2 | 8/2008 | Chang et al. |
| 7,426,929 B2 | 9/2008 | Tanaka |
| 7,533,667 B2 | 5/2009 | Tanaka |
| 2001/0025132 A1 | 9/2001 | Alferness et al. |
| 2001/0041906 A1 | 11/2001 | Gonzalez |
| 2001/0041932 A1 | 11/2001 | Scholz et al. |
| 2002/0042564 A1 | 4/2002 | Cooper et al. |
| 2002/0062120 A1 | 5/2002 | Perkins et al. |
| 2002/0077593 A1 | 6/2002 | Perkins et al. |
| 2002/0087153 A1 | 7/2002 | Roschak et al. |
| 2002/0111619 A1 | 8/2002 | Keast et al. |
| 2002/0111620 A1 | 8/2002 | Cooper et al. |
| 2002/0112729 A1 | 8/2002 | DeVore et al. |
| 2002/0120177 A1 | 8/2002 | Borst et al. |
| 2002/0165618 A1 | 11/2002 | Ingenito et al. |
| 2002/0188171 A1 | 12/2002 | Alferness et al. |
| 2003/0013935 A1 | 1/2003 | Alferness et al. |
| 2003/0018344 A1 | 1/2003 | Kaji et al. |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0065339 A1 | 4/2003 | Snyder et al. |
| 2003/0069488 A1 | 4/2003 | Alferness et al. |
| 2003/0078469 A1 | 4/2003 | Corcoran |
| 2003/0083542 A1 | 5/2003 | Alferness et al. |
| 2003/0083671 A1 | 5/2003 | Rimbaugh et al. |
| 2003/0127090 A1 | 7/2003 | Gifford et al. |
| 2003/0130593 A1 | 7/2003 | Gonzalez |
| 2003/0149446 A1 | 8/2003 | Shuman |
| 2003/0154988 A1 | 8/2003 | DeVore et al. |
| 2003/0158515 A1 | 8/2003 | Gonzalez et al. |
| 2003/0163024 A1 | 8/2003 | Corcoran |
| 2003/0181356 A1 | 9/2003 | Ingenito |
| 2003/0181922 A1 | 9/2003 | Alferness |
| 2003/0183235 A1 | 10/2003 | Rimbaugh et al. |
| 2003/0186904 A1 | 10/2003 | Ruben et al. |
| 2003/0195385 A1 | 10/2003 | DeVore |
| 2003/0195511 A1 | 10/2003 | Barry |
| 2003/0212337 A1 | 11/2003 | Sirokman |
| 2003/0212412 A1 | 11/2003 | Dillard et al. |
| 2003/0216730 A1 | 11/2003 | Barry et al. |
| 2003/0216769 A1 | 11/2003 | Dillard et al. |
| 2003/0228344 A1 | 12/2003 | Fields et al. |
| 2003/0233073 A1* | 12/2003 | Purow et al. .................. 604/174 |
| 2003/0233099 A1 | 12/2003 | Danaek et al. |
| 2004/0010209 A1 | 1/2004 | Sirokman |
| 2004/0010289 A1 | 1/2004 | Biggs et al. |
| 2004/0016435 A1 | 1/2004 | Deem et al. |
| 2004/0024356 A1 | 2/2004 | Tanaka |
| 2004/0031494 A1 | 2/2004 | Danek et al. |
| 2004/0040555 A1 | 3/2004 | Tanaka |
| 2004/0047855 A1 | 3/2004 | Ingenito |
| 2004/0055606 A1 | 3/2004 | Hendricksen et al. |
| 2004/0059263 A1 | 3/2004 | DeVore et al. |
| 2004/0073155 A1 | 4/2004 | Laufer et al. |
| 2004/0073191 A1 | 4/2004 | Soltesz et al. |
| 2004/0073201 A1 | 4/2004 | Cooper et al. |
| 2004/0073241 A1 | 4/2004 | Barry et al. |
| 2004/0078026 A1 | 4/2004 | Wagner |
| 2004/0078054 A1 | 4/2004 | Biggs et al. |
| 2004/0087831 A1 | 5/2004 | Michels et al. |
| 2004/0097983 A1 | 5/2004 | Snyder et al. |
| 2004/0143282 A1 | 7/2004 | Dillard et al. |
| 2004/0144387 A1 | 7/2004 | Amar |
| 2004/0158228 A1 | 8/2004 | Perkins et al. |
| 2004/0167636 A1 | 8/2004 | Dillard et al. |
| 2004/0173218 A1 | 9/2004 | Yamada et al. |
| 2004/0199128 A1 | 10/2004 | Morris et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0211412 A1 | 10/2004 | Alferness et al. |
| 2004/0211434 A1 | 10/2004 | Loomas et al. |
| 2004/0220446 A1 | 11/2004 | Corcoran et al. |
| 2004/0220556 A1 | 11/2004 | Cooper et al. |
| 2004/0225254 A1 | 11/2004 | Tanaka et al. |
| 2004/0231674 A1 | 11/2004 | Tanaka |
| 2004/0237966 A1 | 12/2004 | Tanaka |
| 2004/0243140 A1 | 12/2004 | Alferness et al. |
| 2004/0244802 A1 | 12/2004 | Tanaka |
| 2004/0244803 A1 | 12/2004 | Tanaka |
| 2005/0005936 A1 | 1/2005 | Wondka |
| 2005/0015106 A1 | 1/2005 | Perkins et al. |
| 2005/0022809 A1 | 2/2005 | Wondka |
| 2005/0025816 A1 | 2/2005 | Tanaka |
| 2005/0033310 A1 | 2/2005 | Alferness et al. |
| 2005/0033344 A1 | 2/2005 | Dillard et al. |
| 2005/0043745 A1 | 2/2005 | Alferness et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0056292 A1 | 3/2005 | Cooper |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0061322 A1 | 3/2005 | Freitag |
| 2005/0066976 A1 | 3/2005 | Wondka |
| 2005/0085801 A1 | 4/2005 | Cooper et al. |
| 2005/0096529 A1 | 5/2005 | Cooper et al. |
| 2005/0103340 A1 | 5/2005 | Wondka |
| 2005/0107783 A1 | 5/2005 | Tom et al. |
| 2005/0131276 A1 | 6/2005 | Alferness et al. |
| 2005/0137518 A1 | 6/2005 | Biggs et al. |
| 2005/0137611 A1 | 6/2005 | Escudero et al. |
| 2005/0137712 A1 | 6/2005 | Biggs et al. |
| 2005/0137715 A1 | 6/2005 | Phan et al. |
| 2005/0145253 A1 | 7/2005 | Wilson et al. |
| 2005/0161040 A1 | 7/2005 | Tanaka |
| 2005/0166925 A1 | 8/2005 | Wilson et al. |
| 2005/0171396 A1 | 8/2005 | Pankratov et al. |
| 2005/0177144 A1 | 8/2005 | Phan et al. |
| 2005/0178385 A1 | 8/2005 | Dellaca et al. |
| 2005/0178389 A1 | 8/2005 | Shaw et al. |
| 2005/0192526 A1 | 9/2005 | Biggs et al. |
| 2005/0203483 A1 | 9/2005 | Perkins et al. |
| 2005/0205097 A1 | 9/2005 | Kyle, Jr. |
| 2005/0244401 A1 | 11/2005 | Ingenito |
| 2005/0281797 A1 | 12/2005 | Gong et al. |
| 2005/0281801 A1 | 12/2005 | Gong et al. |
| 2005/0281802 A1 | 12/2005 | Gong et al. |
| 2005/0282748 A1 | 12/2005 | Gong et al. |
| 2005/0288549 A1 | 12/2005 | Mathis |
| 2005/0288550 A1 | 12/2005 | Mathis |
| 2005/0288684 A1 | 12/2005 | Aronson et al. |
| 2005/0288702 A1 | 12/2005 | McGurk et al. |
| 2006/0004400 A1 | 1/2006 | McGurk et al. |
| 2006/0009748 A1 | 1/2006 | Mathis |
| 2006/0025815 A1 | 2/2006 | McGurk et al. |
| 2006/0047291 A1 | 3/2006 | Barry |
| 2006/0076023 A1 | 4/2006 | Rapacki et al. |

| | | | |
|---|---|---|---|
| 2006/0079838 | A1 | 4/2006 | Walker et al. |
| 2006/0095002 | A1 | 5/2006 | Soltesz et al. |
| 2006/0107961 | A1 | 5/2006 | Tanaka |
| 2006/0116749 | A1 | 6/2006 | Willink et al. |
| 2006/0118125 | A1 | 6/2006 | Tanaka |
| 2006/0118126 | A1 | 6/2006 | Tanaka |
| 2006/0124126 | A1* | 6/2006 | Tanaka ............ 128/200.26 |
| 2006/0130830 | A1 | 6/2006 | Barry |
| 2006/0135947 | A1 | 6/2006 | Soltesz et al. |
| 2006/0135984 | A1 | 6/2006 | Kramer et al. |
| 2006/0142672 | A1 | 6/2006 | Keast et al. |
| 2006/0161233 | A1 | 7/2006 | Barry et al. |
| 2006/0162731 | A1 | 7/2006 | Wondka et al. |
| 2006/0206147 | A1 | 9/2006 | DeVore et al. |
| 2006/0212046 | A1 | 9/2006 | Pearce et al. |
| 2006/0212051 | A1 | 9/2006 | Snyder et al. |
| 2006/0235432 | A1 | 10/2006 | DeVore et al. |
| 2006/0235467 | A1 | 10/2006 | DeVore |
| 2006/0264772 | A1 | 11/2006 | Aljuri et al. |
| 2006/0276807 | A1 | 12/2006 | Keast et al. |
| 2006/0280772 | A1 | 12/2006 | Roschak et al. |
| 2006/0280773 | A1 | 12/2006 | Roschak et al. |
| 2006/0283462 | A1 | 12/2006 | Fields et al. |
| 2007/0005083 | A1 | 1/2007 | Sabanathan et al. |
| 2007/0027434 | A1 | 2/2007 | Pedersen et al. |
| 2007/0043350 | A1 | 2/2007 | Soltesz et al. |
| 2007/0051372 | A1 | 3/2007 | Tanaka |
| 2007/0055175 | A1 | 3/2007 | Caro |
| 2007/0088300 | A1 | 4/2007 | Cline et al. |
| 2007/0123922 | A1 | 5/2007 | Cooper et al. |
| 2007/0128174 | A1 | 6/2007 | Kleinsek et al. |
| 2007/0142742 | A1 | 6/2007 | Aljuri et al. |
| 2007/0163598 | A1 | 7/2007 | Chang et al. |
| 2007/0185531 | A1 | 8/2007 | Rimbaugh et al. |
| 2007/0186932 | A1 | 8/2007 | Wondka et al. |
| 2007/0186933 | A1 | 8/2007 | Domingo et al. |
| 2007/0299424 | A1 | 12/2007 | Cumming et al. |
| 2008/0281151 | A1 | 11/2008 | Chang et al. |
| 2008/0281295 | A1 | 11/2008 | Chang et al. |
| 2008/0281433 | A1 | 11/2008 | Chang et al. |
| 2008/0283065 | A1 | 11/2008 | Chang et al. |
| 2008/0287878 | A1 | 11/2008 | Tanaka |
| 2008/0287973 | A1 | 11/2008 | Aster et al. |
| 2008/0295829 | A1 | 12/2008 | Evens |
| 2009/0205641 | A1 | 8/2009 | Tanaka |
| 2009/0205643 | A1 | 8/2009 | Tanaka et al. |
| 2009/0205644 | A1 | 8/2009 | Tanaka et al. |
| 2009/0205645 | A1 | 8/2009 | Tanaka et al. |
| 2009/0205646 | A1 | 8/2009 | Tanaka et al. |
| 2009/0205647 | A1 | 8/2009 | Plough et al. |
| 2009/0205648 | A1 | 8/2009 | Tanaka et al. |
| 2009/0205649 | A1 | 8/2009 | Tanaka et al. |
| 2009/0205650 | A1 | 8/2009 | Tanaka et al. |
| 2009/0205651 | A1 | 8/2009 | Tanaka et al. |
| 2009/0205658 | A1 | 8/2009 | Tanaka et al. |
| 2009/0205665 | A1 | 8/2009 | Tanaka et al. |
| 2009/0209856 | A1 | 8/2009 | Tanaka et al. |
| 2009/0209906 | A1 | 8/2009 | Tanaka et al. |
| 2009/0209909 | A1 | 8/2009 | Tanaka et al. |
| 2009/0209917 | A1 | 8/2009 | Tanaka et al. |
| 2009/0209924 | A1 | 8/2009 | Tanaka |
| 2009/0209936 | A1 | 8/2009 | Tanaka et al. |
| 2009/0209970 | A1 | 8/2009 | Tanaka et al. |
| 2009/0209971 | A1 | 8/2009 | Tanaka et al. |

FOREIGN PATENT DOCUMENTS

| | | |
|---|---|---|
| EP | 1658867 | 5/2006 |
| EP | 1815821 | 8/2007 |
| EP | 2242527 | 10/2010 |
| JP | 62-2028747 U | 6/1986 |
| JP | 2000197706 | 7/2000 |
| RU | 2192185 | 10/2002 |
| WO | WO 96/39960 | 12/1996 |
| WO | WO 9827878 A1 * | 7/1998 |
| WO | WO 99/66975 | 12/1999 |
| WO | WO 00/76577 A1 | 12/2000 |
| WO | WO 01/45568 A1 | 6/2001 |
| WO | WO2005070480 | 8/2005 |

OTHER PUBLICATIONS

Rockey, Edward E., "Tube Pneumonostomy for Thoracotomy Reject Crippling Bulbous Emphysema", New York State Journal of Medicine Mar. 1, 1973: 664-671.

Rousseau et al., "Self-expandable Prostheses in the Tracheobronchial Tree", Thoracic Radiology 1993; 188: 199-203.

Russi et al., "Lung volume reduction surgery: what can we learn from the National Emphysema Treatment Trial?" European Respiratory Journal 2003; 22: 571-573.

Saad et al., "Surgical treatment of bullae for Bulbous emphysema: a simple drainage", J. Pneumologia 2000; 26(3): 1-11, retrieved from <http://www.scielo.br/scielo.php?script=arttext&pid=S0102-35862000000300003&lng=e . . . > May 2, 2007.

Shah, Pallav, "Surgical and Non-surgical Volume Reduction for COPD", Presented at the Clinical Consensus on COPD, Mar. 2-3, 2007, Novotel London West, pp. 1-44.

Shah et al., "Surgical Treatment of Bulbous Emphysema: Experience with the Brompton Technique", Annals of Thoracic Surgery 1994; 58: 1452-1456.

Shim et al., "Percutaneous Drainage of Lung Abscess", Lung 1990; 168: 201-207.

Snell et al., "The Potential for Bronchoscopic Lung Volume Reduction Using Bronchial Prostheses: A Pilot Study", Chest 2003; 124: 1073-1080.

Snell, Gregory I., "Airway Bypass Stenting for Severe Emphysema", retrieved from <http://www.ctsnet.org/sections/thoracic/newtechnology/article-4.html>, Aug. 6, 2007, 4 pages.

Springmeyer, Steven C., "Development of a Bronchial Valve for Treatment of Severe Emphysema", retrieved from <http://www.ctsnet.org/sections/thoracic/newtechnology/article-10.html>, Jul. 16, 2007, 6 pages.

Stewart et al., "Decompression of Giant Bulla in Acute Pneumonia: Surgical Palliation Prior to Definitive Management", Ann Thoracic Surg 2006; 82: 2308-2309.

Sugarmann et al., "Mesh insertion as an aid for pleurodesis", Journal of Cardiovascular Surgery 1996; 37 (Suppl. 1 to No. 6):173-5.

Swallow et al., "Quadriceps strength predicts mortality in patients with moderate to severe chronic obstructive pulmonary disease", Thorax 2007; 62: 115-120.

Symbas et al., "Nontuberculous Pleural Empyema in Adults, The Role of a Modified Eloesser Procedure in Its Management", The Annals of Thoracic Surgery 1971; 12: 69-78.

Takizawa et al., "Computed tomography-guided drainage for large pulmonary bullae", Interactive Cardiovascular and Thoracic Surgery 2004; 3: 283-285.

Terry et al., "Collateral Ventilation in Man", The New England Journal of Medicine 1978; 298(1): 10-15.

Thourani et al., "Twenty-six Years of Experience With the Modified Eloesser Flap", Ann Thorac Surg 2003; 76: 401-406.

Toma et al., "Brave new world for interventional bronchoscopy", Thorax 2005; 60: 180-181.

Ugama et al., "Drainage of Giant Bulla with Balloon Catheter Using Chemical Irritant and Fibrin Glue", Chest 1988; 94(6): 1289-1290.

Vainrub et al., "Percutaneous Drainage of Lung Abscess", American Review of Respiratory Disease 1978; 117: 153-160.

Venn et al., "Intracavity drainage for Bulbous, emphysematous lung disease: experience with the Brompton technique", Thorax 1988; 43: 998-1002.

Wood et al., "A multicenter trial of an intrabronchial valve for treatment of severe emphysema", The Journal of Thoracic and Cardiovascular Surgery 2007; 133: 65-73.e2.

Woodring et al., "Pneumothorax ex vacuo", Chest 1996, 110: 1102-1124.

Woolcock et al., "Mechanical factors influencing collateral ventilation in human, dog, and pig lungs", Journal of Applied Physiology 1971, 30: 99-115.

Yellin et al., "Percutaneous Tube Drainage: The Treatment of Choice for Refractory Lung Abscess", The Annals of Thoracic Surgery 1985; 39: 266-270.

Yim et al., "Minimally invasive thoracic surgery: where do we stand now?" Hong Kong Medical Journal 1995; 1: 115-122.

Yim et al., "Early results of endoscopic lung volume reduction for emphysema", The Journal of Thoracic and Cardiovascular Surgery 2004; 127: 1564-1573.
International Search Report for PCT/US/2009/034374 dated Aug. 28, 2009; 13 pages.
International Search Report for PCT/US/2009/034380 dated Sep. 24, 2009; 12 pages.
International Search Report for PCT/US2009/034322 dated Oct. 5, 2009; 14 pages.
International Search Report for PCT/US2009/034406 dated Dec. 2, 2009; 16 pages.
Extended European Search Report dated Jun. 22, 2011 for PCT/US2009034374, 7 pages.
Extended European Search Report dated Jun. 15, 2011 for PCT/US2009034322, 7 pages.
Extended European Search Report dated Sep. 16, 2011 for PCT/US2009034380, 8 pages.
Aljuri et al., "Validation and pilot clinical study of a new bronchoscopic method to measure collateral ventilation before endobronchial lung volume reduction", J Appl Physio 106: 774-783, 2009.
Al-Salem et al., "Computed tomography-guided percutaneous needle aspiration of lung abscesses in neonates and children", Pediatr Surg Int (1997) 12: 417-419, copyright Springer-Verlag 1997.
Ball, Jr et al., "Percutaneous Drainage of Chest Abscesses in Children", Radiology 1989; 171: 431-434.
Becker et al., "Lung Volumes before and after Lung Volume Reduction Surgery: Quantitative CT Analysis", Am J Respir Crit Care Med 1998; 157: 1593-1599.
Brenner et al., "Innovative Approaches to Lung Volume Reduction for Emphysema", Chest 2004; 126: 238-248.
Brutinel et al., "A two-year experience with the neodymium-YAG laser in endobronchial obstruction", Chest 1987; 91: 159-165.
Celli et al. "Standards for the diagnosis and treatment of patients with COPD: a summary of the ATS/ERS position paper", European Respiratory Journal 2004; 23; 932-946.
Cetti et al., "Collateral ventilation", Thorax 2006; 61: 371-373.
Chino et al., "Ventilation of Excised Human Lungs Via Spiracles through the Pleura", Thematic Poster Session (Abstract p. A546) Session: 12:45 pm-4:15 pm, Mechanics of the Lung and Respiratory System (2003).
Choong et al., "Feasibility and safety of airway bypass stent placement and influence of topical mitomycin C on stent patency", The Journal of Thoracic and Cardiovascular Surgery 2005; 129: 632-638.
Choong et al., "Transpleural ventilation of explanted human lungs", Thorax 2007; 62: 623-630; originally published online Apr. 5, 2007.
Cope, J. Hallam, "Monaldi Procedure", Presented at the annual meeting of the California Tuberculosis and Health Association and the California Trudeau Society, Mar. 30-Apr. 1, 1950, San Diego; retrieved from California Medicine Dec. 1950; vol. 73, No. 6: 563-564.
Dumon, J. F., "A Dedicated Tracheobronchial Stent", Chest 1990; 97: 328-332.
Eloesser, "An Operation for Tuberculous Empyema", Chest 1935; 1: 8-23.
Fein, Alan M, "Lung Volume Reduction Surgery: Answering the Crucial Questions", Chest 1998; 113: 277-282.
Fernandes et al., "*Airway Hyperresponsiveness: From Molecules to Bedside Invited Review*: Do inflammatory mediators influence the contribution of airway smooth muscle contraction to airway hyperresponsiveness in asthma?", Journal Appl Physiol 2003; 95; 844-853.
Fessler, Henry E., "Collateral Ventilation, the Bane of Bronchoscopic Volume Reduction", Am J Respir Crit Care Med 2005; 171: 423-425.
Frawley et al., "Airway Pressure Release Ventilation: Theory and Practice", AACN Clinical Issues 2001; vol. 12, No. 2: 234-246.
Freitag et al., "Theoretical and experimental basis for the development of a dynamic airway stent", European Respiratory Journal 1994; 7: 2038-2045.
Ghaye et al., "Imaging guided thoracic interventions", European Respiratory Journal 2001; 17: 507-528.
Golding et al., "External drainage of large bullae in severe generalized emphysema", Journal of Thoracic and Cardiovascular Surgery Jun. 1968; vol. 55, No. 6: 891-894.
Goldstraw et al., "The Surgical Treatment of Emphysema: The Brompton Approach", Chest Surgery Clinics of North America Nov. 1995; vol. 5, No. 4: 777-797.
Habashi, Nader M., "Other approaches to open-lung ventilation: Airway pressure release ventilation", Crit Care Med 2005, vol. 33, No. 3 (Suppl): S228-S240.
Harada et al., "Re-expansion of Refractory Atelectasis Using a Bronchofiberscope with a Balloon Cuff", Chest 1983; 84: 725-728.
Head et al., "Intracavitary Suction (Monaldi) in the Treatment of Emphysematous Bullae and Blebs", Journal of Thoracic Surgery Dec. 1949; vol. 18, No. 6: 761-776.
Heimlich, Henry J., "Respiratory Rehabilitation with Transtracheal Oxygen System", Ann Otol Rhinol Laryngol Nov./Dec. 1982; 91: 643-647.
Hogg et al., "Chronic obstructive pulmonary disease c2: Pathology and biochemistry of emphysema", Thorax 2002; 57: 830-834.
Hogg et al., "The Resistance of Collateral Channels in Excised Human Lungs", Journal of Clinical Investigation 1969; 48: 421-431.
Joannette, Albert, "Drainage of Tuberculous Cavities by Aspiration (Monaldi Method)", The Canadian Medical Association Journal Jan. 1941; 46-48.
Korpela et al., "Bioabsorbable Self-reinforced Poly-L-Lactide, Metallic, and Silicone Stents in the Management of Experimental Tracheal Stenosis", Chest 1999; 115: 490-495.
Lausberg et al., "Bronchial Fenestration Improves Expiratory Flow in Emphysematous Human Lungs", Annals of Thoracic Surgery 2003; 75: 393-398.
Lorenzo et al., "Lung Abscesses in Children: Diagnostic and Therapeutic Needle Aspiration", Radiology Oct. 1985; 157: 79-80.
MacArthur et al., "Intracavity suction and drainage in the treatment of emphysematous bullae", Thorax 1977; 32: 668-672.
Macklem, Peter T., "Collateral Ventilation", The New England Journal of Medicine Jan. 5, 1978; 298(1): 49-50.
Matson et al., "Evaluation of Various Surgical Procedures in the Treatment of Pulmonary Tuberculosis", Chest 1946; 12: 40-47.
McCoy, Robert, "Oxygen-Conserving Techniques and Devices", Respiratory Care Jan. 2000, vol. 45, No. 1: 95-104.
Meyers et al., "Chronic obstructive pulmonary disease 10: Bullectomy, lung volume reduction surgery, and transplantation for patients with chronic obstructive pulmonary disease", Thorax 2003; 58: 634-638.
Mineo et al., "Awake Nonresectional Lung Volume Reduction Surgery", Annals of Surgery 2006; 243: 131-136.
Monaldi, V., "Endocavitary Aspiration: Its Practical Application", Tubercle 1947: 223-228.
Monaldi, V., "Endocavitary Aspiration in the Treatment of Lung Abscess", Chest 1956; 29: 193-201.
Monaldi, V., "Endocavitary Aspiration in the Treatment of Pathological Cavities of the Lung", Proceedings of the International Conference on Tuberculosis, Scandinavian Journal of Respiratory Diseases Supplementum 1968; 65: 113-121.
U.S. Department of Health and Human Services; National Institutes of Health National Heart, Lung, and Blood Institute; "Chronic Obstructive Pulmonary Disease", NIH Publication No. 03-5229 Mar. 2003: 1-6.
Parker et al., "Percutaneous small bore catheter drainage in the management of lung abscesses", Chest 1987; 92: 213-218.
Petty, Thomas L., "The history of COPD", International Journal of COPD 2006; 1(1): 3-14.
Polkey, M. J., "Surgical procedures in emphysema: any impact on dynamic hyperinflation?" European Respiratory Review 2006; 15(100): 96-98.
Polkey, M. J., "Bronchoscopic lung volume reduction", European Respiratory Review 2006; 15(100): 99-103.

* cited by examiner

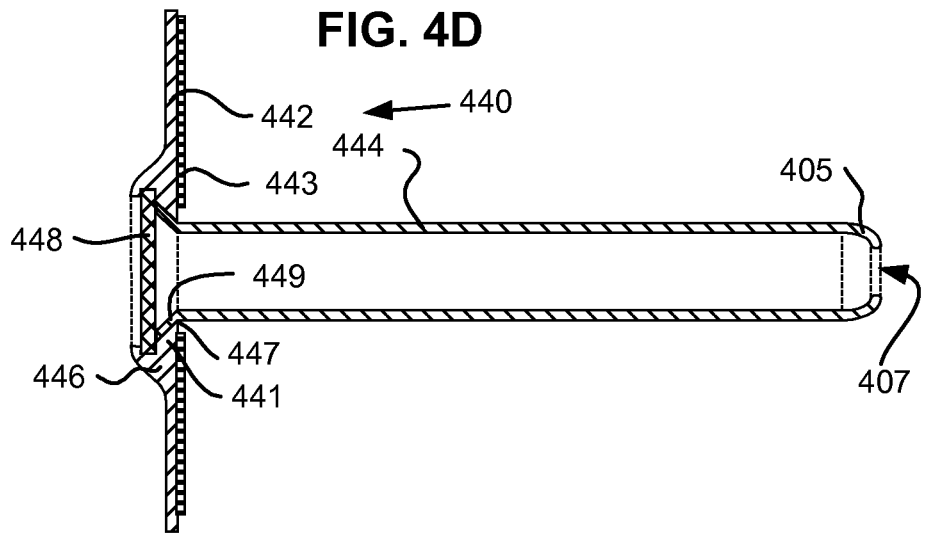
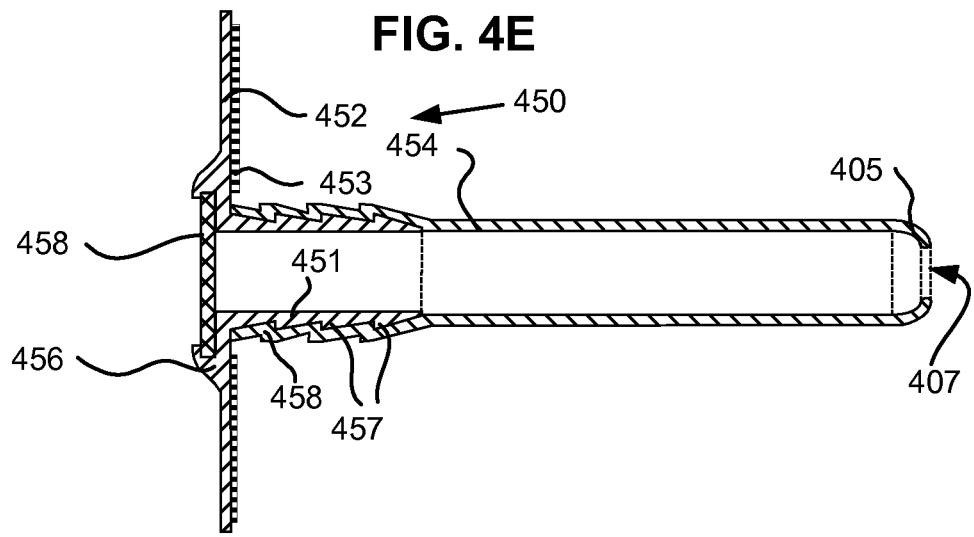
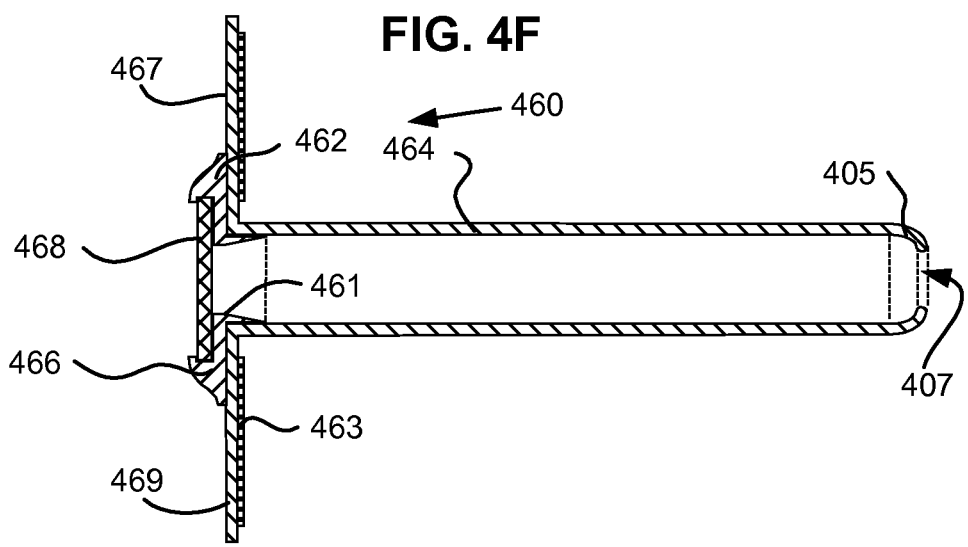

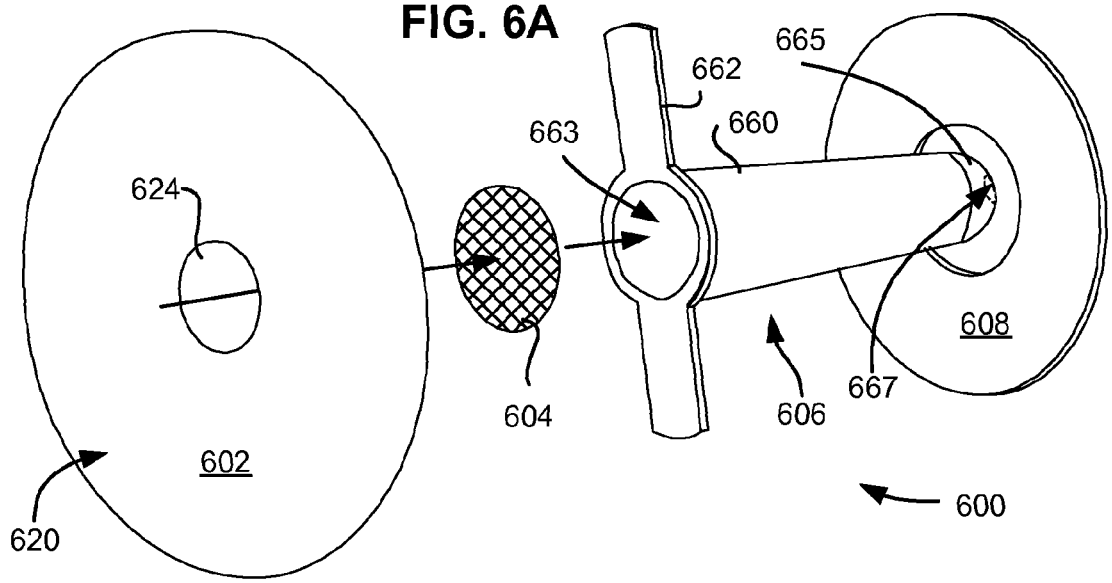
FIG. 6A
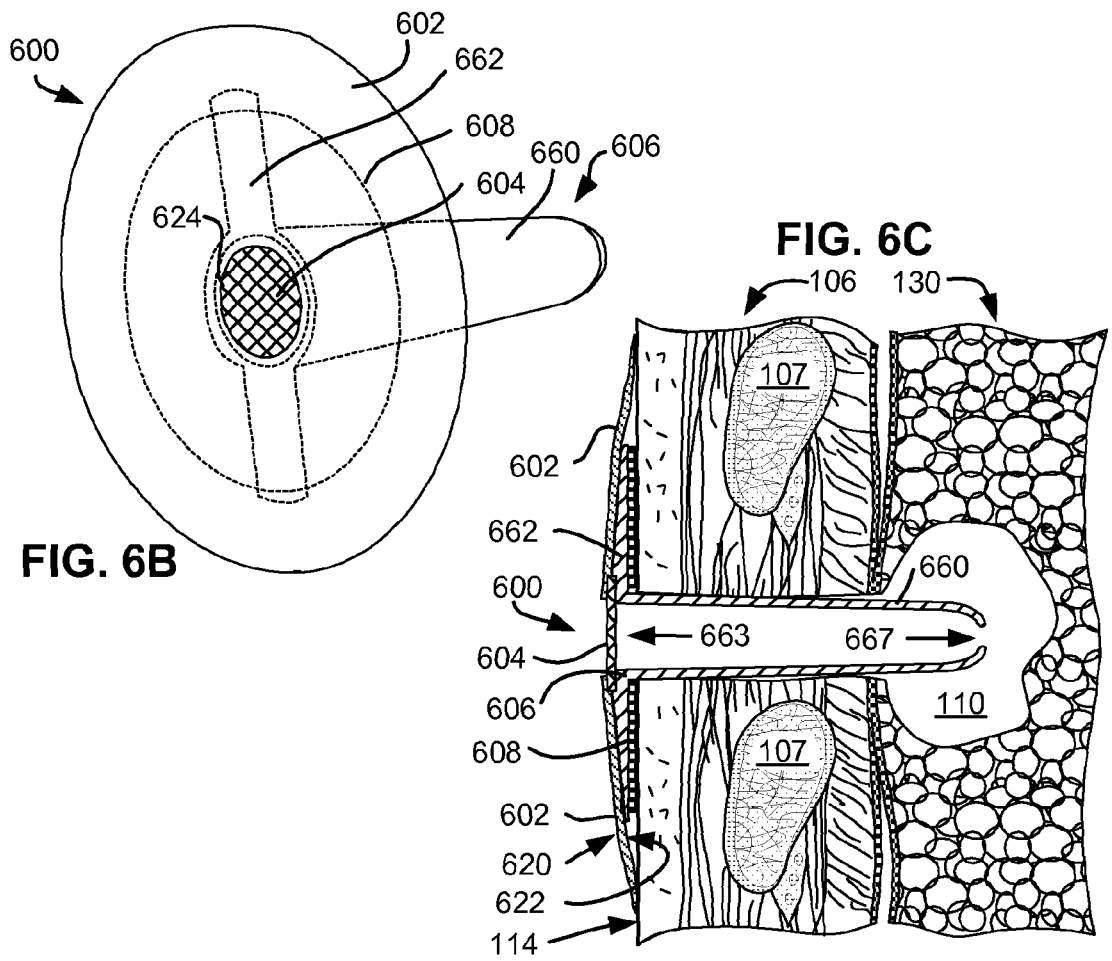
FIG. 6B
FIG. 6C

FIG. 6D
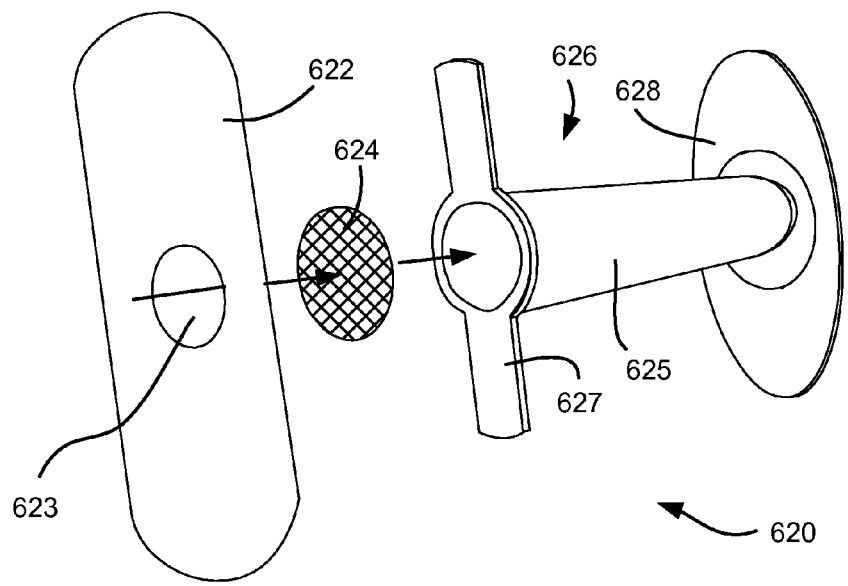
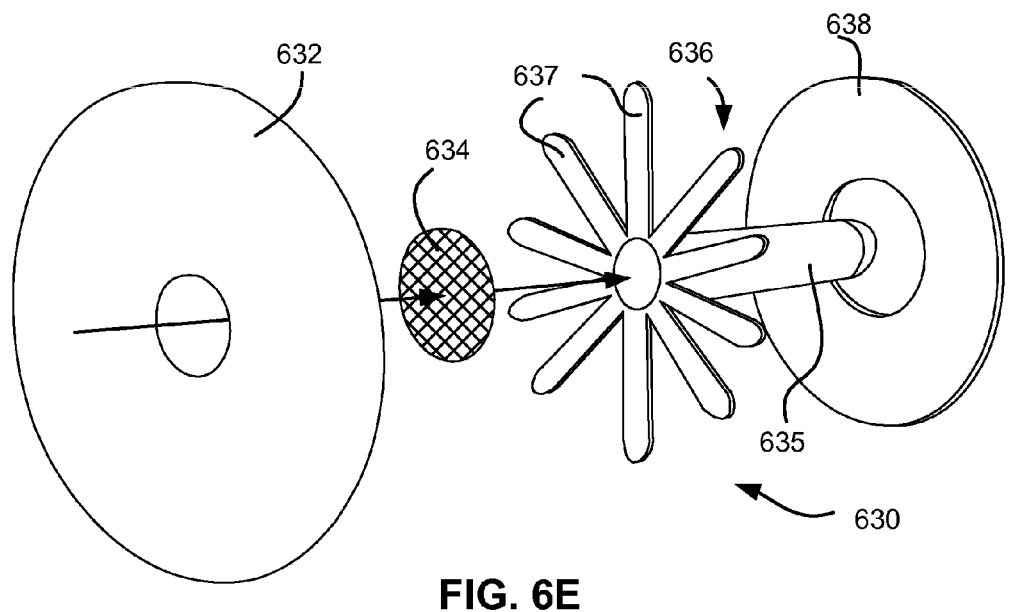
FIG. 6E

FIG. 6F
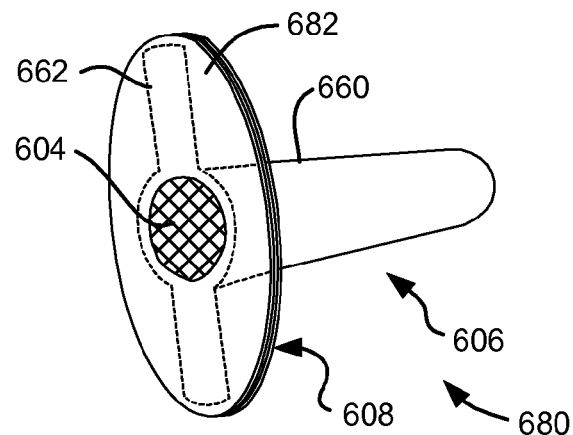
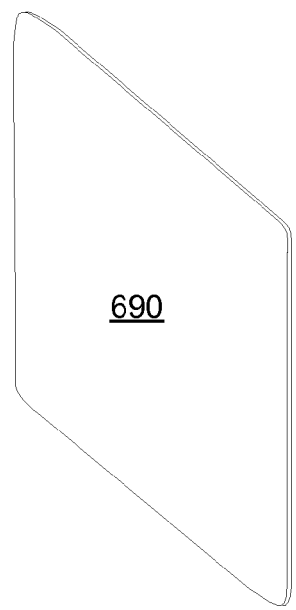
FIG. 6G
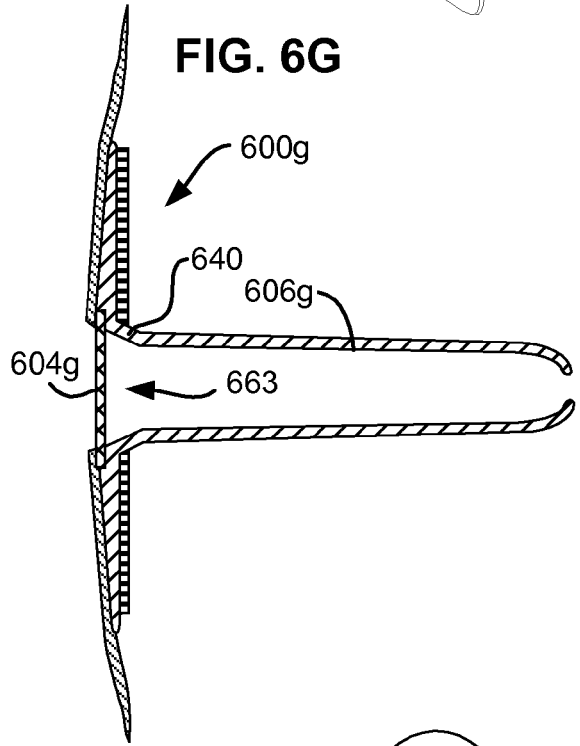
FIG. 6H
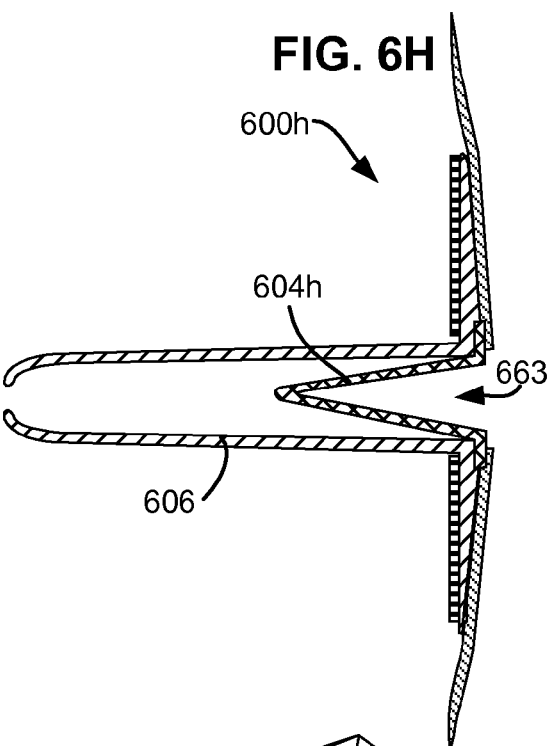
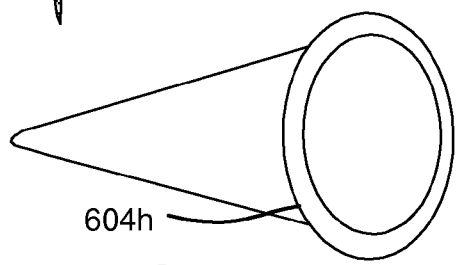
FIG. 6I
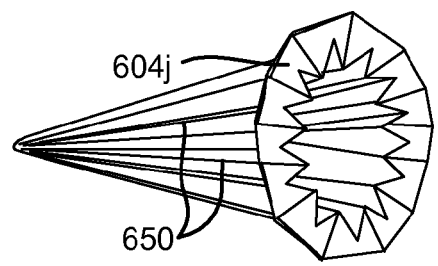
FIG. 6J

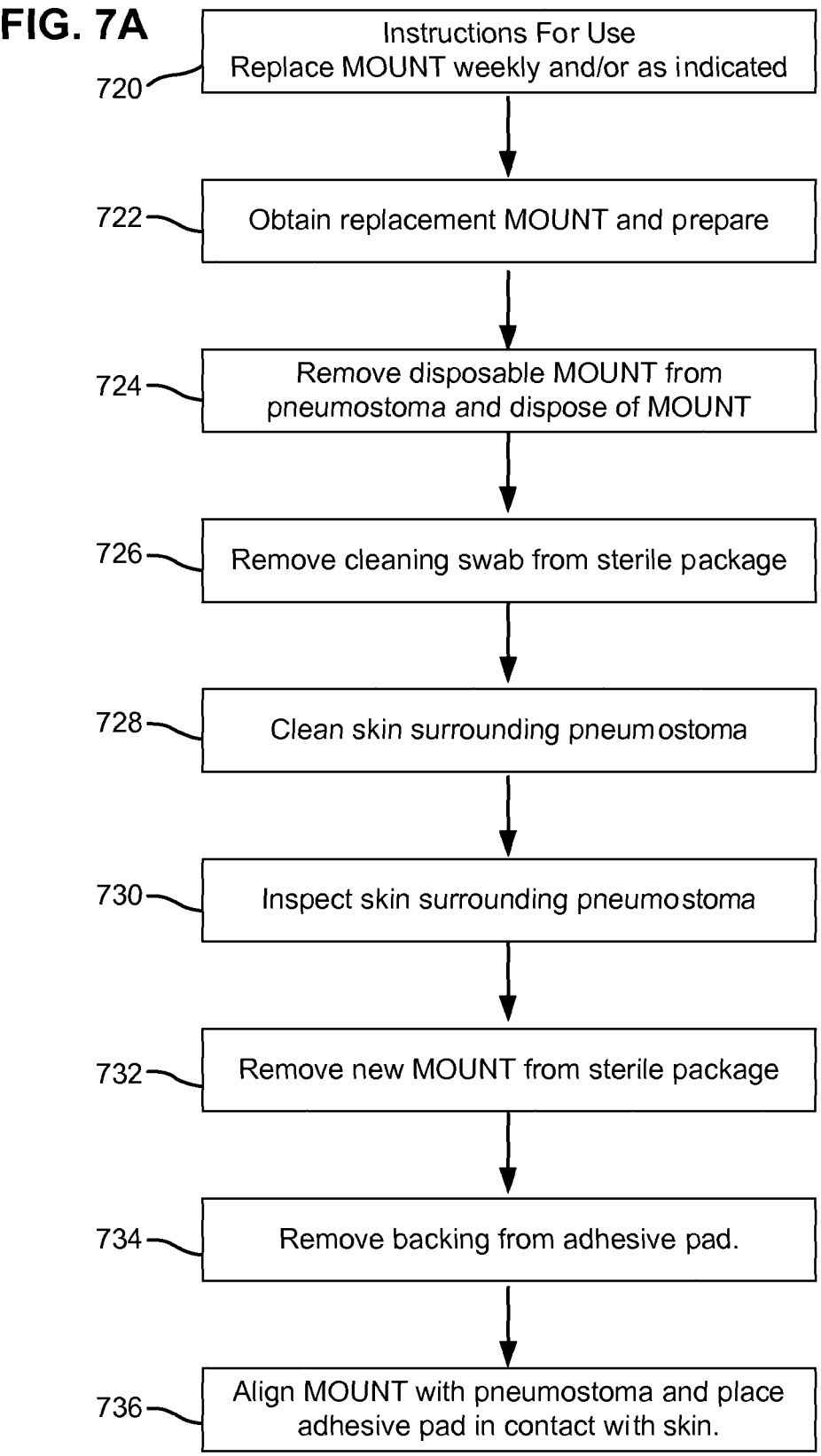

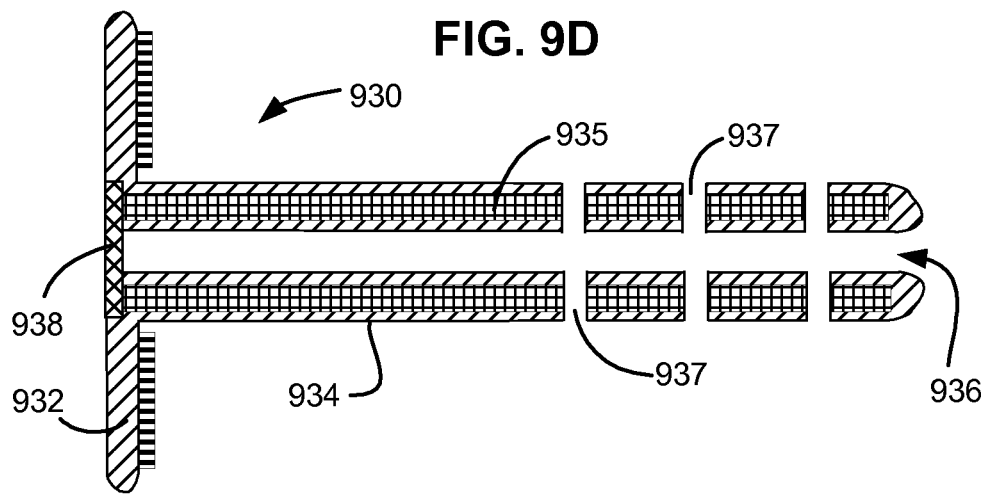
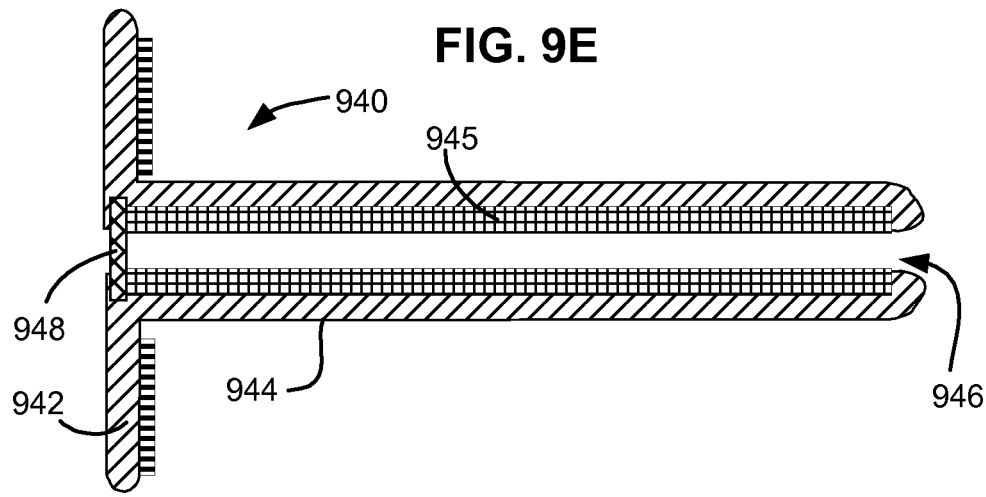
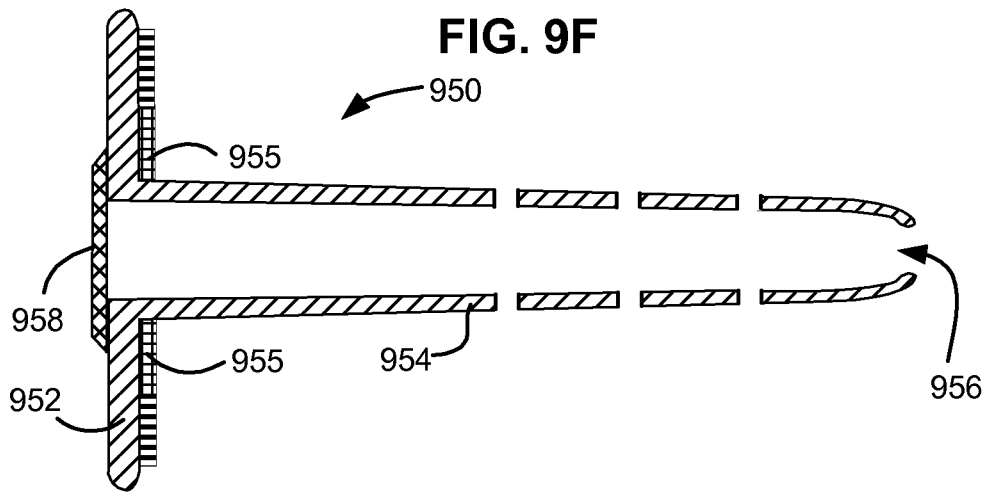

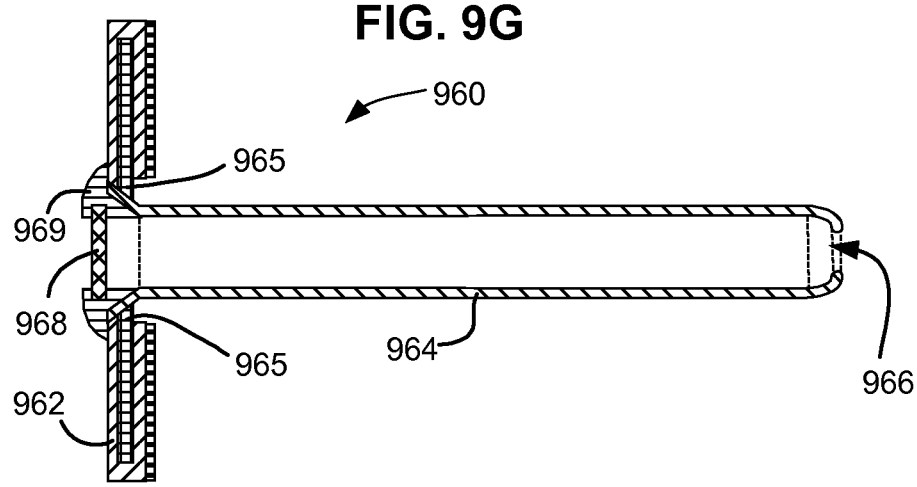
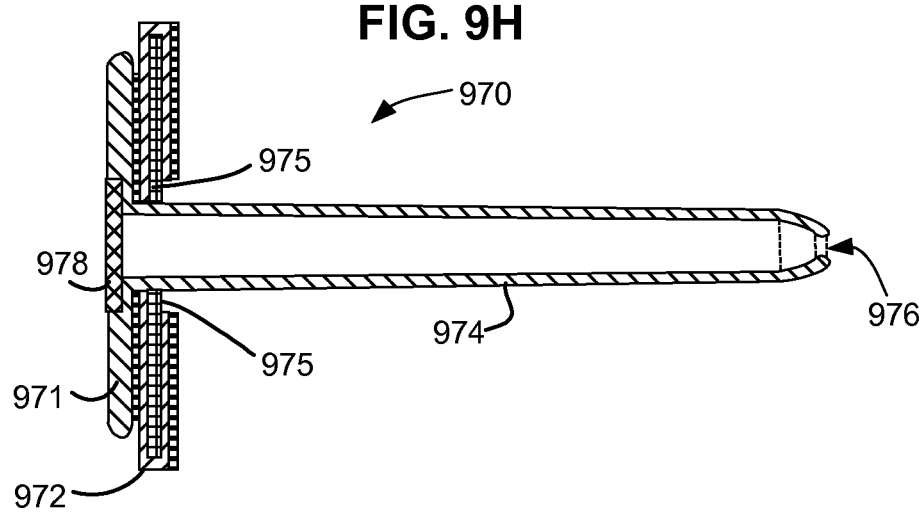

FIG. 10E
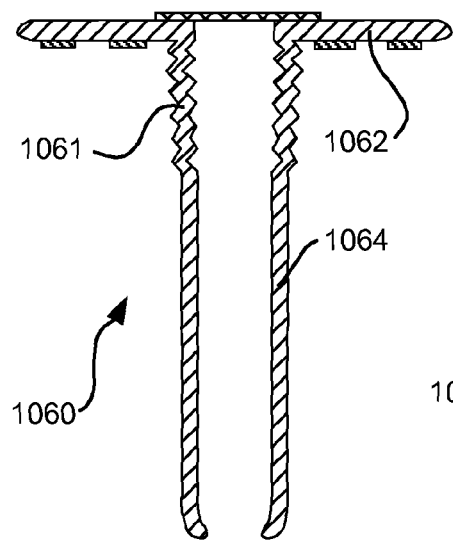
FIG. 10G
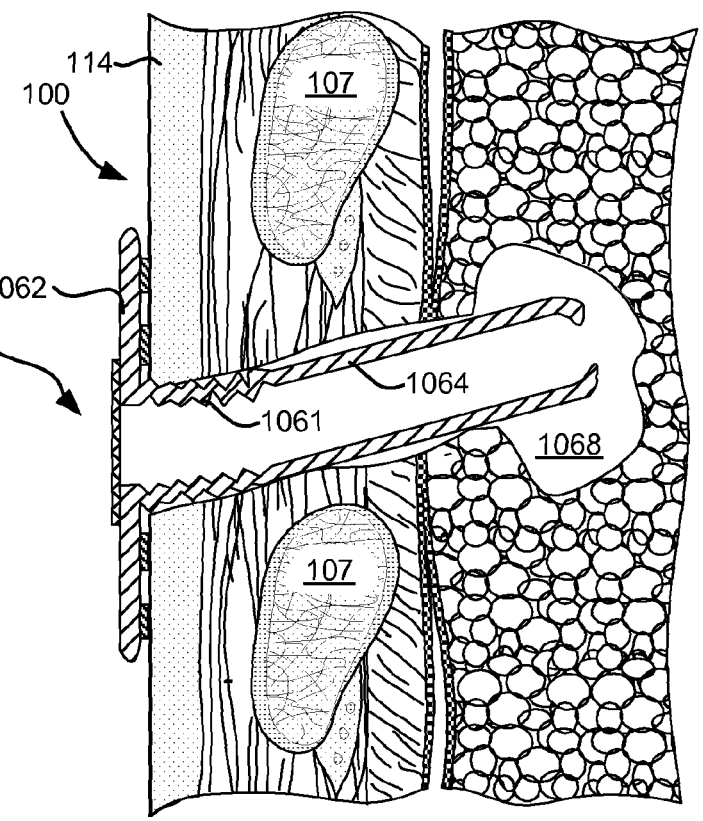
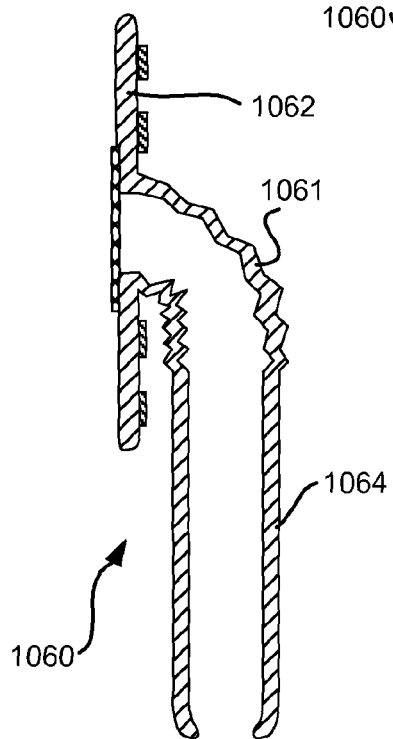
FIG. 10F

FIG. 11C
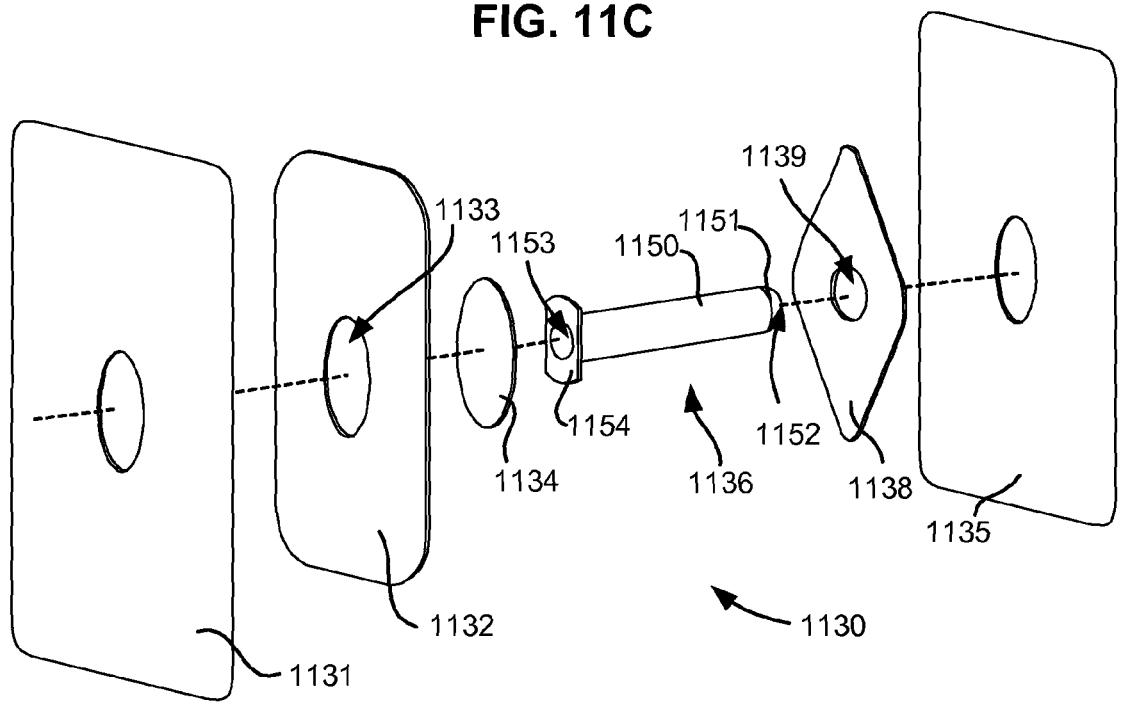
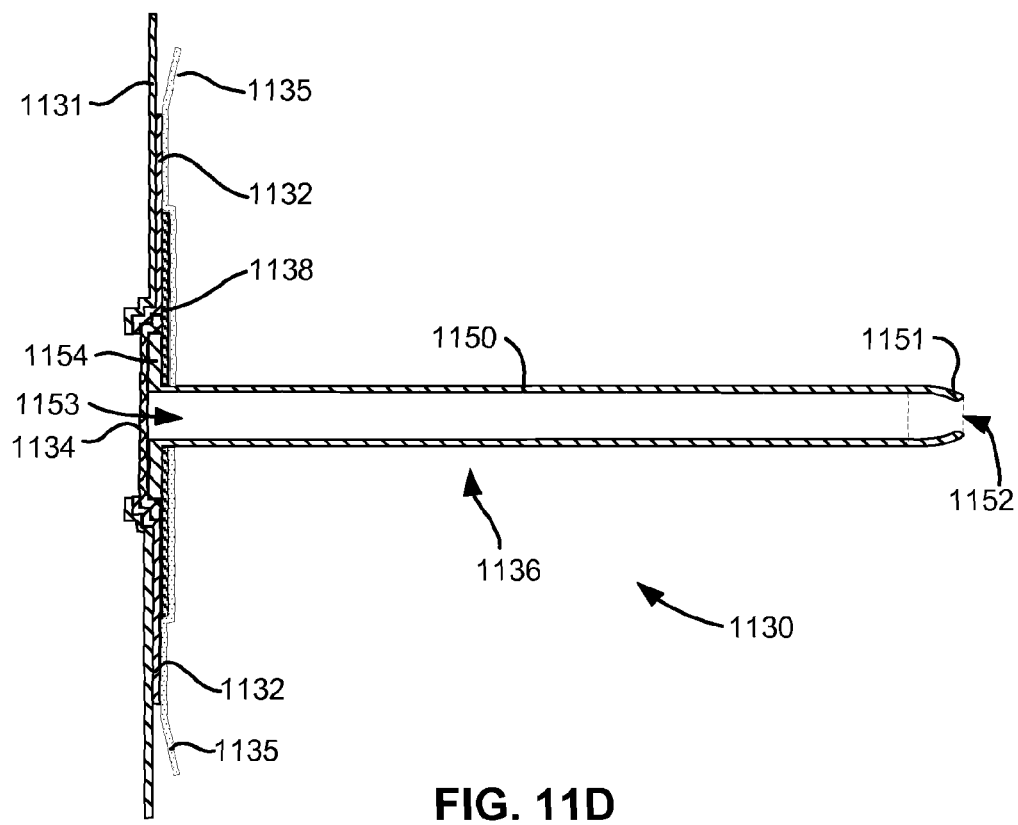
FIG. 11D

VARIABLE LENGTH PNEUMOSTOMA MANAGEMENT SYSTEM FOR TREATMENT OF CHRONIC OBSTRUCTIVE PULMONARY DISEASE

CLAIM TO PRIORITY

This application claims priority to all of the following applications including: U.S. Provisional Application No. 61/029,830, filed Feb. 19, 2008, entitled "ENHANCED PNEUMOSTOMA MANAGEMENT DEVICE AND METHODS FOR TREATMENT OF CHRONIC OBSTRUCTIVE PULMONARY DISEASE";

U.S. Provisional Application No. 61/032,877, filed Feb. 29, 2008, entitled "PNEUMOSTOMA MANAGEMENT SYSTEM AND METHODS FOR TREATMENT OF CHRONIC OBSTRUCTIVE PULMONARY DISEASE";

U.S. Provisional Application No. 61/038,371, filed Mar. 20, 2008, entitled "SURGICAL PROCEDURE AND INSTRUMENT TO CREATE A PNEUMOSTOMA AND TREAT CHRONIC OBSTRUCTIVE PULMONARY DISEASE";

U.S. Provisional Application No. 61/082,892, filed Jul. 23, 2008, entitled "PNEUMOSTOMA MANAGEMENT SYSTEM HAVING A COSMETIC AND/OR PROTECTIVE COVER";

U.S. Provisional Application No. 61/083,573, filed Jul. 25, 2008, entitled "DEVICES AND METHODS FOR DELIVERY OF A THERAPEUTIC AGENT THROUGH A PNEUMOSTOMA";

U.S. Provisional Application No. 61/084,559, filed Jul. 29, 2008, entitled "ASPIRATOR FOR PNEUMOSTOMA MANAGEMENT";

U.S. Provisional Application No. 61/088,118, filed Aug. 12, 2008, entitled "FLEXIBLE PNEUMOSTOMA MANAGEMENT SYSTEM AND METHODS FOR TREATMENT OF CHRONIC OBSTRUCTIVE PULMONARY DISEASE";

U.S. Provisional Application No. 61/143,298, filed Jan. 8, 2009, entitled "METHODS AND APPARATUS FOR THE CRYOTHERAPY CREATION OR RE-CREATION OF PNEUMOSTOMY"; and U.S. Provisional Application No. 61/151,581, filed Feb. 11, 2009, entitled "SURGICAL INSTRUMENTS AND PROCEDURES TO CREATE A PNEUMOSTOMA AND TREAT CHRONIC OBSTRUCTIVE PULMONARY DISEASE".

All of the afore-mentioned applications are incorporated herein by reference in their entireties.

CROSS-REFERENCE TO RELATED APPLICATIONS

This application is related to all of the above provisional applications and all the patent applications that claim priority thereto including:

This application is related to all of the following applications including U.S. patent application Ser. No. 12/388,465, filed Feb. 18, 2009, now U.S. Pat. No. 7,909,803, issued Mar. 22, 2011, entitled "ENHANCED PNEUMOSTOMA MANAGEMENT DEVICE AND METHODS FOR TREATMENT OF CHRONIC OBSTRUCTIVE PULMONARY DISEASE";

U.S. patent application Ser. No. 12/388,447, filed Feb. 18, 2009, entitled "PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,451, filed Feb. 18, 2009, entitled "PNEUMOSTOMA MANAGEMENT METHOD FOR TREATMENT OF CHRONIC OBSTRUCTIVE PULMONARY DISEASE";

U.S. patent application Ser. No. 12/388,435, filed Feb. 18, 2009, entitled "TWO-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,438, filed Feb. 18, 2009, entitled "ACCELERATED TWO-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,441, filed Feb. 18, 2009, entitled "SINGLE-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,446, filed Feb. 18, 2009, entitled "PERCUTANEOUS SINGLE-PHASE SURGICAL PROCEDURE FOR CREATING A PNEUMSOTOMA TO TREAT CHRONIC OBSTRUCTIVE PULMONARY DISEASE";

U.S. patent application Ser. No. 12/388,460, filed Feb. 18, 2009, entitled "PNEUMOSTOMA MANAGEMENT SYSTEM HAVING A COSMETIC AND/OR PROTECTIVE COVER"

U.S. patent application Ser. No. 12/388,455, filed Feb. 18, 2009, entitled "DEVICES AND METHODS FOR DELIVERY OF A THERAPEUTIC AGENT THROUGH A PNEUMOSTOMA";

U.S. patent application Ser. No. 12/388,461, filed Feb. 18, 2009, now U.S. Pat. No. 8,348,906, issued Jan. 8, 2013, entitled "ASPIRATOR FOR PNEUMOSTOMA MANAGEMENT";

U.S. patent application Ser. No. 12/388,462, filed Feb. 18, 2009, now U.S. Pat. No. 7,927,324 issued Apr. 19, 2011, entitled "ASPIRATOR AND METHOD FOR PNEUMOSTOMA MANAGEMENT";

U.S. patent application Ser. No. 12/388,458, filed Feb. 18, 2009, entitled "FLEXIBLE PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,459, filed Feb. 18, 2009, entitled "METHODS AND DEVICES FOR FOLLOW-UP CARE AND TREATMENT OF A PNEUMOSTOMA";

U.S. patent application Ser. No. 12/388,453, filed Feb. 18, 2009, now U.S. Pat. No. 8,252,003 issued Aug. 28, 2012, entitled "SURGICAL INSTRUMENTS FOR CREATING A PNEUMOSTOMA AND TREATING CHRONIC OBSTRUCTIVE PULMONARY DISEASE";

U.S. patent application Ser. No. 12/388,466, filed Feb. 18, 2009, entitled "ONE-PIECE PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,467, filed Feb. 18, 2009, now U.S. Pat. No. 8,347,880 issued Jan. 8, 2013, entitled "PNEUMOSTOMA MANAGEMENT SYSTEM WITH SECRETION MANAGEMENT FEATURES FOR TREATMENT OF CHRONIC OBSTRUCTIVE PULMONARY DISEASE";

U.S. patent application Ser. No. 12/388,468, filed Feb. 18, 2009, now U.S. Pat. No. 8,365,722 issued Feb. 5, 2013, entitled "MULTI-LAYER PNEUMOSTOMA MANAGEMENT SYSTEM AND METHODS FOR TREATMENT OF CHRONIC OBSTRUCTIVE PULMONARY DISEASE"; and U.S. patent application Ser. No. 12/388,470, filed Feb. 18, 2009, now U.S. Pat. No. 8,021,320 issued Sep. 20, 2011, entitled "SELF-SEALING DEVICE AND METHOD FOR DELIVERY OF A THERAPEUTIC AGENT THROUGH A PNEUMOSTOMA".

All of the afore-mentioned applications are incorporated herein by reference in their entireties. This patent application also incorporates by reference all patents, applications, and articles discussed and/or cited herein.

BACKGROUND OF THE INVENTION

In the United States alone, approximately 14 million people suffer from some form of Chronic Obstructive Pulmonary Disease (COPD). However, an additional ten million adults have evidence of impaired lung function indicating that COPD may be significantly underdiagnosed. The cost of COPD to the nation in 2002 was estimated to be $32.1 billion. Medicare expenses for COPD beneficiaries were nearly 2.5 times that of the expenditures for all other patients. Direct medical services accounted for $18.0 billion, and indirect cost of morbidity and premature mortality was $14.1 billion. COPD is the fourth leading cause of death in the U.S. and is projected to be the third leading cause of death for both males and females by the year 2020.

Chronic Obstructive Pulmonary Disease (COPD) is a progressive disease of the airways that is characterized by a gradual loss of lung function. In the United States, the term COPD includes chronic bronchitis, chronic obstructive bronchitis, and emphysema, or combinations of these conditions. In emphysema the alveoli walls of the lung tissue are progressively weakened and lose their elastic recoil. The breakdown of lung tissue causes progressive loss of elastic recoil and the loss of radial support of the airways which traps residual air in the lung. This increases the work of exhaling and leads to hyperinflation of the lung. When the lungs become hyperinflated, forced expiration cannot reduce the residual volume of the lungs because the force exerted to empty the lungs collapses the small airways and blocks air from being exhaled. As the disease progresses, the inspiratory capacity and air exchange surface area of the lungs is reduced until air exchange becomes seriously impaired and the individual can only take short shallow labored breaths (dyspnea).

The symptoms of COPD can range from the chronic cough and sputum production of chronic bronchitis to the severe disabling shortness of breath of emphysema. In some individuals, chronic cough and sputum production are the first signs that they are at risk for developing the airflow obstruction and shortness of breath characteristic of COPD. With continued exposure to cigarettes or noxious particles, the disease progresses and individuals with COPD increasingly lose their ability to breathe. Acute infections or certain weather conditions may temporarily worsen symptoms (exacerbations), occasionally where hospitalization may be required. In others, shortness of breath may be the first indication of the disease. The diagnosis of COPD is confirmed by the presence of airway obstruction on testing with spirometry. Ultimately, severe emphysema may lead to severe dyspnea, severe limitation of daily activities, illness and death.

There is no cure for COPD or pulmonary emphysema, only various treatments, for ameliorating the symptoms. The goal of current treatments is to help people live with the disease more comfortably and to prevent the progression of the disease. The current options include: self-care (e.g., quitting smoking), medications (such as bronchodilators which do not address emphysema physiology), long-term oxygen therapy, and surgery (lung transplantation and lung volume reduction surgery). Lung Volume Reduction Surgery (LVRS) is an invasive procedure primarily for patients who have a localized (heterogeneous) version of emphysema; in which, the most diseased area of the lung is surgically removed to allow the remaining tissue to work more efficiently. Patients with diffuse emphysema cannot be treated with LVRS, and typically only have lung transplantation as an end-stage option. However, many patients are not candidates for such a taxing procedure.

A number of less-invasive surgical methods have been proposed for ameliorating the symptoms of COPD. In one approach new windows are opened inside the lung to allow air to more easily escape from the diseased tissue into the natural airways. These windows are kept open with permanently implanted stents. Other approaches attempt to seal off and shrink portions of the hyperinflated lung using chemical treatments and/or implantable plugs. However, these proposals remain significantly invasive and are still in clinical trails. None of the surgical approaches to treatment of COPD has been widely adopted. Therefore, a large unmet need remains for a medical procedure that can sufficiently alleviate the debilitating effects of COPD and emphysema.

SUMMARY OF THE INVENTION

In view of the disadvantages of the state of the art, Applicants have developed a method for treating COPD in which an artificial passageway is made through the chest wall into the lung. An anastomosis is formed between the artificial passageway and the lung by creating a pleurodesis between the visceral and parietal membranes surrounding the passageway as it enters the lung. The pleurodesis prevents air from entering the pleural cavity and causing a pneumothorax (deflation of the lung due to air pressure in the pleural cavity). The pleurodesis is stabilized by a fibrotic healing response between the membranes. The artificial passageway through the chest wall also becomes epithelialized. The result is a stable artificial aperture through the chest wall which communicates with the parenchymal tissue of the lung.

The aperture into the lung through the chest wall is referred to herein as a pneumostoma. A pneumostoma provides an extra pathway that allows air to exit the lung while bypassing the natural airways which have been impaired by COPD and emphysema. By providing this ventilation bypass, the pneumostoma allows the stale air trapped in the lung to escape from the lung thereby shrinking the lung (reducing hyperinflation). By shrinking the lung, the ventilation bypass reduces breathing effort (reducing dyspnea), allows more fresh air to be drawn in through the natural airways and increases the effectiveness of all of the tissues of the lung for gas exchange. Increasing the effectiveness of gas exchange allows for increased absorption of oxygen into the bloodstream and also increased removal of carbon dioxide. Reducing the amount of carbon dioxide retained in the lung reduces hypercapnia which also reduces dyspnea. The pneumostoma thereby achieves the advantages of lung volume reduction surgery without surgically removing a portion of the lung or sealing off a portion of the lung.

Procedures, techniques and tools for creating a pneumostoma are described in applicants' copending application entitled "Surgical Procedure And Instrument To Create A Pneumostoma And Treat Chronic Obstructive Pulmonary Disease" to Tanaka (U.S. Provisional No. 61/038,371, filed Mar. 20, 2008). Additional devices for managing a pneumostoma are described in applicants' copending patent application titled "Pneumostoma Management System And Methods For Treatment For Chronic Obstructive Pulmonary Disease"

to Tanaka (U.S. Provisional No. 61/032,877 filed Feb. 29, 2008). These provisional applications, and all other patents and patent applications referred to herein, are incorporated by reference in their entireties.

In accordance with one embodiment, the present invention provides a pneumostoma management system which includes a pneumostoma management device having a temporarily implantable pneumostoma vent. The temporarily implantable pneumostoma vent is placed into a pneumostoma to maintain the patency of the pneumostoma, prevent the entry of foreign substances into the lung, control air flow through the pneumostoma and collect any materials that may exit the lung.

In accordance with one embodiment, the present invention provides a two-piece pneumostoma management system which includes a partially-implantable pneumostoma vent and a chest mount. The partially-implantable pneumostoma vent is placed into a pneumostoma through an aperture in the chest mount. The partially-implantable pneumostoma management device is designed such that every component is larger than the aperture in the chest mount and thus cannot enter the pneumostoma.

In accordance with another embodiment of the present invention, a method is provided for using the disclosed pneumostoma management systems to maintain the patency of the pneumostoma, prevent the entry of foreign substances into the lung, control air flow through a pneumostoma and control any materials that may exit the lung.

In accordance with particular embodiments, the present invention provides a flexible pneumostoma management system for maintaining the patency of a pneumostoma while controlling the flow of material through the pneumostoma. The pneumostoma management system includes a pneumostoma vent having a thin flexible flange which attaches to the chest and conforms to the skin of the patient. The pneumostoma vent includes a filter. In some embodiments a thin flexible chest mount is positioned between the flange and the chest of the patient.

In accordance with a specific embodiment, the present invention provides a pneumostoma management system having: a tube adapted for insertion into the chest through the pneumostoma, the tube having a lumen, a proximal end and a distal end, the distal end of the tube having an atraumatic tip, the distal end of the tube having at least one opening adapted to admit gases from the lung; and a flange connected to the proximal end of the tube such that an opening in the flange connects to the lumen of the tube, the flange projecting a sufficient distance from the tube to preclude passage of flange into the pneumostoma, the flange being sufficiently thin and flexible to conform to the chest of the patient, the flange having an adhesive coating for releasably securing the flange to the chest of the patient; and a filter disposed over the opening in the flange and secured to one of the flange and tube such that gases passing into and out of the lumen of the tube pass through the filter.

Thus, various systems, components and methods are provided for managing a pneumostoma and thereby treating COPD. Other objects, features and advantages of the invention will be apparent from drawings and detailed description to follow.

BRIEF DESCRIPTION OF THE DRAWINGS

The above and further features, advantages and benefits of the present invention will be apparent upon consideration of the present description taken in conjunction with the accompanying drawings.

FIGS. 4A-4F show alternative pneumostoma management devices according to embodiments of the present invention.

FIGS. 6A-6F show alternative pneumostoma management devices according to embodiments of the present invention.

FIGS. 6G-6J show alternative filter arrangements for pneumostoma management devices according to embodiments of the invention.

FIGS. 7A and 7B show instructions for using a pneumostoma management system in accordance with an embodiment of the present invention.

FIGS. 9A-9H show alternative pneumostoma vent and chest mount configurations for pneumostoma management systems according to embodiments of the present invention.

FIGS. 10E-10G show views of an alternative pneumostoma vent according to and embodiment of the present invention.

FIGS. 11A-11D show views alternative pneumostoma vents according to a preferred embodiments of the present invention.

DETAILED DESCRIPTION OF THE INVENTION

Figure 1A:
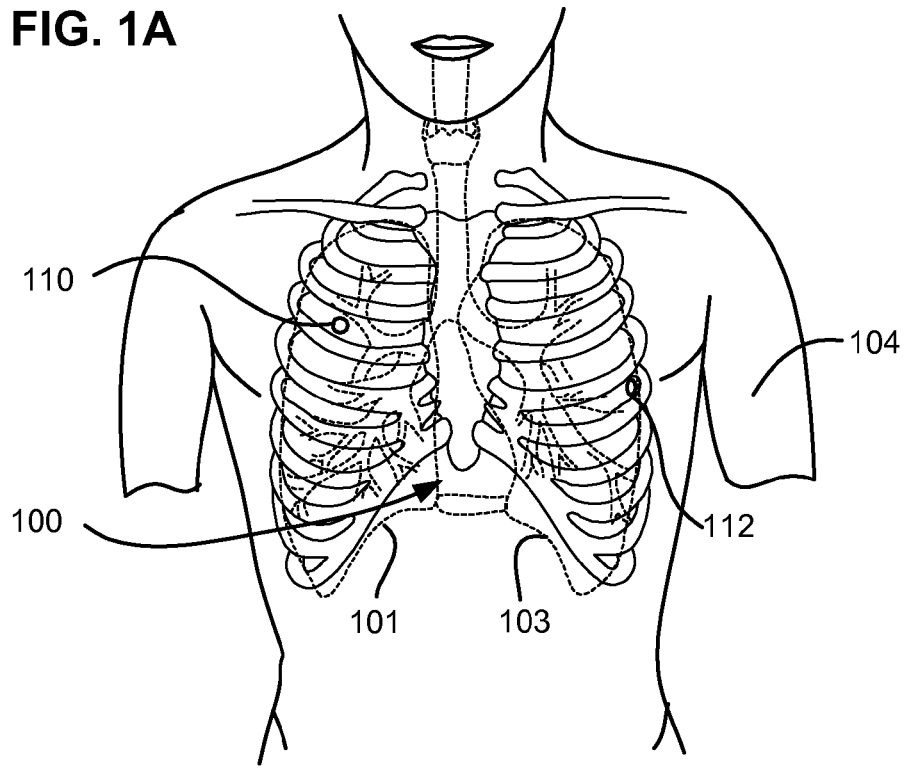
FIG. 1A shows the chest of a patient indicating alternative locations for a pneumostoma that may be managed using the device and methods of the present invention.

The following description is of the best modes presently contemplated for practicing various embodiments of the present invention. The description is not to be taken in a limiting sense but is made merely for the purpose of describing the general principles of the invention. It is to be understood that features described in reference to particular embodiments may be combined with features of other particular embodiments. The scope of the invention should be ascertained with reference to the claims. In the description of the invention that follows, like numerals or reference designators will be used to refer to like parts or elements throughout. In addition, the first digit of a reference number (or first two digits of a 4 digit reference number) identifies the drawing in which the reference number first appears.

Pneumostoma Formation and Anatomy

FIG. 1A shows the chest of a patient indicating alternative locations for creating a pneumostoma that may be managed using the system and methods of the present invention. A first pneumostoma 110 is shown on the front of the chest 100 over the right lung 101 (shown in dashed lines). The pneumostoma is preferably positioned over the third intercostal space on the mid-clavicular line. Thus, the pneumostoma 110 is located on the front of the chest between the third and fourth ribs. Although the pneumostoma 110 is preferably located between two ribs, in alternative procedures a pneumostoma can also be prepared using a minithoracotomy with a rib resection.

In FIG. 1A, a second pneumostoma 112 is illustrated in a lateral position entering the left lung 103 (shown in dashed lines). The pneumostoma 112 is preferably positioned over the fourth or fifth intercostal space under the left arm 104. In general, one pneumostoma per lung is created; however, more or less than one pneumostoma per lung may be created depending upon the needs of the patient. In most humans, the lobes of the lung are not completely separate and air may pass between the lobes.

A pneumostoma is surgically created by forming an artificial channel through the chest wall and joining that channel with an opening through the visceral membrane of the lung into parenchymal tissue of the lung to form an anastomosis. The anastomosis is joined and sealed by sealing the channel from the pleural cavity using adhesives, mechanical sealing and/or pleurodesis. Methods for forming the channel, opening, anastomosis and pleurodesis are disclosed in applicants' pending and issued patents and applications including U.S. patent application Ser. No. 10/881,408, now U.S. Pat. No. 7,682,332, entitled "Methods to Accelerate Wound Healing in Thoracic Anastomosis Applications" and U.S. patent application Ser. No. 12/030,006, now U.S. Pat. No. 8,062,315, entitled "Variable Parietal/Visceral Pleural Coupling" which are incorporated herein by reference in their entireties.

Figure 1B:
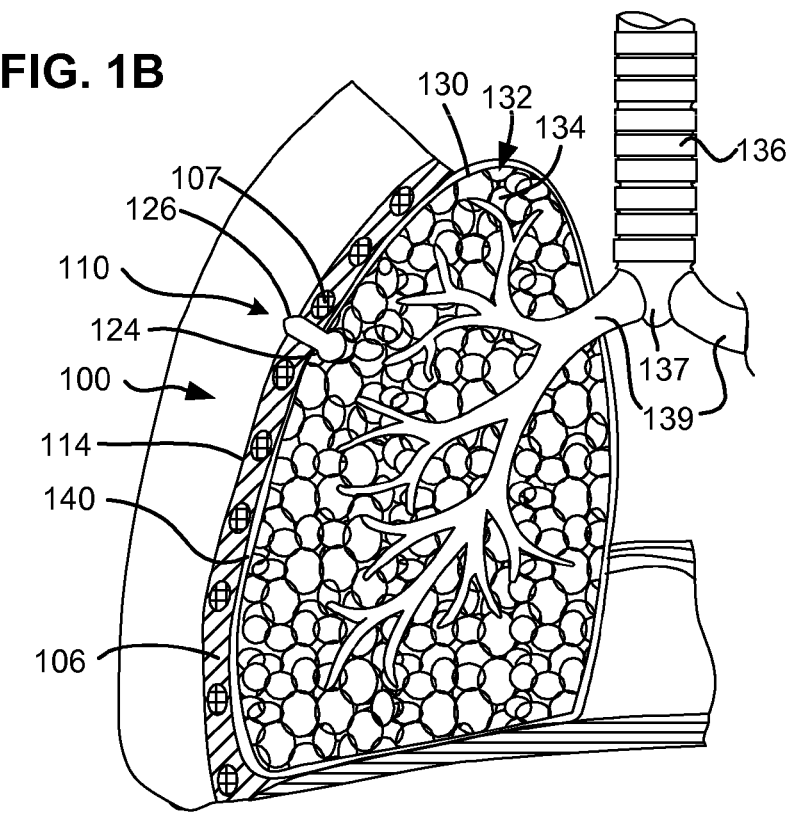
FIG. 1B shows a sectional view of the chest illustrating the relationship between the pneumostoma, lung and natural airways.

FIG. 1B shows a sectional view of chest 100 illustrating the position of the pneumostoma 110. The parenchymal tissue 132 of the lung 130 is comprised principally of alveoli 134. The alveoli 134 are the thin walled air-filled sacs in which gas exchange takes place. Air flows into the lungs through the natural airways including the trachea 136, carina 137, and bronchi 139. Inside the lungs, the bronchi branch into a multiplicity of smaller vessels referred to as bronchioles (not shown). Typically, there are more than one million bronchioles in each lung. Each bronchiole connects a cluster of alveoli to the natural airways. As illustrated in FIG. 1B, pneumostoma 110 comprises a channel through the thoracic wall 106 of the chest 100 between two ribs 107. Pneumostoma 110 opens at an aperture 126 through the skin 114 of chest 100.

Figure 1C:
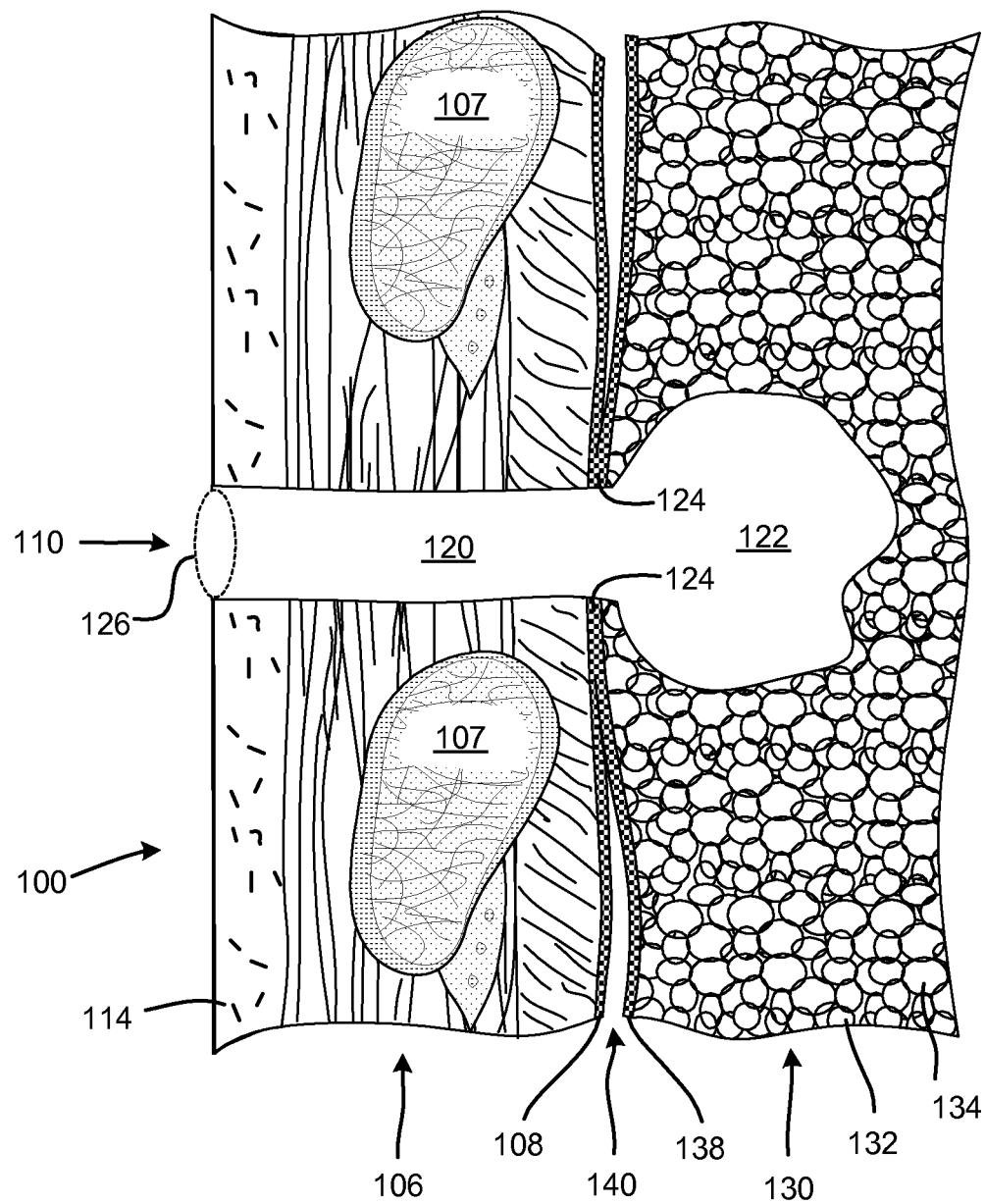
FIG. 1C shows a detailed sectional view of a pneumostoma.

FIG. 1C shows a detailed sectional view of the pneumostoma 110. As illustrated in FIG. 1C, pneumostoma 110 comprises a channel 120 through the thoracic wall 106 of the chest 100 between the ribs 107. The channel 120 is joined to cavity 122 in the parenchymal tissue 132 of lung 130. Although shown having a particular shape, the channel 120 and cavity 122 will typically conform to the shape of a device inserted into the pneumostoma 110. An adhesion or pleurodesis 124 surrounds the channel 120 where it enters the lung 130. The thoracic wall 106 is lined with the parietal membrane 108. The surface of the lung 130 is covered with a continuous sac called the visceral membrane 138. The parietal membrane 108 and visceral membrane 138 are often referred to collectively as the pleural membranes. Between the parietal membrane 108 and visceral membrane 138 is the pleural cavity (pleural space) 140. The pleural cavity usually only contains a thin film of fluid that serves as a lubricant between the lungs and the chest wall. In pleurodesis 124, the pleural membranes are fused and/or adhered to one another eliminating the space between the pleural membranes in that region.

An important feature of the pneumostoma is the seal or adhesion surrounding the channel 120 where it enters the lung 130 which may comprise a pleurodesis 124. A pleurodesis 124 is the fusion or adhesion of the parietal membrane 108 and visceral membrane 138. A pleurodesis may be a complete pleurodesis in which the entire pleural cavity 140 is removed by fusion of the visceral membrane 138 with the parietal membrane 108 over the entire surface of the lung 130. However, as shown in FIG. 1C, the pleurodesis 124 is preferably localized to the region surrounding the channel 120. The pleurodesis 124 surrounding the channel 120 prevents air from entering the pleural cavity 140. If air is permitted to enter pleural cavity 140, a pneumothorax will result and the lung may collapse.

Pleurodesis 124 can be created between the visceral pleura of the lung and the inner wall of the thoracic cavity using chemical methods including introducing into the pleural space irritants such as antibiotics (e.g. Doxycycline or Quinacrine), antivirals (e.g. iodopovidone or silver nitrate), anticancer drugs (e.g. Bleomycin, Mitoxantrone or Cisplatin), cytokines (e.g. interferon alpha-2β and Transforming growth factor-β); pyrogens (e.g. *Corynebacterium parvum*, *Staphylococcus aureus* superantigen or OK432); connective tissue proteins (e.g. fibrin or collagen) and minerals (e.g. talc slurry). A pleurodesis can also be created using surgical methods including pleurectomy. For example, the pleural space may be mechanically abraded during thoracoscopy or thoracotomy. This procedure is called dry abrasion pleurodesis. A pleurodesis may also be created using radiotherapy methods, including radioactive gold or external radiation. These methods cause an inflammatory response and/or fibrosis, healing, and fusion of the pleural membranes. Alternatively, a seal can be created in an acute manner between the pleural membranes using biocompatible glues, meshes or mechanical means such as clamps, staples, clips and/or sutures. The adhesive or mechanical seal may develop into pleurodesis over time. A range of biocompatible glues are available that may be used on the lung, including light-activatable glues, fibrin glues, cyanoacrylates and two part polymerizing glues. Applicants' copending U.S. patent application Ser. No. 12/030,006, now U.S. Pat. No. 8,062,315 entitled "VARIABLE PARIETAL/ VISCERAL PLEURAL COUPLING" discloses methods such as pleurodesis for coupling a channel through the chest wall to the inner volume of the lung without causing a pneumothorax and is incorporated herein by reference for all purposes.

When formed, pneumostoma 110 provides an extra pathway for exhaled air to exit the lung 130 reducing residual volume and intra-thoracic pressure without the air passing through the major natural airways such as the bronchi 139 and trachea 136. Collateral ventilation is particularly prevalent in an emphysemous lung because of the deterioration of lung tissue caused by COPD. Collateral ventilation is the term given to leakage of air through the connective tissue between the alveoli 134. Collateral ventilation may include leakage of air through pathways that include the interalveolar pores of Kohn, bronchiole-alveolar communications of Lambert, and interbronchiolar pathways of Martin. This air typically becomes trapped in the lung and contributes to hyperinflation. In lungs that have been damaged by COPD and emphysema, the resistance to flow in collateral channels (not shown) of the parenchymal tissue 132 is reduced allowing collateral ventilation to increase. Air from alveoli 134 of parenchymal tissue 132 that passes into collateral pathways of lung 130 is collected in cavity 122 of pneumostoma 110. Pneumostoma 110 thus makes use of collateral ventilation to collect air in cavity 122 and vent the air outside the body via channel 120 reducing residual volume and intra-thoracic pressure and bypassing the natural airways which have been impaired by COPD and emphysema.

By providing this ventilation bypass, the pneumostoma allows stale air trapped in the parenchymal tissue 132 to escape from the lung 130. This reduces the residual volume and intra-thoracic pressure. The lower intra-thoracic pressure reduces the dynamic collapse of airways during exhalation. By allowing the airways to remain patent during exhalation, labored breathing (dyspnea) and residual volume (hyperinflation) are both reduced. Pneumostoma 110 not only provides an extra pathway that allows air to exit the lung 130 but also allows more fresh air to be drawn in through the natural airways. This increases the effectiveness of all of the tissues of the lung 130 and improves gas exchange. Increasing the effectiveness of gas exchange allows for increased absorption of oxygen into the bloodstream and also increased removal of carbon dioxide. Reducing the amount of carbon dioxide retained in the lung reduces hypercapnia which also reduces dyspnea. Pneumostoma 110 thus achieves many of the advantages sought by lung volume reduction surgery without surgically removing a portion of the lung or sealing off a portion of the lung.

Applicants have found that pneumostoma management devices in accordance with embodiments of the present invention are desirable to maintain the patency of the pneumostoma and control flow of materials between the exterior of the patient and the parenchymal tissue of the lung via the pneumostoma. The pneumostoma management devices include a pneumostoma vent to enter the pneumostoma and allow gases to exit the lung and may also include a chest mount, and/or one or more of the tools, packaging, auxiliary device and methods described herein. In general terms a pneumostoma management device ("PMD") or pneumostoma vent, comprises a tube which is inserted into the pneumostoma and an external component which is secured to the skin of the patient to keep the tube in place. Gasses escape from the lung through the tube and are vented external to the patient. The pneumostoma management device may, in some, but not all cases, include a filter which only permits gases to enter or exit the tube. The pneumostoma management device may, in some, but not all cases, include a one-way valve which allows gases to exit the lung but not enter the lung through the tube.

Pneumostoma Management Devices

Figure 2A:
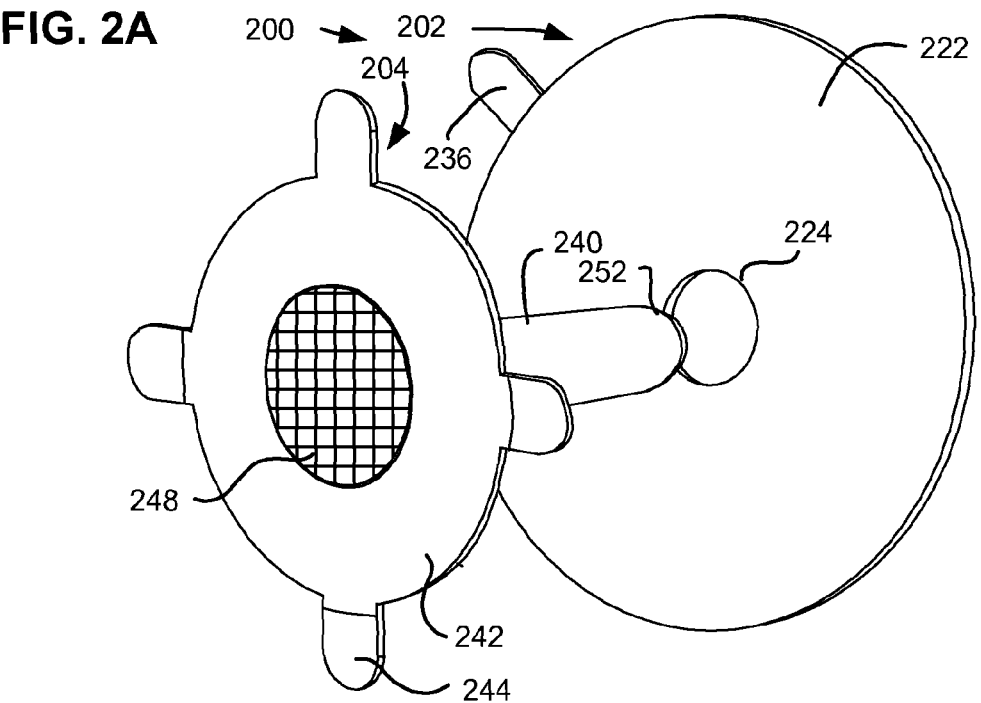
FIG. 2A shows a perspective view of components of a pneumostoma management system according to an embodiment of the present invention.
Figure 2B:
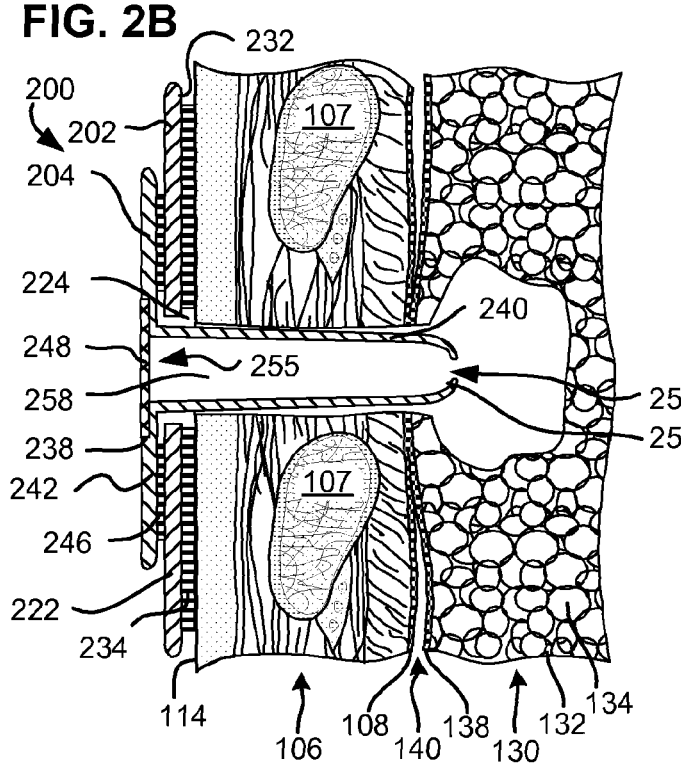
FIG. 2B shows a sectional view of the components of FIG. 2A.

FIGS. 2A and 2B illustrate views of a pneumostoma management device ("PMD") 200 in accordance with an embodiment of the present invention. PMD 200 is designed so as not to interfere with the range of motion or clothing of the patient. This is of importance for a device such as PMD 200 which must be used continuously to be effective. Comfort and ease of use are important if patient compliance with treatment protocols is to be achieved. The low profile of PMD 200 allows it to be inconspicuously positioned on the chest 100 of a patient in either the frontal 110 or lateral 112 locations (See FIG. 1A).

PMD 200 includes a pneumostoma vent 204 which is inserted in a pneumostoma and secured to the chest of the patient. In some embodiments, the PMD is a single piece device in which a pneumostoma vent has a flange which secures the pneumostoma vent directly to the skin of the patient. However, PMD optionally includes a chest mount 202 which may be mounted to the skin of the patient and through which the chest vent 204 may be inserted into the pneumostoma. Where an optional chest mount 202 is utilized, pneumostoma vent 204 is mounted through an aperture 224 in chest mount 202. As will be further described below, the connection between the chest mount 202 and pneumostoma vent 204 may be engineered so as to ensure that pneumostoma vent 204 cannot be over-inserted into the lung.

A patient will typically wear a PMD at all times and thus the materials should meet high standards for biocompatibility. In preferred embodiments, pneumostoma vent 204 is formed from biocompatible/implantable polymers or biocompatible/implantable metals. In preferred embodiments, chest mount 202 is also formed from biocompatible polymers or biocompatible metals. Further description of suitable materials for manufacturing a PMD are provided in the Materials section below.

FIGS. 2A and 2B shows a perspective view of a two-component pneumostoma management device 200 which includes a pneumostoma vent 204 and an optional chest mount 202. Chest mount 202 is mounted to the skin of the patient and pneumostoma vent 204 is fitted to the chest mount 202. Pneumostoma vent 204 is mounted through an aperture 224 in chest mount 202. The chest mount is configured so that pneumostoma vent 204 cannot be over-inserted into the lung and to protect the skin of the chest from irritation. PMD 200 is preferably disposable. Pneumostoma vent 204 will be replaced periodically, such as daily, or when necessary. Chest mount 202 will also be replaced periodically, such as weekly, or when necessary. The patient will also be provided with a supply of chest mounts 202 and pneumostoma vents 204 by a medical practitioner or by prescription. A one week supply of pneumostoma vent 204 (such as seven pneumostoma vents 204) may be conveniently packaged together with one chest mount 202.

Pneumostoma vent 204 includes a tube 240 sized and configured to fit within the channel of a pneumostoma and a flange 242. The aperture 224 in the chest mount is adapted and configured to receive the tube 240 of pneumostoma vent 204. A flange 242 is formed in one piece with, or permanently connected to, the proximal end of tube 240. Flange 242 is sufficiently thin and flexible that it can conform to the surface of the chest mount 202. In typical embodiments, flange 242 is less than about 3 mm in thickness, and in preferred embodiments, disc 222 is less than about 2 mm in thickness. Flange 242 is, however, too large to fit through aperture 224, and, thus, acts as an insertion stop. Flange 242 is shown as a circular disc with a plurality of tabs 244. The distal surface of flange 242 may be covered in whole or in part with a releasable adhesive 246 adapted to temporarily fix flange 242 to the skin of the patient or to the optional chest mount 202.

Tube 240 is stiff enough that it may be inserted into a pneumostoma without collapsing. Over time, a pneumostoma may constrict and it is one function of PMD 200 to preserve the patency of the channel of the pneumostoma by resisting the natural tendency of the pneumostoma to constrict. A crush recoverable material may be incorporated into tube 240 in order to make it crush recoverable. Tube 240 of pneumostoma vent 204 is sufficiently long that it can pass through the thoracic wall and into the cavity of a pneumostoma inside the lung. The length of tube 240 required for a pneumostoma vent 204 varies significantly between different pneumostomas. Because of the variation in pneumostomas, pneumostoma vents 204 are manufactured having tubes 240 in a range of sizes and a patient is provided with a pneumostoma vent 204 having a tube 240 of appropriate length for the patient's pneumostoma. The material and thickness of tube 240 of pneumostoma vent 204 is preferably selected such that tube 240 is soft enough that it will deform rather than cause injury to the pneumostoma or lung.

Tube 240 of pneumostoma vent 204 preferably comprises an atraumatic tip 252 at the distal end as shown in FIGS. 2A and 2B. Tip 252 may be rounded, beveled or curved in order to reduce irritation or damage to the tissues of the pneumostoma or lung during insertion or while in position. Pneumostoma vent 204 has an opening 254 in tip 252 of tube 240. Opening 254 allows the entry of gases from the cavity of the pneumostoma into lumen 258 of tube 240. Tube 240 is optionally provided with one or more side openings (not shown) positioned near tip 252 and/or along the length of tube 240 to facilitate the flow of gas and/or mucous/discharge into lumen 258.

Pneumostoma vent 204 includes a hydrophobic filter 248 over the proximal end of tube 240. Hydrophobic filter 248 is positioned and mounted such that material moving between lumen 258 and the exterior of pneumostoma vent 204 passes through hydrophobic filter 248. Hydrophobic filter 248 may also be selected to prevent the entry of microbes, pollen and other allergens and pathogens into the lumen 258. Hydrophobic filter 248 also prevents the exit of liquid and particulate discharge from lumen 258 to the exterior of pneumostoma vent 204. Hydrophobic filter 248 is preferably designed such that it fits into a recess in flange 242. However, hydrophobic filter 248 is thin and flexible, and, thus, will not protrude far if affixed to the surface of flange 242. Hydrophobic filter 248 may be permanently attached to flange 242, as shown in FIG. 2B. Hydrophobic filter 248 may be permanently attached to flange 242 using a press fitting, permanent adhesive, welding or other bonding technology. Flange 242 of pneumostoma vent 204 is releasably connected to chest mount 202 during use. Hydrophobic filter 248 may be made from a material such as medical grade GORE-TEX® (W. L. Gore & Associates, Inc., Flagstaff, Ariz.) or a reticulated polyurethane-based open cell foam.

Hydrophobic filter 248 serves several purposes. In general, hydrophobic filter 248 controls the passage of solid or liquid material between the lumen 258 and the exterior of flange 242. For example, hydrophobic filter 248 prevents the flow of water into the lumen 258 through proximal opening 255. Thus, a patient using PMD 200 may shower without water entering the lung through the pneumostoma. Hydrophobic filter 248 may also be selected so as to prevent the entry of microbes, pollen and other allergens and pathogens into the lumen 258. Hydrophobic filter 248 also prevents the exit of liquid and particulate discharge from lumen 258 to the exterior of pneumostoma vent 204. This is desirable to prevent contact between liquid and particulate discharge and clothing for example.

Pneumostoma vent 204 may mount directly to the skin of the chest or to an optional chest mount 202 which is secured to the chest of the patient. In one embodiment, illustrated in FIGS. 2A and 2B, chest mount 202 comprises a flange 242 and an aperture 224. Chest mount 202 includes a thin and flexible disc 222 designed to conform to the chest of the patient. Disc 222 is generally circular but is provided with one or more tabs 236 to facilitate application and removal of disc 222 from the skin of the patient. In typical embodiments, disc 222 is less than about 3 mm in thickness, and in preferred embodiments, disc 222 is less than about 2 mm in thickness. However, the disc may be thicker if absorbing requirements of the discharge around the tube is high. Additionally, a thicker disk may provide a forgiving surface to apply the flange 242 to a rough or highly contoured skin surface. Disc 222 is, thus, sufficiently flexible that it can conform to the surface of the chest but is relatively inelastic so that the size and shape of aperture 224 is relatively stable. Disc 222 has a contact surface 232 which contacts the skin of the patient surrounding the pneumostoma and positions the aperture 224 over the opening of the pneumostoma. Contact surface 232 of disc 222 is provided with a biocompatible adhesive 234, such as a hydrocolloid adhesive, for securing disc 222 to the skin of the patient. The adhesive 234 may be protected by a protector sheet that is removed prior to use of disc 222. Adhesive 234 should be selected so as to secure disc 222 to the chest of the patient in the correct position relative to the pneumostoma without causing undue irritation to the skin of the patient. The adhesive need not create an air tight seal between disc 222 and the skin of the patient and indeed, as described above, it may be desirable to allow air to circulate behind disc 222 so that moisture does not accumulate. Moisture may also be allowed to escape by making disc 222 from a porous material or creating pores in the material of disc 222.

The aperture 224 is adapted and configured to receive the pneumostoma vent 204. In a preferred embodiment, the dimensions of aperture 224 are tightly controlled and the size and shape of aperture 224 remains stable even under any reasonably possible application of force to chest mount 202. The size of the aperture limits what components of the system may enter the pneumostoma and prevents components from passing completely into the pneumostoma. All the components of the pneumostoma vent 204 (other than the distal end of tube 240) and chest mount 202 or other tools designed for use by the patient are preferably larger than the aperture 224, thus precluding passage of any component from passing completely through the aperture even in the unlikely event of device failure. These safety features prevent unsafe entry of any of the components of pneumostoma vent 204 into the pneumostoma even in the unlikely event of device failure.

Figure 2C:
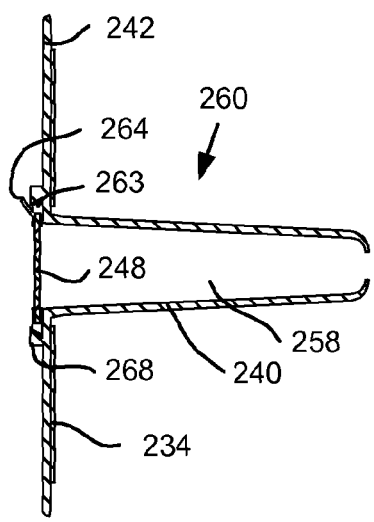
FIG. 2C shows an alternative pneumostoma vent.

In an alternative embodiment shown in FIG. 2C, hydrophobic filter 248 is releasably attached to flange 242 of a pneumostoma vent 260. Hydrophobic filter 248 may, for example, be releasably attached to flange 242 using a joint such as a threaded coupling or snap fitting. As shown in FIG. 2C, a ring 263 surrounding hydrophobic filter 248 snaps into place in a receiver 268 in flange 242. Hydrophobic filter 248 may be removed by pulling on tab 264. Removal of hydrophobic filter 248 allows access to lumen 258 while pneumostoma vent 260 is still positioned in the pneumostoma. This also allows access to the pneumostoma via the tube 240 of pneumostoma vent 260. Access to the pneumostoma may be useful, for example, for suction, irrigation and/or drug delivery. The pneumostoma vent 260 of FIG. 2C may be used with or without the chest mount 202 of FIGS. 2A and 2B.

It is not necessary that a flow-control device be used in a pneumostoma vent to form an airtight seal against the entry of air into the lung through the pneumostoma. Indeed, air may enter the lung through the pneumostoma between removal and reinsertion of the pneumostoma vent 204. The pleurodesis of the pneumostoma prevents the entry of air into the pleural cavity which would otherwise cause pneumothorax. However, it is sometimes desirable to restrict flow of air in through the pneumostoma so as to encourage a reduction in hyperinflation and to preclude the aspiration of solid, liquid or gas into the lung through the pneumostoma. Thus, in alternative embodiments a pneumostoma vent may be provided with a flow control device instead of, or in addition to, the hydrophobic filter 248. The flow-control device may comprise a one-way valve assembly such as a flapper valve, Heimlich valve, reed valve or the like for allowing air to be exhaled with very low resistance through the pneumostoma while restricting the flow of air or other matter into the pneumostoma from outside the body. A suitable flow-control device preferably includes only a small number of components for ease of manufacturing and reliability and should be designed such that it has no small parts which might be aspirated through the pneumostoma.

Figure 3A:
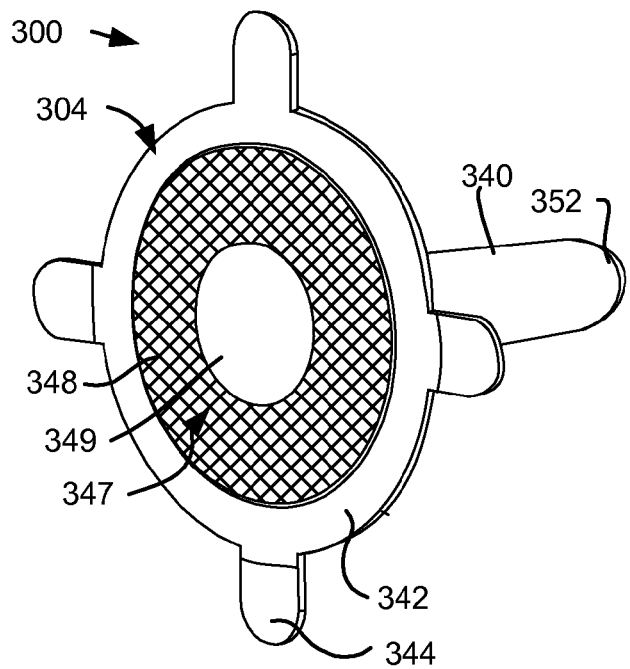
FIGS. 3A-3C show an alternative pneumostoma management device according to an embodiment of the present invention.
Figure 3B:
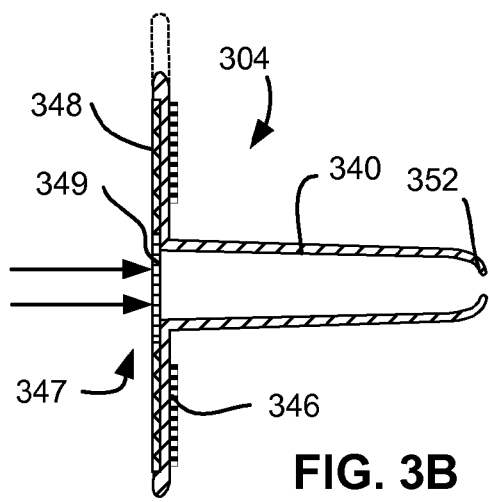
Figure 3C:
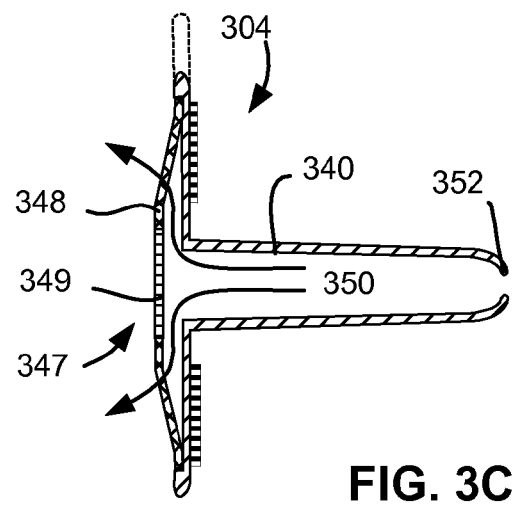

FIGS. 3A-C illustrate an alternative pneumostoma management device 300 having a combination hydrophobic filter and one-way valve. PMD 300 includes a pneumostoma vent 304. Pneumostoma vent 304 includes a tube 340 formed in one piece with a flange 342. Flange 342 is also thin and flexible so that it may conform to the chest of the patient. In typical embodiments, flange 342 is less than about 3 mm in thickness, and in preferred embodiments, flange 342 is less than about 2 mm in thickness. Flange 342 has one or more tabs 344 to facilitate insertion and removal. The distal surface of flange 342 may be covered in whole or in part with a releasable adhesive 346 adapted to temporarily fix flange 342 to the chest of the patient. PMD 300 may optionally include a chest mount such as chest mount 202 of FIG. 2A (not shown in FIG. 3A).

A combination hydrophobic filter and one-way valve 347 is attached to flange 342 over the proximal end of tube 340. Valve 347 includes an annular region 348 of porous hydrophobic material and a central non-porous region 349. Valve 347 is attached to the flange at the circumference. As shown in FIG. 3B, when the pressure outside the pneumostoma is larger than the pressure inside the pneumostoma, valve 347 is pushed against flange 342 and non-porous region 349 blocks the proximal end of tube 340. This prevents entry of gases through the pneumostoma during inhalation or in the event of sudden pressure increases in the environment. As shown in FIG. 3C, when the patient exhales, the increased pressure inside tube 340 pushes valve 347 away from the proximal end 352 of tube 340. Gases can then pass radially out of tube 340 and escape through the porous annular region 348 as shown by arrows 350. Thus valve 347 provides a simple way to provide one-way valve and filter functionality to pneumostoma vent 304. Other arrangements of valves and/or filters may be used in alternative embodiments.

The pneumostoma vents of FIGS. 2A-2C and 3A-3C are designed to be inserted into a pneumostoma and removed from a pneumostoma without the need for special tools. A releasable adhesive or releasable coupling temporarily secures the pneumostoma vent to the chest of the patient (or optional chest mount). One or more tabs allow the pneumostoma vent to be peeled away from the chest of the patient (or optional chest mount) and removed. The tabs should be made sufficiently large that they can be used by the patients. It may additionally be useful to provide an alignment tool for aligning the aperture of the chest mount with the pneumostoma during application of the chest mount to the skin of the chest. It may also be useful to provide a plug which may be used to protect the pneumostoma from the entry of foreign material during times of activities when a pneumostoma vent is not present in the chest mount. The alignment tool and/or pneumostoma plug are designed to engage the chest mount in the same way as the pneumostoma vent, for example, by using a releasable adhesive or other releasable coupling.

Figure 4A:
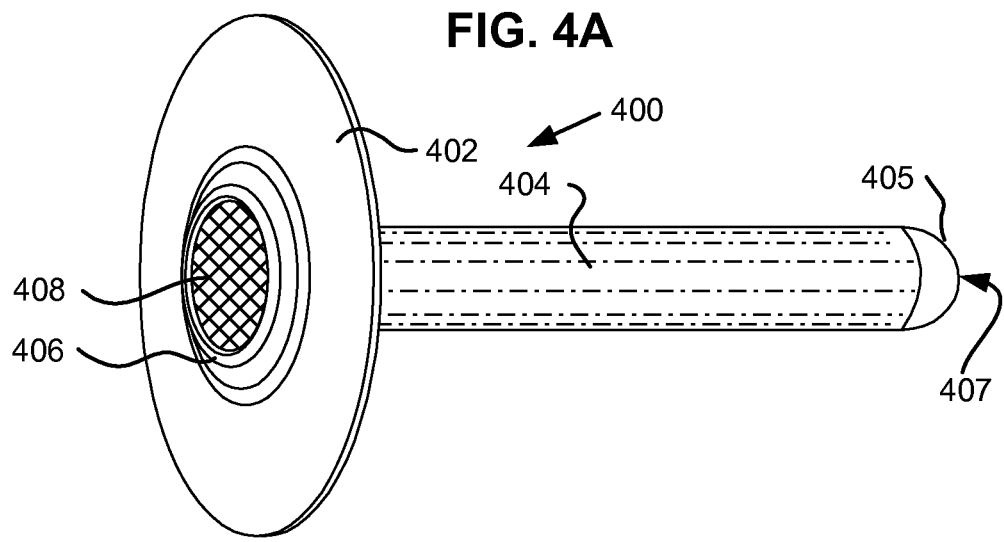
Figure 4B:
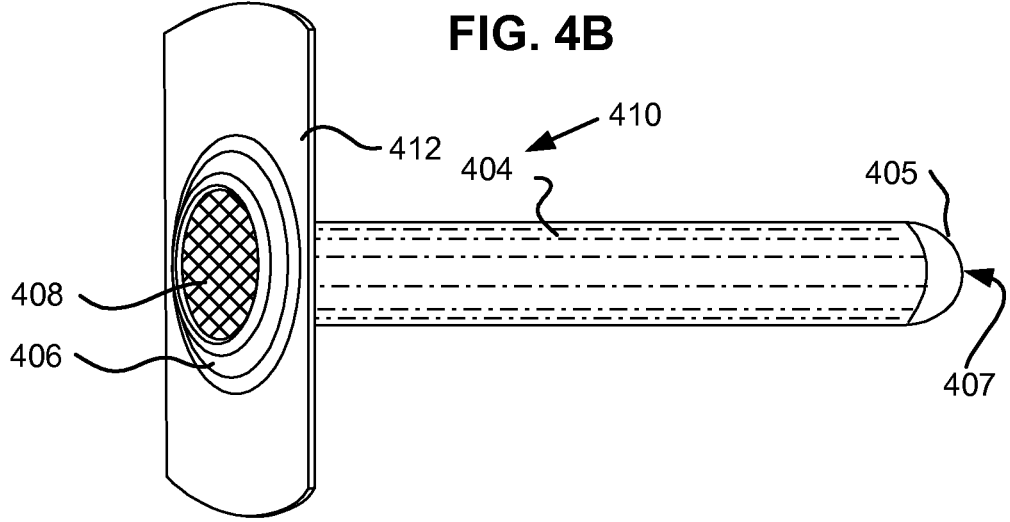
Figure 4C:
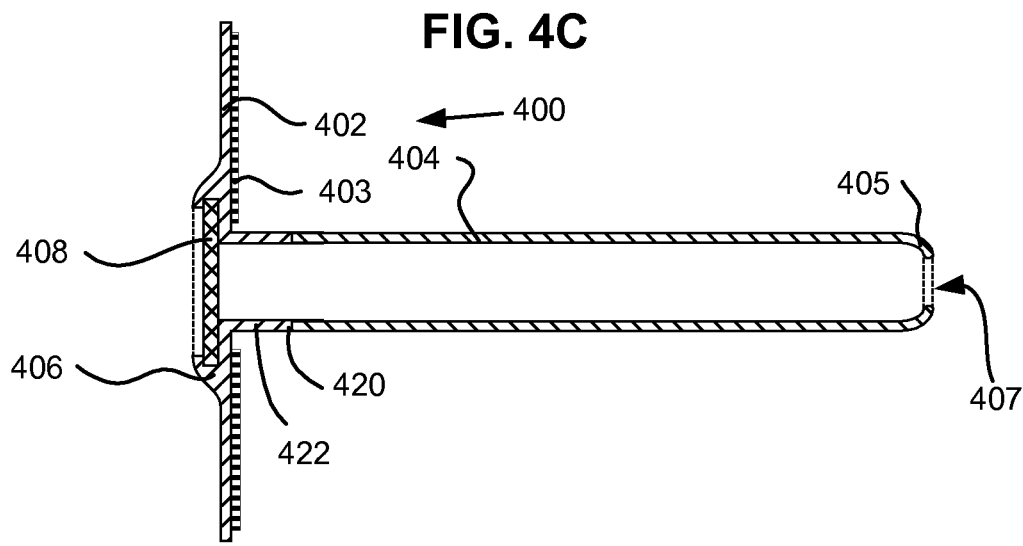

FIGS. 4A-4F show views of alternative designs of pneumostoma vent. As shown in FIG. 4A, pneumostoma vent 400 includes a tube 404 and a flange 402. Flange 402 is thin and flexible so that it may conform to the chest of the patient or an optional chest mount (such as chest mount 202 of FIG. 2A). In typical embodiments, flange 402 is less than about 3 mm in thickness, and in preferred embodiments, flange 402 is less than about 2 mm in thickness. Flange 402 may be provided with one or more tabs (not shown) to facilitate insertion and removal. The distal surface of flange 402 is covered in whole or in part with a releasable adhesive 403 (see FIG. 4C). The adhesive 403 is adapted to temporarily secure flange 402 to the chest of the patient (or chest mount if used). The size, shape and thickness of the flange 402 are selected to facilitate installation and enhance the comfort of the patient during use while maintaining the correct placement of tube 404 in the pneumostoma. Tube 404 has an atraumatic tip 405 and an aperture 407 at the distal end. Flange 402 may be generally circular as shown in FIG. 4A. In the alternative embodiment of FIG. 4B flange 412 of pneumostoma vent 410 is generally strip-shaped or rectangular. A hydrophobic filter 408 is mounted to the flange 402 or 412 over the proximal opening of tube 404. In the embodiments of FIGS. 4A-4C, hydrophobic filter 408 is a thin disc of hydrophobic material which is press fit into a raised region 406 of the flange 402 or 412. The sectional view of the pneumostoma vent 400 of FIG. 4A, shown in FIG. 4C, illustrates one way in which interference between hydrophobic filter 408 and raised region 406 can secure hydrophobic filter 408. In alternative embodiments, a hydrophobic filter may be secured to the flange using adhesive or other bonding methods. Other arrangements of valves and/or filters may be used instead of, or in addition, to the hydrophobic filter shown.

As previously discussed, the length of tube 404 required for a pneumostoma vent 400 or 410 varies significantly between different pneumostomas. Because of the variation in pneumostomas, pneumostoma vents 400 or 410 should be manufactured having tubes 404 in a range of sizes and a patient should be provided with a pneumostoma vent 400 or 410 having a tube 404 of appropriate length for the patient's pneumostoma. Pneumostoma vents 400 or 410 having different lengths of tube 404, may be manufactured in a number of different ways. FIGS. 4C-4F and 5A-5C illustrate designs which facilitate the manufacture of pneumostoma vents having a range of different lengths.

FIG. 4C is a sectional view of pneumostoma vent 400 of FIG. 4A made according to one alternative embodiment. As shown in FIG. 4C, tube 404 is formed as a separate piece from flange 402. Tube 404 is connected at a butt joint 420 to a tubular extension 422 of flange 402. Butt joint 420 may be adhesively bonded, welded or otherwise secured. A single shape of mold/tooling can be used to make all of the flanges 402 for all lengths of the pneumostoma vent 400. Tube 404 can be advantageously formed using an extrusion process. The extruded tube can be cut to any desired length and then tipped to create atraumatic tip 405 around distal aperture 407. Different lengths of tube 404 can be bonded to flange 402 to create a range of different lengths of pneumostoma vent 400 without requiring different tooling for each size of the pneumostoma vent 400. Additionally, a different material may be used to make flange 402 than for tube 404. For example, a softer more conformable material may be used for flange 402 to allow it to conform to the chest of the patient. A harder material may be used for tube 404 to allow it to resist crushing while having a thin wall thickness and consequently a large inner diameter for the passage of air. An adhesive 403 is placed on the distal surface of flange 402 to releasably secure the flange to the chest of the patient (or a chest mount if present).

FIG. 4D is a sectional view of pneumostoma vent 440 made according to another alternative embodiment. As shown in FIG. 4D, tube 444 is again formed as a separate piece from flange 442. A single shape of mold/tooling can again be used to make all of the flanges 442 for all lengths of pneumostoma vent 440. Also, tube 444 can be advantageously formed using an extrusion process. As before, the extruded tube can be cut to any desired length and then tipped to create atraumatic tip 405 around distal aperture 407. Different lengths of tube 444 can be bonded to flange 442 to create a range of different lengths of pneumostoma vent 440 without requiring different tooling for each size of pneumostoma vent 440. Additionally, a different material may be used to make flange 442 than for tube 444. For example a softer more conformable material may be used for flange 442 to allow it to conform to the chest of the patient. A harder material may be used for tube 444 to allow it to resist crushing while having a thin wall thickness and consequently a large inner diameter for the passage of air. In the embodiment of FIG. 4D, a flare 449 is formed at the proximal end of tube 444. Tube 444 is received through aperture 447 in flange 442. However flare 449 is too large to pass through aperture 447, and, therefore, engages the rim 441 around aperture 447. Flare 449 is securely connected to rim 441 of flange 442. Flare 449 may be adhesively bonded, sealed, welded or otherwise secured to rim 441. This design is advantageous in that flare 449 is too large to fit through aperture 447 even if the joint fails between the flare 449 and rim 441. As before, the extruded tube 444 can be cut to any desired length and then tipped to create atraumatic tip 405 around distal aperture 407. Different lengths of tube 444 can be bonded to flange 442 to create a range of different lengths of pneumostoma vent 404 without requiring different tooling for each size of pneumostoma vent 404. A hydrophobic filter 448 is secured within raised region 446 of flange 442 and an adhesive 443 is applied to the distal surface of flange 442 as in previous embodiments.

FIG. 4E is a sectional view of pneumostoma vent 450 made according to another alternative embodiment. As shown in FIG. 4E, tube 454 is again formed as a separate piece from flange 452 for the same advantages previously discussed with respect to FIGS. 4C and 4D. In the embodiment of FIG. 4E, flange 452 is formed with tubular extension 451 having a plurality of ridges 457. Tubular extension 451 functions like a hose barb. The proximal end of tube 454 is pushed over tubular extension 451 and is deformed by ridges 457. The ridges 457 are designed to secure tube 454 to flange 452 without adhesive. However, an adhesive or other bonding technology may be used in addition to the mechanical connection afforded by tubular extension 451. As before, the extruded tube 454 can be cut to any desired length and then tipped to create atraumatic tip 405 around distal aperture 407. Different lengths of tube 454 can be bonded to flange 452 to create a range of different lengths of pneumostoma vent 450 without requiring different tooling for each size of pneumostoma vent 450. A hydrophobic filter 458 is secured within raised region 456 of flange 452 and an adhesive 453 is applied to the distal surface of flange 452 as in previous embodiments.

FIG. 4F is a sectional view of a pneumostoma vent 460 made according to another alternative embodiment. As shown in FIG. 4F, tube 464 is again formed as a separate piece from a flange 462 for the same advantages previously discussed with respect to FIGS. 4C and 4D. In the embodiment of FIG. 4F, flange 462 is a small disc with a raised region 466 for receiving hydrophobic filter disc 468. Flange 462 has a small extension 461 which extends into tube 464. Tube 464 is formed integral with two arms 467, 469 which extend perpendicular to tube 464. The arms 467, 469 are formed by splitting tube 464 in half along a length equal to the length of arms 467, 469. The two parts of tube 464 are then bent perpendicular to tube 464, hot pressed and trimmed to make arms 467, 469. Flange 462 is then bonded to the proximal opening of tube 464 and to arms 467, 469 and serves to hold filter 468 and also to keep arms 467, 469 perpendicular to tube 464. An adhesive or other bonding technology may be used in addition to the mechanical connection afforded by the extension. As before, the extruded tube 464 can be cut to any desired length and then tipped to create atraumatic tip 405 around distal aperture 407. Different lengths of tube 464 can be bonded to flange 462 to create a range of different lengths of pneumostoma vent 460 without requiring different tooling for each size of pneumostoma vent. A hydrophobic filter 468 is secured within raised region 466 of flange 462 and an adhesive 463 is applied to the distal surface of flange 462 as in previous embodiments. Although two arms 467, 469 are shown in FIG. 4F, in alternative embodiments, tube 464 can be split into three, four or more sections to make three, four or more arms. See FIG. 6E for an example with ten arms.

Figure 5A:
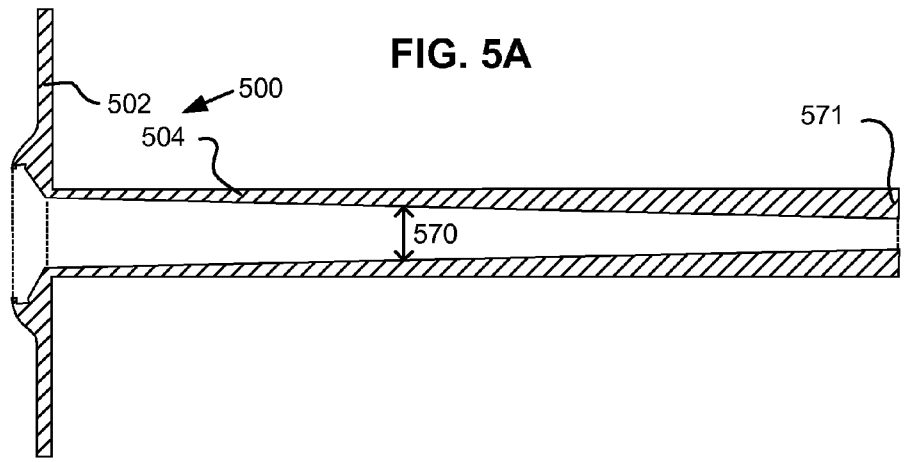
FIGS. 5A-5C show alternative pneumostoma management devices according to embodiments of the present invention.
Figure 5B:
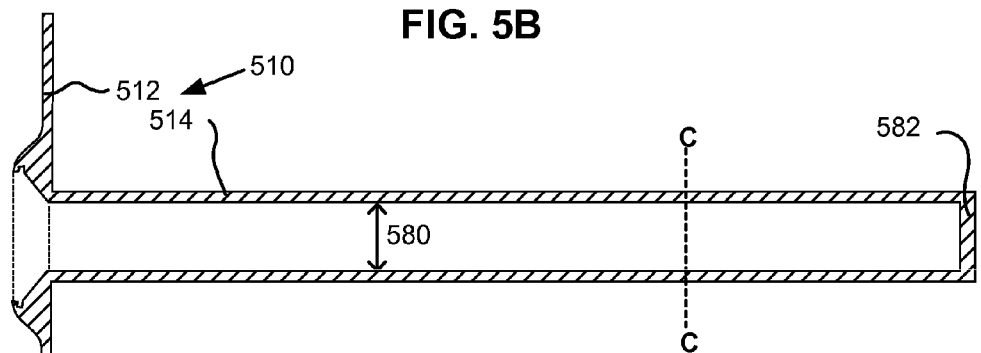
Figure 5C:
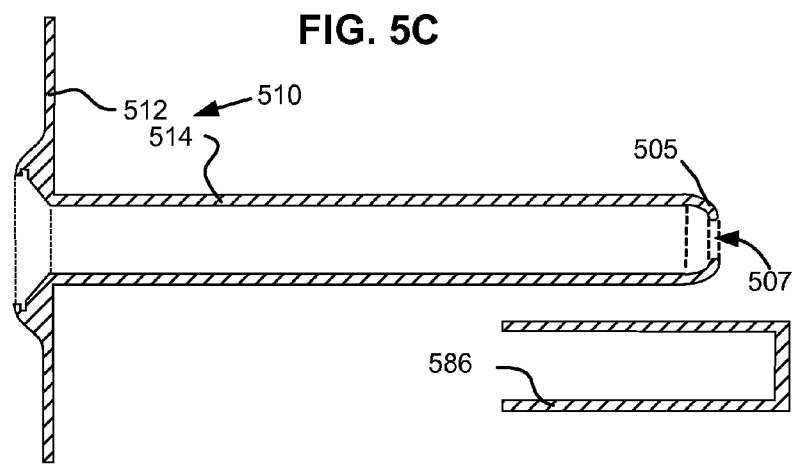

In alternative embodiments, as illustrated in FIGS. 5A-5C, the flange and tube can be formed in one piece. However, it is still advantageous to use a minimum of tooling to make the pneumostoma vent of various sizes. One way to avoid having different molds/tooling for each size of pneumostoma vent is to make all of the pneumostoma vents with the same length of tube. If the tube length is selected to be longer than the longest tube needed for a pneumostoma, then the tube can be trimmed to the desired size and tipped to form the atraumatic tip 505 at the distal end.

FIG. 5A shows one design with an integrated flange 502 and tube 504. Note that the inside diameter 570 of tube 504 reduces in size towards the open distal tip 571. It is desirable to have this draft in the inside diameter 570 of tube 504 to enable the tube 504 to be removed from the pin of the tooling/mold. Thus, tube 504 can be reduced in exterior diameter along its length, or the exterior diameter can be preserved the same and the inner diameter 570 can be reduced as shown. One disadvantage of this design is that the inner diameter 570 may be significantly reduced for long lengths of tube 504. It is preferred, where possible, that the inner diameter 570 be as large as possible, especially for longer tubes 504 so that air and discharge may more easily pass along the tube 504.

After the integrated flange 502 and tube 504 has been removed from the tooling/mold, the tube 504 can be trimmed to the desired length. The cut end of tube 504 can then be tipped to form the atraumatic tip 505 around the aperture 507 at the distal end of the finished tube 504. The pneumostoma vent 500 may be completed by adding the other components, for example a hydrocolloid adhesive and hydrophobic filter.

FIGS. 5B and 5C show an alternative design of pneumostoma vent 510 featuring an integrated flange 512 and tube 514. Note that in this design, tube 514 is initially closed at the distal end 582. Because tube 514 is closed when molded it may be blown off the pin of the mold/tooling occupying the interior of tube 514 using compressed air. This design allows tube 514 to be removed from the tooling/mold without any draft (reduction in inner diameter 580). This design is advantageous as it allows the inner diameter 580 of tube 514 to be kept constant along the length of tube 514. After the integrated flange 512 and tube 514 have been removed from the tooling/mold, the tube 514 can be trimmed to the desired length, for example, along line C-C. The cut end of tube 514 can then be tipped to form the atraumatic tip 505 around the aperture 507 at the distal end of the finished tube 514, as shown in FIG. 5C. FIG. 5C shows tube 514 cut to length and tipped. The closed portion 586 of tube 514 has been cut off and may now be recycled or discarded. The pneumostoma vent 510 may be completed by adding the other components, for example, a hydrocolloid adhesive and hydrophobic filter.

FIGS. 6A-6C shows different views of a pneumostoma vent system 600. Pneumostoma vent system 600 is designed for use without a chest mount although it could be adapted for use with a chest mount. FIG. 6A shows an exploded view of the four main components of pneumostoma vent system. From right to left these components are annular adhesive cover 602, filter 604, pneumostoma vent 606 and hydrocolloid ring 608.

Annular adhesive cover 602 is a thin porous biocompatible membrane which has adhesive on the surface facing the pneumostoma (the inner surface see 622 in FIG. 6C) and non-adhesive on the outer surface 620. A suitable material for annular adhesive cover 602 is a CHG Chlorhexidine Gluconate IV Securement Dressing available under the Tradename TEGADERM® from 3M of St. Paul, Minn. TEGADERM® is a thin layer of polyurethane bonded to a thin hydrocolloid adhesive layer. The film is biocompatible as well as thin, strong, and breathable. Other thin biocompatible dressings and adhesive films may be used as an alternative to TEGADERM® Annular cover 602 has an aperture 624 large enough to allow air to exit through filter 604. Aperture 624 may, however, be slightly smaller than filter 604 so that annular cover 602 can be used to secure filter 604 to pneumostoma vent 606. Exposed portions of annular adhesive cover 602 are provided with a paper cover to protect the adhesive ring prior to use.

Filter 604 is a circular disc of filter material. Filter 604 is preferably a hydrophobic filter material such as, for example, GORE-TEX®. Filter 604 is larger than the proximal aperture in pneumostoma vent 606 and is positioned over the proximal aperture to filter material moving in and out of the pneumostoma vent 606. Filter 604 may be secured to pneumostoma vent 606 by an adhesive, welding, or other bonding technology. Filter 604 may also be secured to pneumostoma vent 606 by annular adhesive cover 602 instead of or in addition to other bonding techniques.

Pneumostoma vent 606 comprises a tube 660 for entering the pneumostoma. As previously discussed, tube 660 has an atraumatic tip 665 and one or more apertures 667 in the distal end to allow gases and discharge to enter tube 660 from the pneumostoma. Tube 660 is connected to a flange 662 at the proximal end. Flange 662 may be formed in one piece with tube 660 or formed separately and joined to tube 660 as previously described with respect to other embodiments. Filter 604 is secured over proximal opening 663 as described in the previous paragraph. The proximal opening 663 of pneumostoma vent 606 is sized so that filter 604 covers proximal opening 663.

Hydrocolloid ring 608 is a biocompatible hydrocolloid material which is naturally sticky like an adhesive on both sides. Hydrocolloid ring may be provided with a film coating and a transitional adhesive on the side facing flange 662 and annular cover 602 in order to better secure hydrocolloid ring 608 to the flange and annular cover. Hydrocolloid ring 608 is preferably less than 3 mm thick, and, is more preferably, approximately 1 mm in thickness. However, the hydrocolloid ring may be thicker if absorbing requirements of the discharge around the tube is high. Additionally, a thicker ring of hydrocolloid may provide a forgiving surface to secure pneumostoma vent system 600 to a rough or highly contoured skin surface. Exposed portions of hydrocolloid ring 608 are provided with a paper cover to protect the adhesive ring prior to use.

Pneumostoma vent system 600 may be provided as a kit of separate components or one or more of the components may be preassembled when provided to the patient. FIG. 6B shows an assembly of all four main components including annular adhesive cover 602, filter 604, pneumostoma vent 606 and hydrocolloid ring 608. Note that tube 660 fits through the middle of hydrocolloid ring 608. Note also that flange 662 is trapped between annular adhesive cover 602 and hydrocolloid ring 608. In this embodiment, filter 604 is also secured to pneumostoma vent 606 by annular adhesive cover 602. Exposed adhesive regions of annular adhesive cover 602 and hydrocolloid ring 608 on the patient side of the pneumostoma vent system assembly 600 are provided with protective covers (for example, paper covers) to protect the adhesive during shipping and prior to use. The completed or partially completed assembly is provided as a sterile product to the patient or caregiver who inserts the pneumostoma vent into a pneumostoma as part of a pneumostoma care program.

FIG. 6C shows the pneumostoma vent system 600 in position within a pneumostoma 110. As shown in FIG. 6C, tube 660 is inserted into the pneumostoma and passes through the chest wall into the lung. Aperture 667 in the distal end of tube 660 is positioned inside the lung so that gases and discharge may enter the tube 660 of the pneumostoma vent system. Flange 662 of pneumostoma vent 606 is secured to the skin of the patient by hydrocolloid ring 608 and annular adhesive cover 602. Flange 662 secures the position of tube 660 within pneumostoma 110. Flange 662 secures the position of aperture 663 on the chest of the patient such that gases from the lung may vent through tube 660 and filter 604. Both hydrocolloid ring 608 and annular adhesive cover 602 contact the skin 114 of the patient to secure the pneumostoma vent system. In some cases a barrier film may be applied by the patient prior to securing the pneumostoma vent system to reduce skin irritation caused by application and removal of the system. An additional ring of absorbent material (not shown), for example, gauze or another absorbent fabric may be positioned around tube 660 between hydrocolloid ring 608 and the skin 114 of the patient for absorbing any discharge from pneumostoma 110 which escapes around tube 660.

As shown in FIG. 6D a pneumostoma vent system 620 may be provided in a number of shapes and sizes to suit the needs and anatomy or different patients. In pneumostoma vent system 620, adhesive cover 622 is generally rectangular or strip-like in shape with an aperture 623 through which filter 624 is exposed. Hydrocolloid ring 628 is oval in shape so that it fits within the coverage of adhesive cover 622. Assembly of pneumostoma vent system 620 is essentially as described with respect to pneumostoma vent system 600. Filter 624 is sandwiched between pneumostoma vent 626 and adhesive cover 622. Tube 625 of pneumostoma vent 626 passes through the middle of hydrocolloid ring 628. Flange 627 of pneumostoma vent 626 is sandwiched between hydrocolloid ring 628 and adhesive cover 622. A protective backing is added to protect the exposed adhesive surfaces prior to application to the patient.

In the alternative embodiment of FIG. 6E, pneumostoma vent 636, of pneumostoma vent system 630, has a flange which comprises ten arms 637. The arms 637 may be made, for example, by splitting the proximal end of tube 635 into slices which are then bent perpendicular to tube 635. The arms 637 may be sandwiched between hydrocolloid ring 638 and adhesive cover 632 as before. Alternatively, the arms 637 may be distributed and embedded within a hydrocolloid layer.

As before, adhesive cover 632 secures filter 634 over the proximal opening in tube 635.

FIG. 6F shows an alternative kit 680 in which a smaller cover 682, filter 604, pneumostoma vent 606 and hydrocolloid ring 608 are preassembled and provided together with a secondary cover 690. In this embodiment, cover 682 is approximately the same size as hydrocolloid ring 608, and, thus, does not contact the skin of the patient but serves only to secure filter 604 and flange 662. Note that tube 660 extends through hydrocolloid ring 608. Flange 662 and filter 604 are trapped and secured between smaller cover 682 and hydrocolloid ring 608. Exposed adhesive regions of hydrocolloid ring 608 on the patient side of the pneumostoma vent system 680 are provided with protective covers (for example, paper covers) to protect the adhesive during shipping and prior to use. The two components are provided as a sterile kit to the patient or caregiver. The pneumostoma vent is first secured in the pneumostoma. The secondary cover is applied over the top of the pneumostoma vent. The secondary cover 690 is designed not to block the flow of air through filter 604. Secondary cover 690 is either sufficiently porous to allow air to pass or is provided with one or more openings to allow air to pass.

In order to increase air flow through the filter a filter material with low to extremely low resistance to air flow is preferred. The resistance of the filter to air flow may be reduced by increasing the area of the air filter through which air may pass. The surface area of the filter may be increased in several ways. First, the filter area may be increased by flaring out the proximal aperture in the pneumostoma vent and consequently a larger filter 604. Second, the filter can be folded, shaped or pleated, increasing the area of filter material for a given aperture. Third, as shown in FIG. 3C, the filter can be arranged such that a filter is larger than the aperture may be utilized. FIG. 6G shows an alternate pneumostoma vent system 600g having a flare 640 in the proximal end of pneumostoma vent 606g. As shown in FIG. 6G, the flare 640 increases the diameter of the proximal opening 663 of pneumostoma vent 606g by approximately 50%. As a consequence, the area of proximal opening 663 and filter 604g, through which gases may escape, is approximately doubled compared to the pneumostoma vent system 600 with a non-flared pneumostoma vent 606 (see FIG. 6C).

FIG. 6H shows an alternate pneumostoma vent system 600h having a conical filter 604h received within pneumostoma vent 606. Conical filter 604h presents approximately four times the surface area for air flow as compared to the flat circular filter 604 of pneumostoma vent system 600 with the same diameter of proximal opening 663 (see FIG. 6C). FIG. 6I shows a perspective view of conical filter 604h. As shown in FIG. 6J, the surface area of filter 604j is increased even further by inclusion of numerous folds/pleats 650 in the material of filter 604j. These techniques for increasing the area of the filter may be used alone, or in combination, in any of the pneumostoma management devices disclosed herein.

The components of the pneumostoma management system are preferably supplied to the patient in sterile packaging. In preferred embodiments, the components are supplied in packaging that assists the patient in utilizing the components of the system in the correct sequence. The packaging should include instructions for use. The packaging may also be printed with material that assists the patient in the appropriate sequence of the steps for using the enclosed components. The package may also be designed to provide the components to the patient in the order required for use and maintain sterility during use. For example, the package may be designed so that, upon opening the package, the components are physically arranged in a tray in the order in which they are to be used by the patient. Alternatively, the components may be provided as individual components separately packaged. For example, cleaning and moisturizing swabs and barrier spray/cream may alternatively or additionally be packaged separately and provided to patient. The insertion tool, removal tool and pneumostoma vent may also be separately packaged.

Use of Pneumostoma Management Devices

The pneumostoma management system is designed such that the system may be used by a patient in a sterile manner. After creating and healing of the pneumostoma the patient will be responsible for applying and removing the PMD and components thereof such as the pneumostoma vent 204 and chest mount 202 (if used). The patient will typically exchange one pneumostoma vent 204 for another and dispose of the used pneumostoma vent 204. Pneumostoma vent 204 will be replaced periodically, such as daily, or when necessary. The patient will be provided with a supply of pneumostoma vents 204 by a medical practitioner or by prescription. To avoid irritation to the chest, it is preferable that the chest mount, if provided, be changed less frequently than the pneumostoma vent. In a preferred embodiment, the chest mount remains attached for up to a week thereby avoiding irritation of the skin caused by daily attachment and removal of a mount. Chest mount 202 will be replaced periodically, such as weekly, or when necessary. The patient will also be provided with a supply of chest mount 202 by a medical practitioner or by prescription. A one week supply of pneumostoma vent 204 (such as seven pneumostoma vents 204) may be conveniently packaged together with one chest mount 202. Where a chest mount is not used, a barrier cream or spray may be used to protect the skin of the chest from irritation.

To use PMD 200, chest mount 202 is first positioned over a pneumostoma and secured with adhesive to the skin of the patient. Chest mount 202 may be positioned by the patient by manual alignment of the aperture 224 of chest mount 202 with the aperture of the pneumostoma. In one embodiment, the chest mount 202 may be aligned with the pneumostoma 110 using a pneumostoma vent 204 assembled with the chest mount 202. The chest mount 202 may be provided to the patient with the pneumostoma vent 204 as one assembly. Alternatively, the patient may insert the pneumostoma vent 204 into the chest mount 202 prior to applying chest mount 202 to the chest. The patient then manipulates the chest mount by the tabs 236. The patient places the tip 252 of pneumostoma vent 204 into the aperture 224 of the pneumostoma 110 and pushes the pneumostoma vent 204 gently and slowly into the pneumostoma 110. During insertion, the patient lets the pneumostoma vent 204 align itself with the channel 120 of the pneumostoma 110 such that when the chest mount 202 contacts and adheres to the skin 114 of the chest 100, the aperture 224 of the chest mount 202 is perfectly aligned with the aperture 224 of the pneumostoma 110. A pneumostoma vent 204 may be inserted in the same way without a chest mount 202 if the particular PMD used does not come with a chest mount 202.

FIG. 7A provides a set of instructions for use (IFU) 720 for replacement of a chest mount according to an embodiment of the invention. At step 722, the patient obtains the replacement chest mount and verifies that it is the correct size for his/her pneumostoma. At step 724, the patient removes the prior chest mount and disposes of it as appropriate. At step 726, the patient removes a sterile cleaning swab from the chest mount package. At step 728, the patient cleans the area of the skin around the pneumostoma. The patient cleans in a direction radially out from the pneumostoma. At step 730, the patient inspects the tissue around the pneumostoma and the pneumostoma for inflammation or injury. If injury or inflammation is observed the patient should seek medical advice.

At step 732, the patient removes a new disposable (or sterilized reusable) chest mount from its packaging. At step 734, the patient removes the backing from the adhesive pad of the chest mount. Care is taken during steps 732 and 734 to handle the chest mount only by the tabs and not to touch the surface which will be in contact with the pneumostoma. At step 736, the patient applies the chest mount to the pneumostoma aligning the aperture of the chest mount with the aperture of the pneumostoma. The chest mount may be packaged with an alignment tool or assembled with a pneumostoma vent to assist in positioning the chest mount correctly. If pain or injury is perceived during application the patient should seek medical advice. The steps of IFU 720 may also be performed by a caregiver or medical practitioner.

Figure 7B:
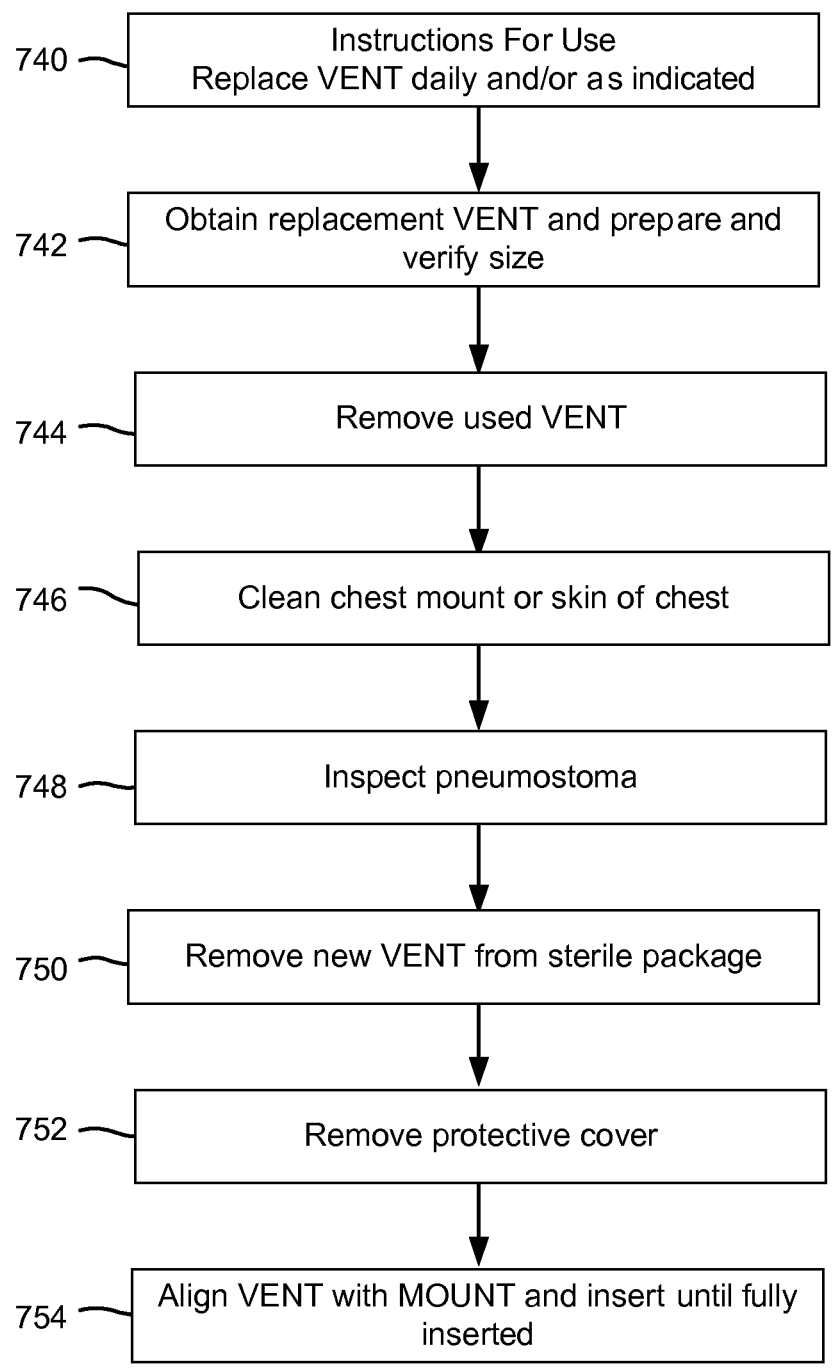

FIG. 7B provides a set of instructions for use (IFU) 740 for replacement of a pneumostoma vent according to an embodiment of the invention. At step 742, the patient obtains the replacement pneumostoma vent and verifies that it is the correct size for his/her pneumostoma. The packaging of the pneumostoma vent is clearly marked with the length of the pneumostoma vent. In addition, the pneumostoma vent can be color coded either on the cap or tube such that a particular color indicates a particular length of pneumostoma vent. At step 744, the patient removes the used pneumostoma vent by pulling on the flange or tabs. The patient cleans or disposes of the used pneumostoma vent as appropriate. At step 746, the patient removes a sterile cleaning swab from the chest mount package and cleans the chest mount or the area of the skin around the pneumostoma if no chest mount is used. The patient cleans in a direction radially out from the pneumostoma. At step 748 the patient inspects the tissue around the pneumostoma and the pneumostoma for inflammation or injury. If injury or inflammation is observed the patient should seek medical advice.

At step 750, the patient removes a new pneumostoma vent from the packaging. The patient does not directly touch the tube of the pneumostoma vent. Patient grips the flange or tabs of the new pneumostoma vent. At step 752, the patient removes the protective covering on the back of the pneumostoma vent exposing the adhesive. At step 754, the patient aligns the tip of the tube of the new pneumostoma vent with the pneumostoma and inserts the tube until the flange is in contact with the chest of the patient or the chest mount. Care is taken during steps 750, 752 and 754 to handle the pneumostoma vent only by the tabs and/or flange and not to touch the sterile tube of the pneumostoma vent. If pain or injury is perceived during insertion of pneumostoma vent the patient should seek medical advice. The steps of IFU 740 may also be performed by a caregiver or medical practitioner.

Accessories for Pneumostoma Management Devices

Figure 8A:
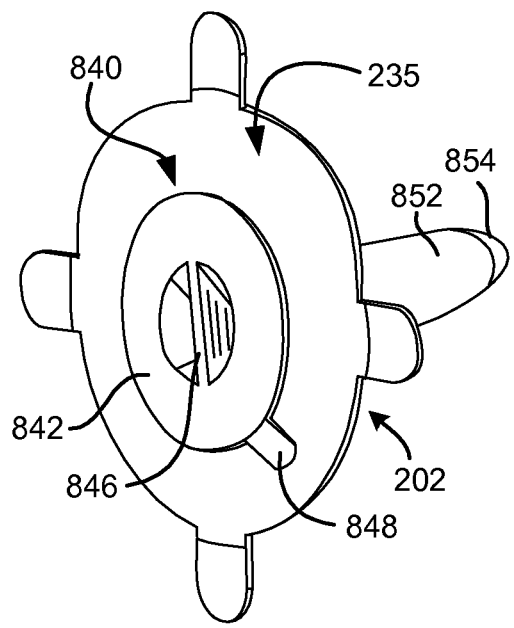
FIGS. 8A-8D show plugs for pneumostoma management devices according to embodiments of the present invention.
Figure 8B:
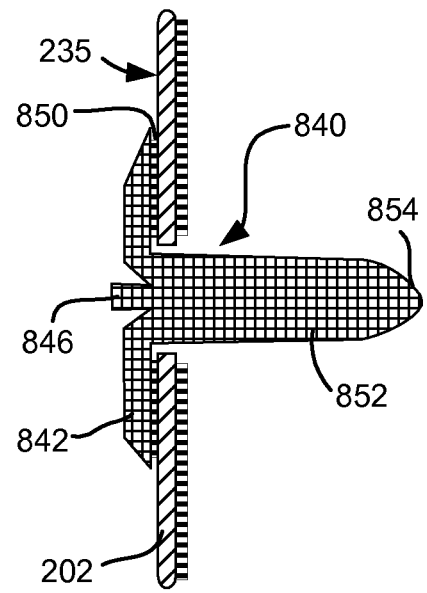

FIGS. 8A and 8B shows views of a pneumostoma plug 840 which may be used to protect the pneumostoma from the entry of foreign material during times or activities when a pneumostoma vent is not present in the pneumostoma or when it is necessary or desirable to close the pneumostoma for activities such as, for example, spirometry testing of lung function or swimming. As shown in FIG. 8A, pneumostoma plug 840 includes a cover 842 for covering the external aperture in the chest or chest mount 202. The cover 842 preferably conforms to the outside surface 235 of chest mount 202 or chest to form a functional seal of the aperture. If the exterior surface of cover 842 is subjected to increased pressure such as by water pressure when swimming, cover 842 is pushed into better contact with surface 235 making a better seal and precluding the entry of water. Pneumostoma plug 840 has a recessed handle 846 or similar gripping mechanism to allow plug 840 to be grasped by the patient and removed when necessary. One or more tabs 848 may be provided on the periphery of cover 842 to allow the cover to be grasped by the patient to remove pneumostoma plug 840. Tabs 848 may be provided instead of, or addition to, handle 846. Plug 840 is however preferably low profile so as to avoid being caught and removed accidentally during an activity. Cover 842 is coated on one side with a releasable adhesive 850 (shown in FIG. 8B) to secure the cover to the chest mount or chest of the patient. Adhesive 850 ensures that pneumostoma plug 840 stays in place and remains there until removed by the patient. Note that cover 842 and the chest mount engagement section 202 are large enough to preclude pneumostoma plug 840 from passing through the pneumostoma.

Referring again to FIGS. 8A and 8B, pneumostoma plug 840 includes a stopple 852 sized and configured to pass into the pneumostoma (and pass through the aperture of the chest mount if present) and to fill the pneumostoma tightly so as to prevent the entry or exit of material through the pneumostoma. Stopple 852 preferably has an atraumatic tip 854 which is soft, and/or curved to facilitate insertion of stopple 852 and reduce irritation to the pneumostoma. Note that stopple 852 may be relatively short compared to a pneumostoma vent such that stopple 852 preferably does not penetrate beyond the end of the channel of pneumostoma. Stopple 852 may, alternatively, be as long as the pneumostoma vent the patient typically uses. Stopple 852 is preferably designed so as to preclude contact of stopple 852 with lung parenchymal tissue during vigorous activity. The surface of stopple 852 may also be provided with surface features such as ridges (not shown) to make a better seal of the pneumostoma. Pneumostoma plug 840 may be designed for use with or without a chest mount 202.

Figure 8C:
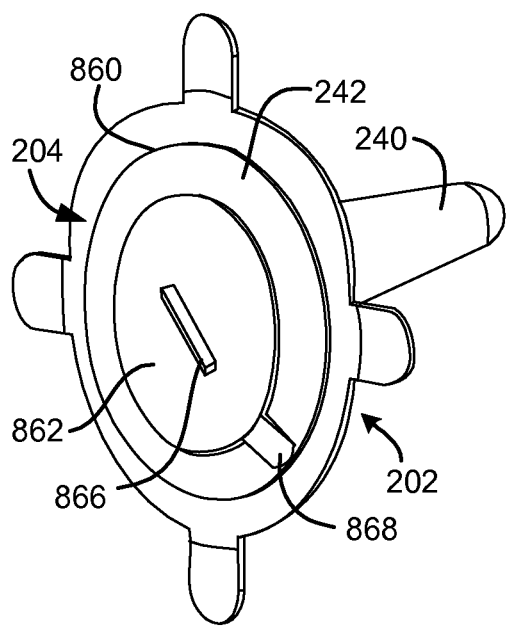
Figure 8D:
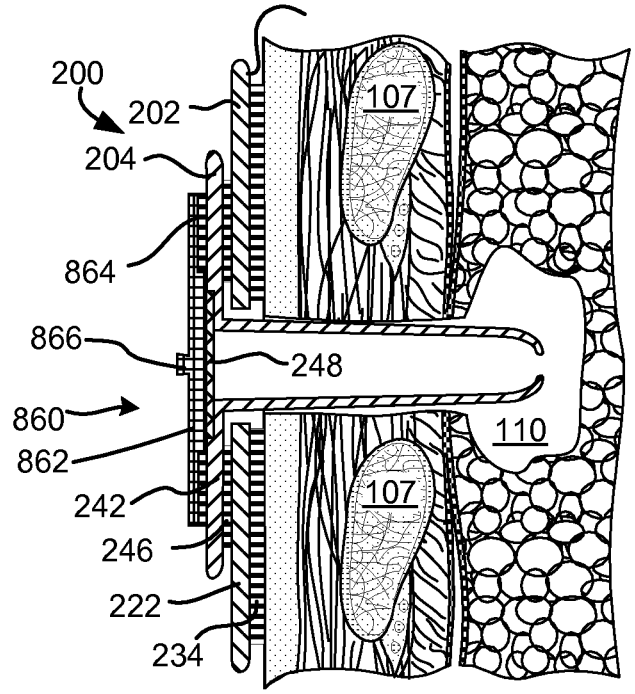

FIGS. 8C and 8D illustrate an alternative pneumostoma plug 860 designed to operate in conjunction with a pneumostoma vent 204. Pneumostoma plug 860 comprises a cover 862 designed to engage the flange 242 of pneumostoma vent 204 (it may also engage chest mount 202 if present). Note that pneumostoma plug 860 is designed such that it will not fit through the aperture of chest mount 202, if present, and will not fit entirely into the pneumostoma. Pneumostoma plug 860 is provided with a ring of releasable adhesive 864 to secure it to the top of pneumostoma vent 204. Adhesive 864 is preferably positioned so as not to contact filter 248. Pneumostoma plug 860 is also provided with a handle 866 and/or tab 868 to facilitate application and removal of pneumostoma plug 860. Pneumostoma plug 860 is designed to cover, obstruct and protect hydrophobic filter 248 to prevent material entering or exiting tube 240 during use. Unlike the pneumostoma plug 840 of FIGS. 8A-8B, pneumostoma plug 860 does not include a stopple 852. During use of plug 860 of FIGS. 8C and 8D, the channel of a pneumostoma 110 will contain the tube 240 of pneumostoma vent 204 as shown in FIG. 8D. Pneumostoma plug 860 is non-porous and may be used to temporarily cover and/or seal a pneumostoma vent 204 during brief activities such as e.g. spirometry testing, showering or working in a dirty environment to prevent entry of material into the pneumostoma or exit of material from the pneumostoma. Note the pneumostoma plug 860 may be used with a pneumostoma vent 204 even where no chest mount 202 is used.

Alternative Features and Embodiments

Figure 9A:
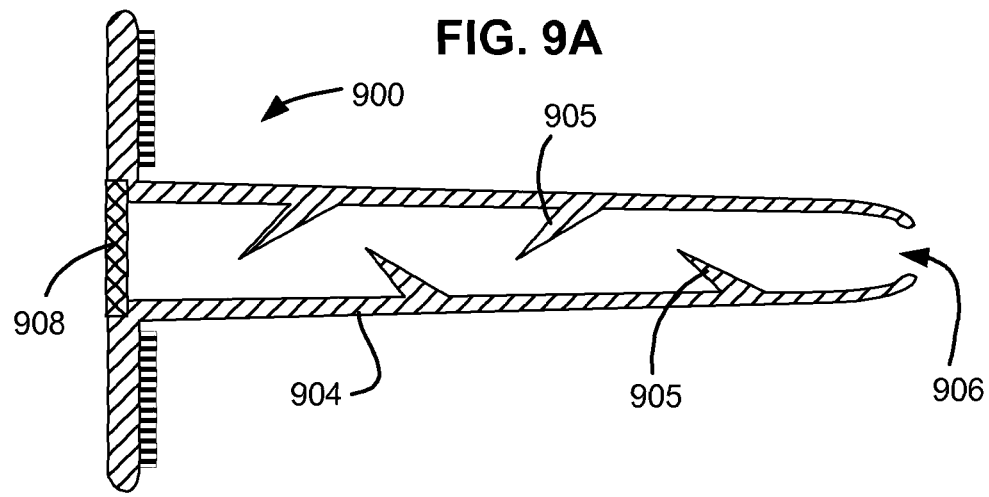

FIGS. 9A-9H show views of alternative designs of pneumostoma vent. FIG. 9A shows an alternative pneumostoma vent 900 which has features within tube 904 designed to encourage migration of discharge (for example, mucus and sputum) out of the lung and prevent it from re-entering the lung. These features may include baffles that preferentially allow discharge to travel along and out of the inner lumen of the tube. As shown in FIG. 9A, the interior surface of tube 904 is covered with an array of baffles 905 which point away from the aperture 906 in the distal end of tube 904. Discharge that enters tube 904 through aperture 906 is pushed towards filter 908 by air flow during exhalation. When the patient inhales, some air may enter through filter 908, however, the discharge is inhibited from traveling back towards aperture 906 by the shape of the baffles 905. Thus, discharge is collected in tube 904. The discharge is removed and disposed of when pneumostoma vent 900 is replaced.

Figure 9B:
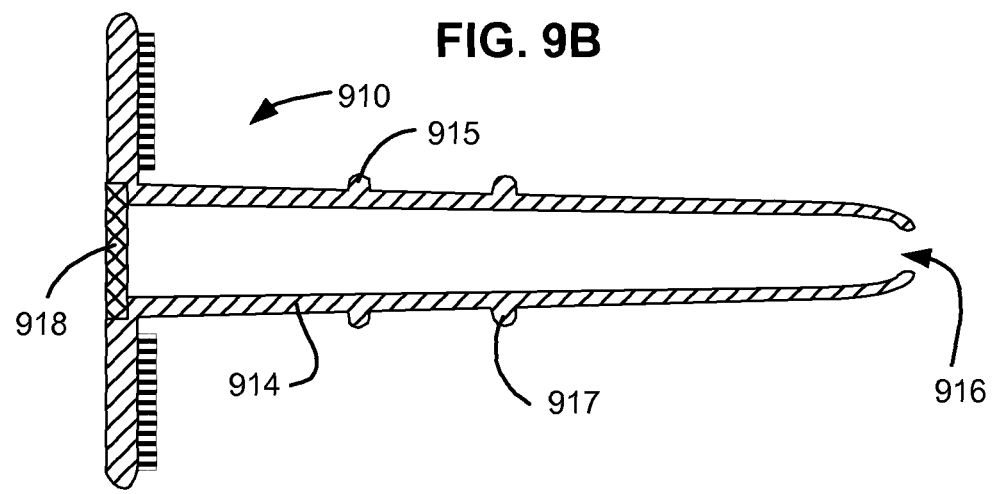

FIG. 9B shows a pneumostoma vent 910 having external features on the surface of tube 914. External features such as rings or ridges may be utilized on a pneumostoma vent to make a better seal between the exterior of the pneumostoma vent and the interior of the channel of the pneumostoma. FIG. 9B shows a sectional view through two rings 915, 917 around the exterior surface of tube 914. These rings engage the channel of the pneumostoma to make a better seal. The rings 915, 917 serve to prevent leakage of mucus and discharge around tube 914. The rings 915, 917 also reduce the possibility of the entry of any materials into the pneumostoma other than through filter 918 and aperture 916.

Figure 9C:
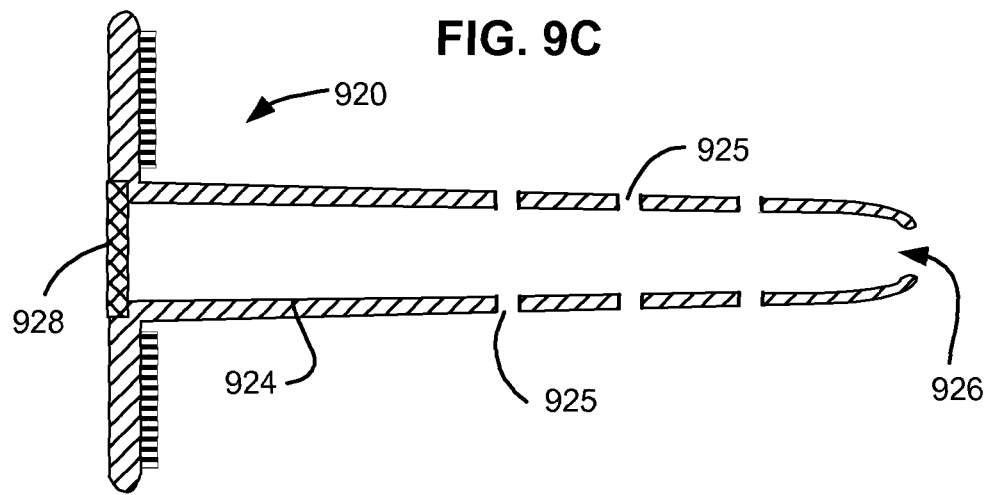

FIG. 9C shows an alternative pneumostoma vent 920 which has a plurality of side apertures 925 in order to facilitate entry of gases and/or discharge from a pneumostoma into the lumen of tube 924. Gases may leave tube 924 through filter 928 while discharge is retained within tube 924. One or more side openings 925 may be provided along tube 924 and/or close to the distal opening 926. The side openings 925 may be provided instead of, or in addition to, the opening 926 in the end of distal tip of tube 924. The side openings 925 permit gases and/or discharge to enter tube 924 even if one or more openings is occluded by tissue or other matter. Side openings may be provided in any of the pneumostoma vent tubes discussed in this application. The tube of a pneumostoma vent such as tube 924 may also be created from a porous material such that air may enter the lumen of the tube through the wall of the tube 924. The porous tube wall may be provided in addition to, or instead of, the presence of distal opening 926 or side openings 925. The tube of the pneumostoma vent, such as tube 924, may also be provided with features for maintaining the patency of the pneumostoma as shown in U.S. patent application Ser. No. 12/030,006, now U.S. Pat. No. 8,062,315, entitled "Variable Parietal/Visceral Pleural Coupling" which is incorporated herein by reference.

FIG. 9D shows an alternative pneumostoma vent 930 which has features within tube 934 designed to absorb discharge and prevent it from re-entering the lung. As shown in FIG. 9D, tube 934 includes a layer of absorbent material 935 within the wall of tube 934. The absorbent material 935 is exposed where the tube 934 is penetrated by side openings 937. Discharge that enters tube 934 through side openings 937 is absorbed by absorbent material 935. Any discharge that enters tube 934 though side openings 937 and end opening 936 is retained within tube 934 by filter 938 which is mounted flush with flange 932. Thus, discharge is collected in tube 934. The discharge is removed and disposed of when pneumostoma vent 930 is replaced.

FIG. 9E shows an alternative pneumostoma vent 940 which has features within tube 944 designed to absorb discharge and prevent it from re-entering the lung. As shown in FIG. 9E, tube 944 includes a layer of absorbent material 945 coated on the inside of tube 944. The absorbent material 945 is exposed on the inside of tube 944 such that discharge that enters tube 944 through opening 946 is absorbed by absorbent material 945. Any excess discharge that enters tube 944 is retained within tube 944 by filter 948 which is interference fit within flange 942. Thus, discharge is collected in tube 944. The discharge is removed and disposed of when pneumostoma vent 940 is replaced.

FIG. 9F shows an alternative pneumostoma vent 950 which has features external to tube 954 designed to absorb discharge and prevent it from re-entering the lung. As shown in FIG. 9F, a ring of absorbent material 955 is positioned around the proximal end of tube 954 where it meets flange 952. During use, the absorbent material 955 is trapped between flange 952 and the skin of the patient surrounding the pneumostoma. Discharge that leaks from the pneumostoma around the tube 954 through opening 956 is absorbed by absorbent material 955. Any discharge that enters tube 954 is retained within tube 954 by filter 958 which is bonded to the surface of flange 952. Thus, discharge is collected in tube 954. The discharge is removed and disposed of when pneumostoma vent 950 is replaced.

FIG. 9G shows an alternative pneumostoma vent 960 which has features incorporated in flange 962 to absorb discharge and prevent it from re-entering the lung. As shown in FIG. 9G, a disc of absorbent material 965 is laminated within a flexible flange 962. The flange 962 may be a laminate of polymers with an absorbent material in the middle which is flexible enough to conform to the chest of a patient. The flange 962 may be 3 mm or less in thickness and more preferably approximately 1 mm or less in thickness. The disc of absorbent material 965 is exposed around the proximal end of tube 964 where it meets flange 962. During use, the absorbent material 965 is exposed to the opening of the pneumostoma. Discharge that leaks from the pneumostoma around the tube 964 through opening 966 is absorbed by absorbent material 965. Any discharge that enters tube 964 is retained within tube 964 by filter 968. Filter 968 is attached to the proximal end of tube 964 by a plug 969. Plug 969 may be welded, bonded with adhesive or otherwise secured to tube 964 and/or flange 962 and operates in combination with flexible flange 962 to limit insertion of tube 964 into a pneumostoma. Thus, discharge is collected in tube 964 and flange 962. The discharge is removed and disposed of when pneumostoma vent 960 is replaced.

FIG. 9H shows an alternative pneumostoma management system 970 which has features incorporated in a chest mount 972 to absorb discharge and prevent it from re-entering the lung. As shown in FIG. 9H, a disc of absorbent material 975 is laminated within a flexible chest mount 972. The chest mount 972 may be a laminate of polymers with an absorbent material in the middle which is flexible enough to conform to the chest of a patient. The chest mount 972 may be 3 mm or less in thickness and more preferably approximately 1 mm or less in thickness. The disc of absorbent material 975 is exposed around the proximal end of tube 974 of pneumostoma vent 971 where it passes through chest mount 972. During use, the absorbent material 975 is exposed to the opening of the pneumostoma. Discharge that leaks from the pneumostoma around the tube 974 through opening 976 is absorbed by absorbent material 975. Any discharge that enters tube 974 is retained within tube 974 by filter 978. Filter 978 is attached to the proximal end of tube 974 as described elsewhere. Thus, discharge is collected in tube 974 and chest mount 972. The discharge is removed and disposed of when pneumostoma vent 971 and chest mount 972 is replaced. One or more features to control and/or absorb discharge emanating from the pneumostoma, for example, those features shown in FIGS. 9A-9F may be incorporated into pneumostoma vents and chest mounts of different design—for example, those other pneumostoma vent designs described elsewhere in this application.

FIGS. 10A-D illustrate alternative configurations of adhesive on the distal surface 1032 of a pneumostoma vent 1000. Flange 1002 of pneumostoma vent 1000 has an adhesive material distributed thereon. In the absence of a chest mount, this adhesive is used to temporarily secure the flange 1002 of the pneumostoma vent 1000 to the chest of the patient. Adhesive materials may be hydrocolloid adhesives which absorb moisture while retaining good adhesiveness. However, even the best adhesives may cause irritation of the skin during prolonged exposure. Tissue irritation may result merely from build up of moisture on the skin behind the pneumostoma vent 1000 regardless of the presence of any particular adhesive. However, the distribution of adhesive may be controlled so as to help reduce irritation to the skin of the patient.

One way to reduce the potential for irritation is by reducing the amount of time any particular portion of skin is in contact with adhesive and/or allowing the skin in regions behind pneumostoma vent 1000 to "breathe" when not in contact with adhesive. Thus, in some embodiments the adhesive may be provided in stripes or patches and absent in other stripes or patches. The adhesive areas may also be elevated slightly above the surface of flange 1002 such that non adhesive areas of flange 1002 do not contact the skin but leave a slight air gap through which air may circulate and/or moisture may escape. The adhesive patches themselves may comprise a breathable laminate and adhesive so that the prolonged attachment of the PMD does not irritate the skin. The adhesive patches may be arranged differently on different chest mounts so as to contact different regions of skin surrounding a pneumostoma. Alternatively, the arrangement of adhesive patches may be the same on each chest mount but the registration of the patches may be changed by chance or deliberately each time a chest mount is replaced so that the adhesive patches contact different regions of skin surrounding a pneumostoma.

Figure 10A:
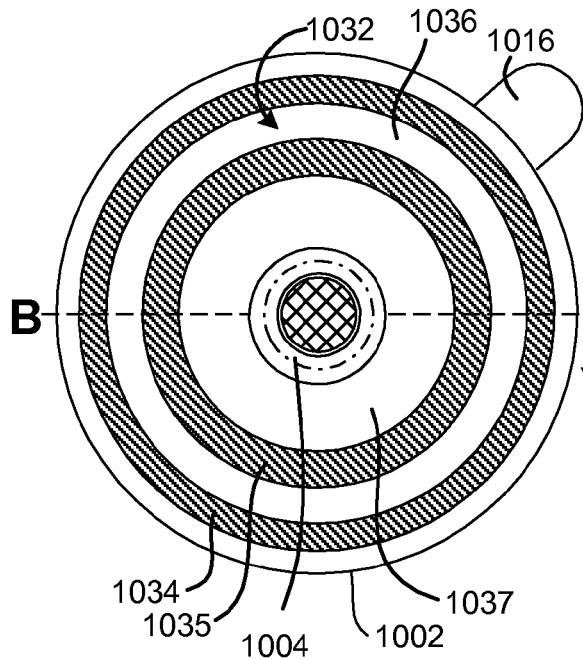
FIGS. 10A-10D show alternative adhesive patterns for attachment of pneumostoma vents according to embodiments of the present invention.

Referring now to FIG. 10A where the contact surface 1032 of a flange 1002 of a pneumostoma vent 1000 is shown. Adhesive pads 1034, 1035 are located on contact surface 1032 around tube 1004. The adhesive is selected so as to help maintain the correct position of pneumostoma vent 1000 without causing undue irritation to the skin of the patient. As shown in FIG. 10A, adhesive pads 1034, 1035 are provided in two discrete spaced-apart regions. Each adhesive pad 1034, 1035 preferably comprises a laminate structure with an inner plastic, paper or foam layer (e.g., closed-cell polyethylene foam) sandwiched between layers of adhesive. The adhesive pads 1034, 1035 are elevated above contact surface 1032 by the thickness of the inner layer. Thus, only some portions of skin around a pneumostoma will be in contact with adhesive each time pneumostoma vent 1000 is changed. Different pneumostoma vents may be provided with different arrangements of adhesive patches. For example, a second pneumostoma vent may have adhesive patches located in the empty areas 1036, 1037 of contact surface 1032 such that it will contact different areas of skin.

Figure 10B:
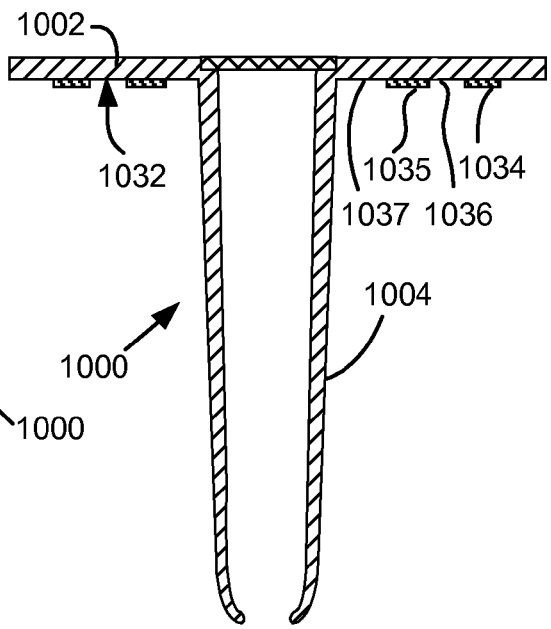

FIG. 10B shows a sectional view of pneumostoma vent 1020 along line B-B, as shown in FIG. 10A. FIG. 10B shows that contact surface 1032 is spaced apart from the skin of the patient when pneumostoma vent 1000 is applied. Air can circulate between the adhesive pads 1034, 1035 and the empty areas 1036, 1037. As previously described, the adhesive pads may be protected by a protector sheet that is removed prior to use of PMD 200. The pneumostoma vent 1000 is also provided with one or more tabs 1016 which are free of adhesive (shown in FIG. 10A). These tabs 1016 allow a patient to grip the flange 1002 to gently peel the chest mount off the skin when it needs replacement.

Adhesive pads 1034, 1035 may alternatively be rings of hydrocolloid adhesive of approximately a millimeter in thickness and secured to flange 1002 with a transfer adhesive. Any medically approved water resistant pressure sensitive adhesive may be used to attach the pneumostoma vent to the skin of the patient, such as hydrocolloid adhesives, zinc oxide adhesives and hydrogel adhesives. Particularly effective adhesives in providing the desired adhesive properties to secure the pneumostoma vent to the skin of the wearer without irritation are formed from cross-linking polymers with a plasticizer to form a 3-dimensional matrix. Some useful adhesives are disclosed in WO 00/07637, WO 00/45866 WO 00/45766 and U.S. Pat. No. 5,543,151, which are incorporated herein by reference. The adhesive can be applied to the contact surface 1032 of flange 1002 by any means known in the art, for example, slot coating, spiral, bead application or printing.

Figure 10C:
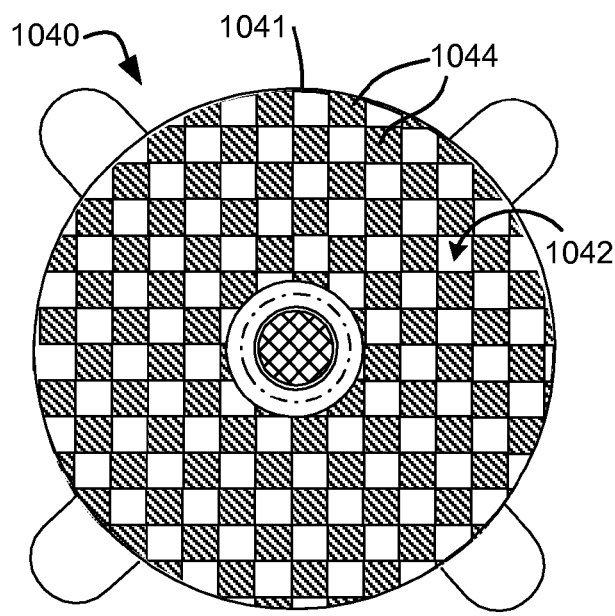

Referring now to FIG. 10C where a different distribution of adhesive on contact surface 1042 of flange 1041 of a pneumostoma vent 1040 is shown. As shown in FIG. 10C, adhesive pads may be distributed in small patches 1044. The adhesive patches 1044 may cover a less than 100% of the contact area 1042. As shown in FIG. 10C, adhesive patches 1044 cover approximately half of the contact surface 1042 of pneumostoma vent 1040. Adhesive patches 1044 preferably cover from 10% to 50% of contact surface 1042. With the distribution pattern of FIG. 10C all pneumostoma vents may have the same distribution of adhesive. Because patches 1044 are small and evenly distributed, variations of the orientation of placement of pneumostoma vent 1040 will randomize the location of the patches 1044 relative to the skin of the patient such that a particular region of skin is only in contact with adhesive for a percentage of time similar to the percentage of coverage.

Figure 10D:
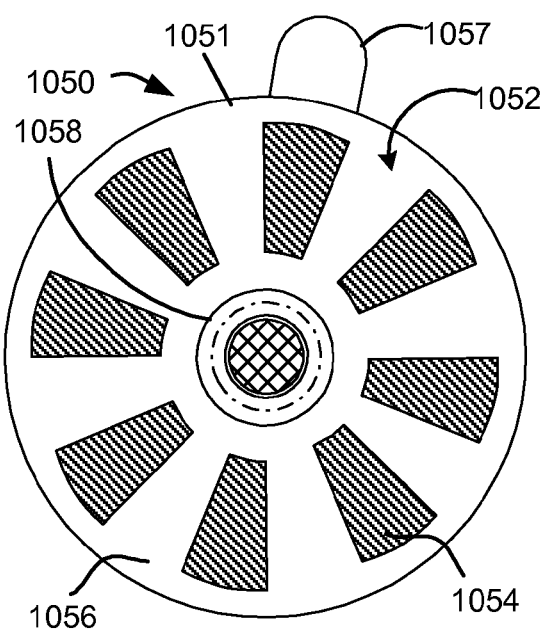

FIG. 10D illustrates an alternative method for rotating the portions of skin around a pneumostoma that are in contact with adhesive. As shown in FIG. 10D, pneumostoma vent 1050 has eight radial adhesive patches 1054. The patches are arranged in a regular pattern around tube 1058 such that the patches are interspersed with non-adhesive areas 1056. As shown in FIG. 10D, adhesive patches 1054 cover approximately half of the contact surface 1052 of pneumostoma vent 1050. Adhesive patches 1054 preferably cover from 10% to 50% of contact surface 1052. A tab 1057 is aligned with one of the adhesive patches 1054. With the pneumostoma vent 1050 of FIG. 10D, the patient deliberately changes the orientation of tab 1057 relative to the pneumostoma each time a pneumostoma vent 1050 is changed. By changing the rotation of the pneumostoma vent 1050 the patient can change which portions of skin are in contact with adhesive patches 1054. The adhesive distribution pattern of FIG. 10D is also advantageous because air can circulate between adhesive patches 1054 and the non-adhesive areas 1056. The circulation of air allows moist air to exit from between the skin of the patient and flange 1051.

FIGS. 10E-10G illustrate an alternate pneumostoma vent 1060. As shown in FIG. 10E, pneumostoma vent 1060 has a flexible connector 1061 connecting flange 1062 and tube 1064. As illustrated in FIG. 10E, flexible connector 1061 may be formed in one piece with flange 1062 and tube 1064. An accordion or bellows-like flexible connector 1061 is shown. In alternative embodiments connector 1061 may be a separate joint/coupling/component or a region of flexible material. For example, a lower durometer material having more flexibility to allow bending but also having a wire reinforcement to prevent radial tube collapse. Flexible connector 1061 should be flexible enough to allow relative movement of flange 1062 and tube 1064 while providing sufficient stability to allow insertion of tube 1064 into a pneumostoma. Additionally, the connector should be selected so as not to prevent gases from escaping through the lumen of tube 1064. In alternative embodiments the flexible connector 1061 may form part of flange 1062 instead of tube 1064.

As shown in FIG. 10F, in some embodiments, flexible connector 1061 may be sufficiently flexible to allow flange 1062 to fold parallel to tube 1064. This is advantageous in that it reduces the size of packaging required to contain pneumostoma vent 1060. In many cases, a patient will change their pneumostoma vent daily. Thus, the space occupied by one month's supply of pneumostoma vents becomes considerable. By folding the flange 1062 parallel with the tube 1064, the overall packaging volume (height*length*width) for the pneumostoma vent 1060 can be significantly reduced. The reduction in volume weight and amount of packing increases the convenience to the patient. Additionally, the reduction in volume and packing materials required reduces associated shipping costs and expense.

As shown in FIG. 10G, a flexible connector 1061 may also be useful to facilitate insertion of tube 1064 into a pneumostoma 1068, which is oriented at an angle relative to the skin 114 of the patient. A pneumostoma 1068 may be formed at an angle during the pneumostomy procedure or may migrate slightly over time. The angle formed between the skin 114 of the chest 100 and the pneumostoma 1068 will depend not only upon the pneumostomy procedure but also the location of the pneumostoma and the patient's anatomy in the region of the pneumostoma 1068. If the flange 1062 is inflexibly mounted to the tube 1064, it will tend to pull up on one side of the pneumostoma and "dig in" on the other side of the pneumostoma—destabilizing the pneumostoma vent and causing the patient discomfort.

As shown in FIG. 10G, flexible connector 1061 is advantageous in that it allows flange 1062 to lay flat against the skin 114 of chest 100 while allowing tube 1064 to follow the channel of pneumostoma 1068. The flexible connector 1061 allows the pneumostoma vent 1060 to conform to the pneumostomas of a wide range of patients. Note that flexible connector is designed so as to allow variation in the relative angle of flange 1062 and tube 1064 without greatly impinging upon the lumen of tube 1064. However, for this application it is not essential that flexible connector permit flange 1062 and tube 1064 to be parallel to one another as the pneumostoma will more typically be oriented within forty-five degrees of perpendicular to the skin 114 of chest 100.

Figure 10H:
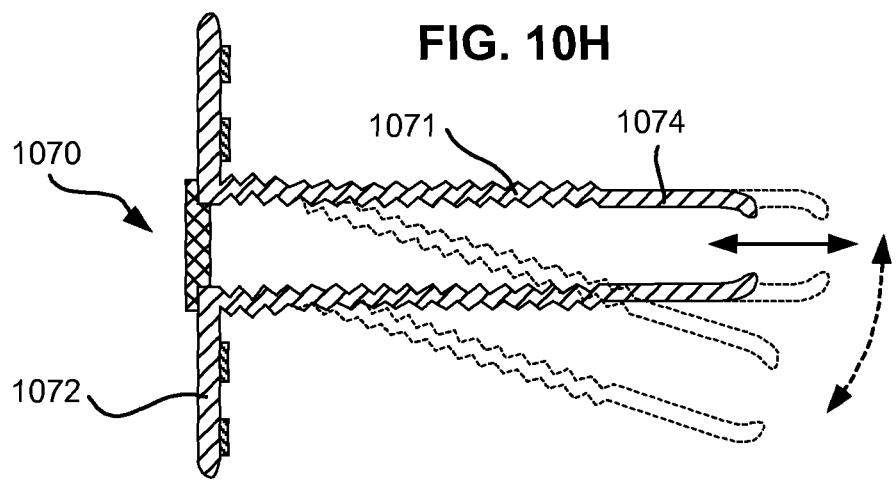
FIGS. 10H-10J show views of alternative pneumostoma vents according to embodiments of the present invention.

FIG. 10H illustrates an alternate pneumostoma vent 1070. As shown in FIG. 10H, pneumostoma vent 1070 has a flexible connector 1071 connecting flange 1072 and tube 1074. An accordion or bellows-like flexible connector 1071 is shown. As illustrated in FIG. 10H, flexible connector 1071 may be formed in one piece with flange 1072 and/or tube 1074. Flexible connector 1071 may alternatively be formed separately from flange 1072 and/or tube 1074 and securely attached to flange 1072 and/or tube 1074. Flexible connector 1071 may expand or contract in length thereby allowing adjustment to the length of pneumostoma vent 1070. The length of pneumostoma vent 1070 may be manually adjusted by stretching or compressing flexible connector 1071. The length of pneumostoma vent 1070 may be manually adjusted to suit a particular patient prior to insertion of tube 1074 into a pneumostoma. Additionally, flexible connector 1071 may bend during insertion to facilitate insertion of tube 1074 into a pneumostoma which is oriented at an angle relative to the skin 114 of the patient. Additionally, flexible connector 1071 may expand or contract in vivo thereby allowing the length of pneumostoma vent 1070 to adjust and accommodate movement of the pneumostoma as the patient moves. Additionally, flexible connector 1071 may be sufficiently flexible to allow flange 1072 to fold parallel to tube 1074 prior to use for reduced packaging volume.

Figure 10I:
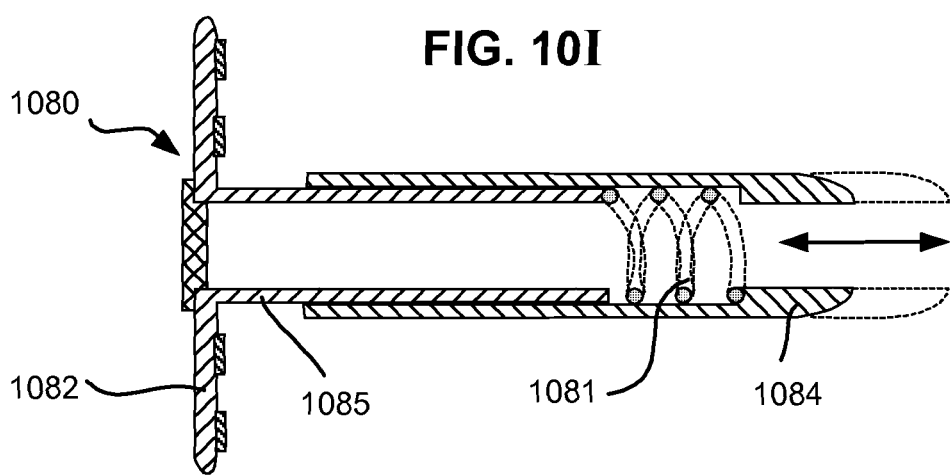

FIG. 10I illustrates an alternate pneumostoma vent 1080. As shown in FIG. 10I, pneumostoma vent 1080 has a spring 1081 an inner tube 1085 and outer tube 1084. Inner tube 1085 is connected to flange 1082. Spring 1081 is a polymer or metal spring and is preferably bonded at the proximal end inner tube 1085 and at the distal end to outer tube 1084. Spring 1081 may be a coil spring as shown or a leaf spring, or other elastic element. As shown outer tube 1084 is received over inner tube 1085 and can slide so that the overall length of pneumostoma vent 1080 may increase or decrease by compressing or stretching spring 1081. Spring 1081 may expand or contract in length thereby allowing adjustment to the length of pneumostoma vent 1080. The length of pneumostoma vent 1080 may be manually adjusted by stretching or compressing spring 1081. The length of pneumostoma vent 1080 may be manually adjusted to suit a particular patient prior to insertion of tube 1084 into a pneumostoma. Additionally, spring 1081 may expand or contract in vivo thereby allowing the length of pneumostoma vent 1080 to adjust and accommodate movement of the pneumostoma as the patient moves.

Figure 10J:
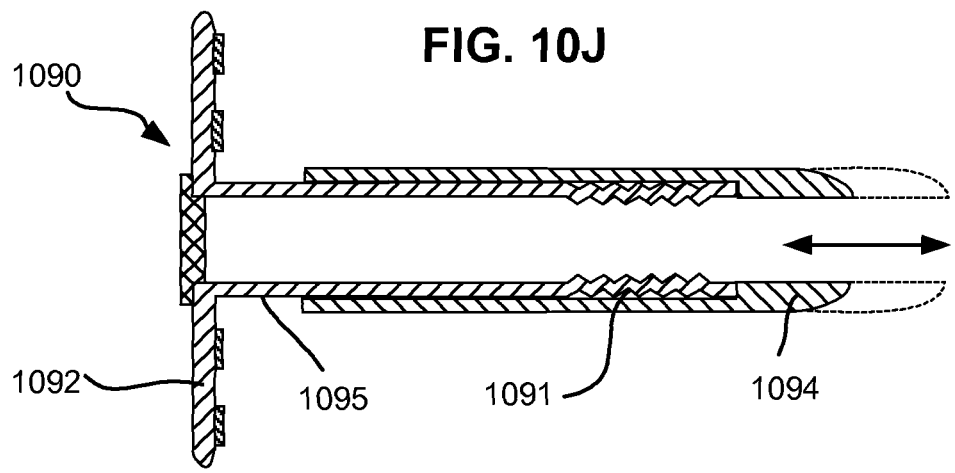

FIG. 10J illustrates an alternate pneumostoma vent 1090. As shown in FIG. 10J, pneumostoma vent 1090 has a flexible connector 1091 formed at the end of an inner tube 1095. Inner tube 1095 is connected at the other end to flange 1092. Flexible connector 1091 is preferably formed in one piece with inner tube 1095 and then bonded at the distal end to outer tube 1094. As shown in FIG. 10J, outer tube 1094 is received over inner tube 1095 and can slide so that the overall length of pneumostoma vent 1090 may increase or decrease by compressing or stretching flexible connector 1091. Flexible connector 1091 may expand or contract in length thereby allowing adjustment to the length of pneumostoma vent 1090. The length of pneumostoma vent 1090 may be manually adjusted by stretching or compressing flexible connector 1091. The length of pneumostoma vent 1090 may be manually adjusted to suit a particular patient prior to insertion of tube 1094 into a pneumostoma. Additionally, flexible connector 1091 may expand or contract in vivo thereby allowing the length of pneumostoma vent 1090 to adjust and accommodate movement of the pneumostoma as the patient moves.

Figure 11A:
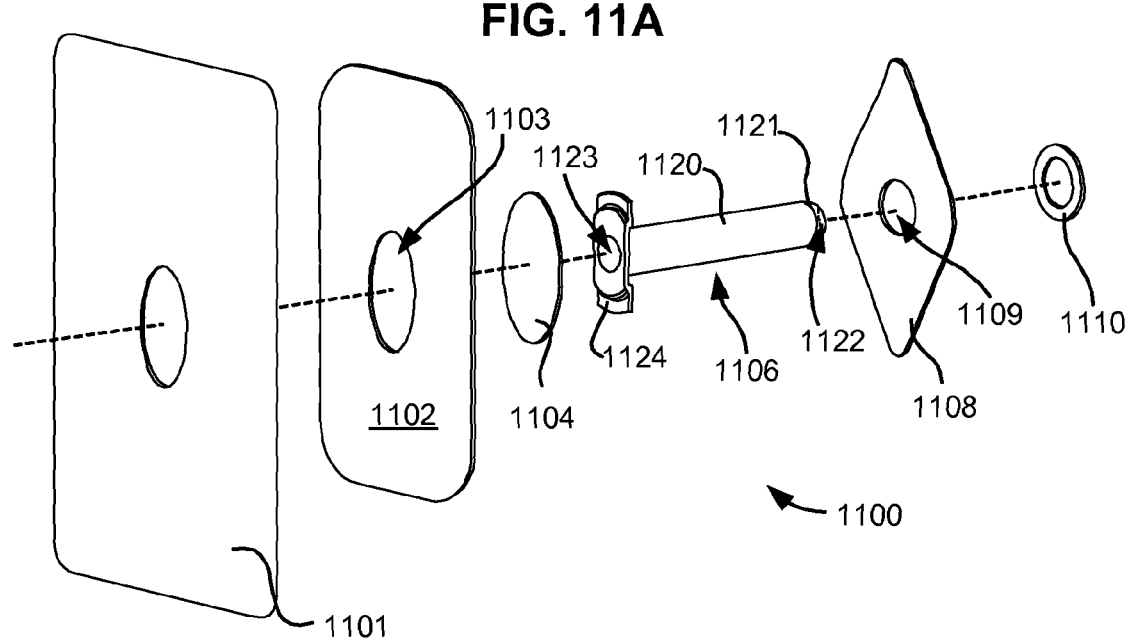
Figure 11B:
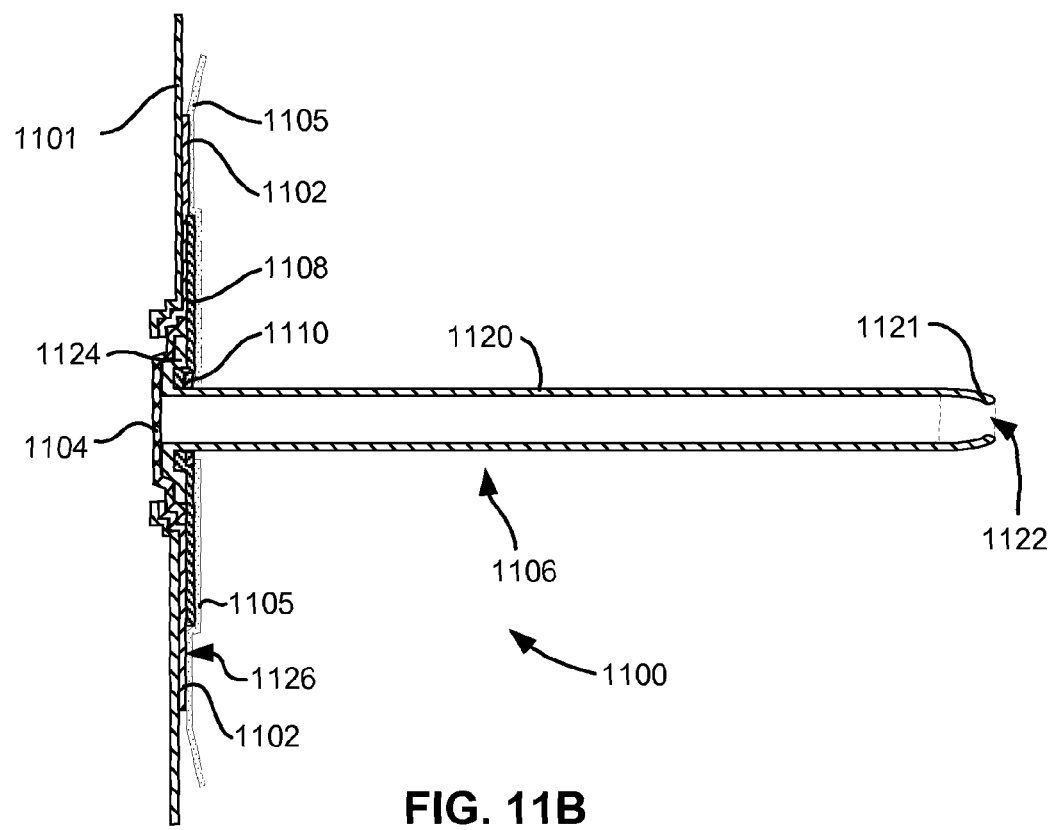

FIGS. 11A-B show exploded and sectional views of a pneumostoma management device comprising pneumostoma vent system 1100. Pneumostoma vent system 1100 is designed to be secured directly to the chest of the patient. FIG. 11A shows an exploded view of the main components of pneumostoma vent system. From left to right these components are carrier sheet 1101, adhesive cover 1102, filter 1104, vent 1106, and adhesive patch 1108 and washer 1110.

Adhesive cover 1102 is a thin porous biocompatible membrane which has adhesive on the surface facing the pneumostoma (inner surface 1126 shown in FIG. 6B) and non-adhesive on the outer surface. A suitable material for adhesive cover 1102 is a thin polyurethane film bearing an acrylic adhesive—such materials are available from 3M of St. Paul, Minn. The film is biocompatible as well as thin, strong, and breathable. Adhesive cover 1102 has an aperture 1103 large enough to allow air to exit through filter 1104. Aperture 1103 is preferably slightly smaller than filter 1104 so that annular cover 1102 can be used to secure filter 1104 to vent 1106. Exposed portions of annular adhesive cover 1102 are provided with a paper cover to protect the adhesive prior to use. Adhesive cover 1102 is releasably secured to a carrier liner 1101 for ease of handling during manufacture and application of the finished pneumostoma vent system 1100. Carrier liner 1101 is removed after the pneumostoma vent system 1100 has been correctly positioned in the pneumostoma. The carrier liner 1101 need not cover the entire adhesive cover 1102, but may be star-shaped or another shape different than the adhesive cover. This allows for ease of handling and placing the adhesive cover with reduced likelihood of creating bubbles and wrinkles in the adhesive cover during placement. The carrier liner 1101 may be arranged, for example, in a window configuration.

Filter 1104 is a circular disc of filter material. Filter 1104 is preferably a hydrophobic filter material. In a preferred embodiment, filter 1104 is a reticulated open cell polyurethane foam or an open cell polyurethane or polyester foam or melt blown polyethylene. Exemplary filter materials include DELPORE® DP2001-10P, DELPORE® DP2001-20P, and DELPORE® DP2001-30P available from Delstar Technologies, Inc. (Middletown, Del.). Filter 1104 is larger than the proximal aperture 1123 in vent 1106 and is positioned over the proximal aperture 1123 to filter gases moving in and out of the vent 1106. Filter 1104 may be secured to vent 1106 by an adhesive, welding, or other bonding technology. In a preferred embodiment, filter 1104 is secured to vent 1104 with a ring of pressure sensitive adhesive. Filter 1104 is also secured to vent 1106 by adhesive cover 1102 instead of, or in addition to, other bonding techniques.

Vent 1106 comprises a tube 1120 for entering the pneumostoma. As previously discussed, tube 1120 has an atraumatic tip 1121 and one or more apertures 1122 in the distal end to allows gases and discharge to enter tube 1120 from a pneumostoma. Tube 1120 has a flange 1124 at the proximal end. Flange 1124 is formed in one piece with tube 1120. Filter 1104 is secured over proximal opening 1123 of vent 1106 as described in the previous paragraph. Vent 1106 may be made of a suitable plastic/thermoplastic polymer/thermoplastic elastomer. For example, in one preferred embodiment vent 1106 is made of PEBAX® a block copolymer with suitable mechanical and chemical properties available from Arkema (Colombes, France).

Figure 11E:
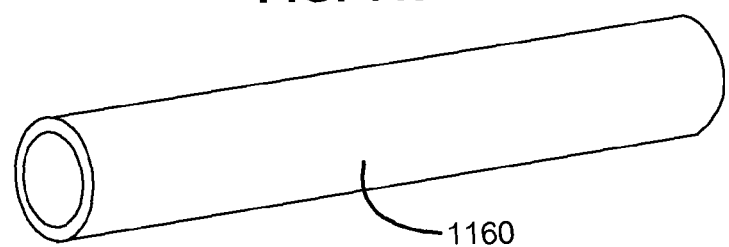
FIGS. 11E-11H show steps in the manufacture of a pneumostoma vent tube according to an embodiment of the present invention.
Figure 11F:
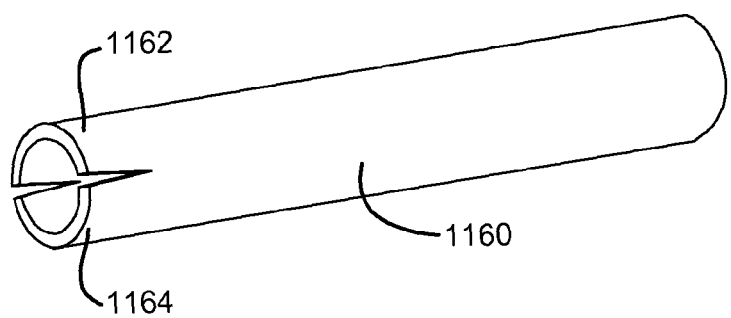
Figure 11G:
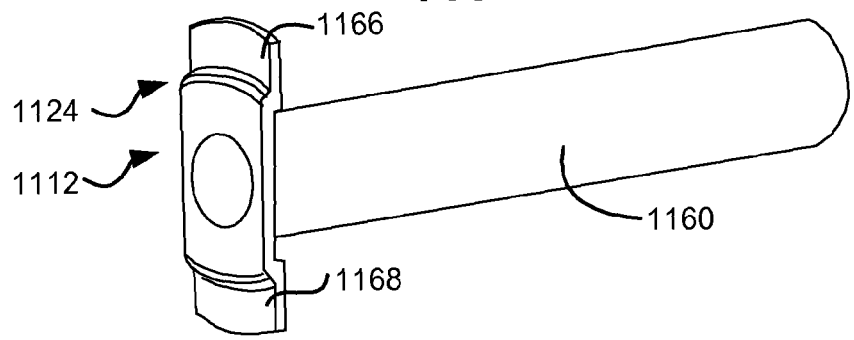
Figure 11H:
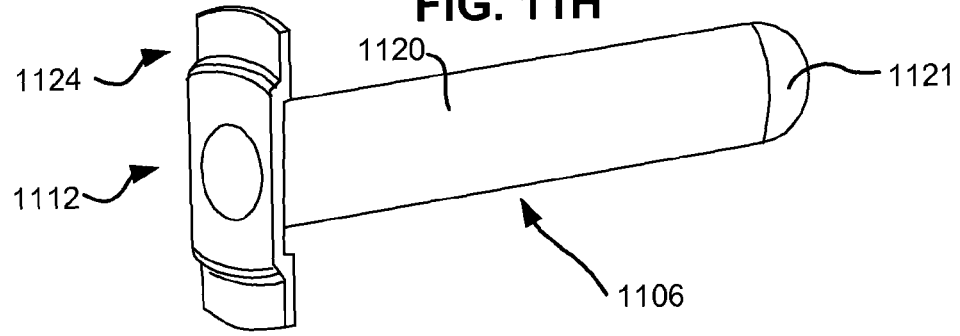

An efficient way to make tube 1120 and flange 1124 is illustrated in FIGS. 11E-11G. The process begins with extruded tube stock. The tube stock is cut to the approximate length required as shown in FIG. 11E which shows a length of extruded tube 1160. Pneumostoma vents 1112 may be readily manufactured in a range of lengths according to this method. Next, the proximal end of the tube 1160 is cut in half parallel to the long axis of the tube to a depth of 20 mm or so. The proximal end of tube 1160 is, thus, in two sections 1162, 1164. The proximal end of tube 1160 is then placed in a heated fixture to form the two wings 1166, 1168 of flange 1124. Any excess material is trimmed and the flange 1124 is finished as shown in FIG. 11G. In a preferred embodiment, wings 1166, 1168 extend at least 0.125 to 0.25 inches from the outer diameter of tube 1160 in order to secure tube 1160 to the remainder of pneumostoma vent system 1100. Tube 1160 may then be trimmed at the distal end to the exact length required. The distal end is then tipped using a heated fixture to form the distal end into the rounded distal tip 1121 of the finished vent 1106 as shown in FIG. 11H.

Figure 11I:
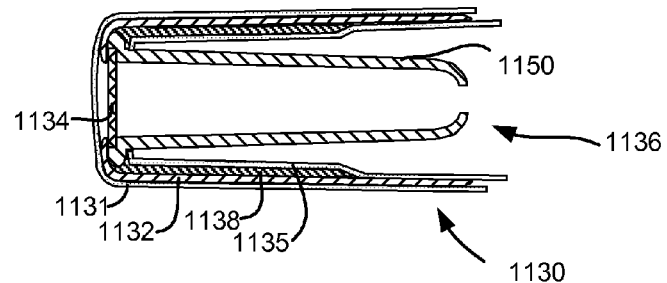
FIGS. 11I and 11J show packaging options for a preferred pneumostoma vent system according to an embodiment of the present invention.
Figure 11J:
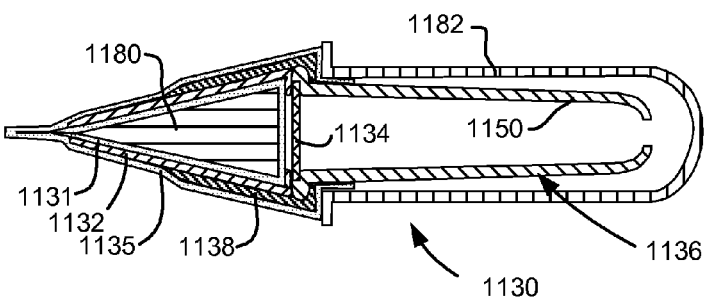
Figure 11K:
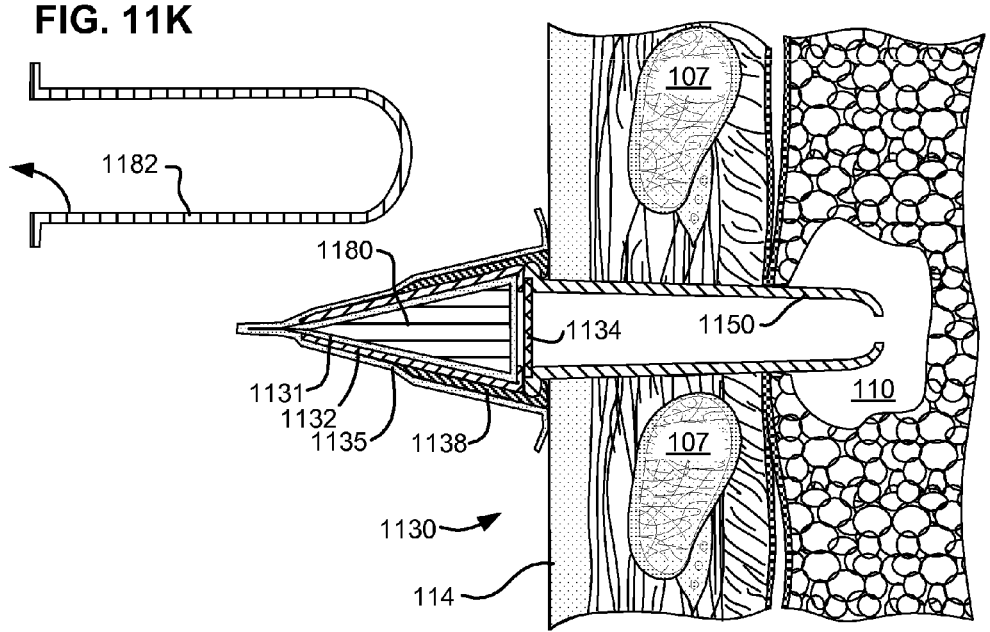
FIGS. 11K-11M show steps in the deployment of a preferred pneumostoma vent system as packaged in FIG. 11J according to an embodiment of the present invention.
Figure 11L:
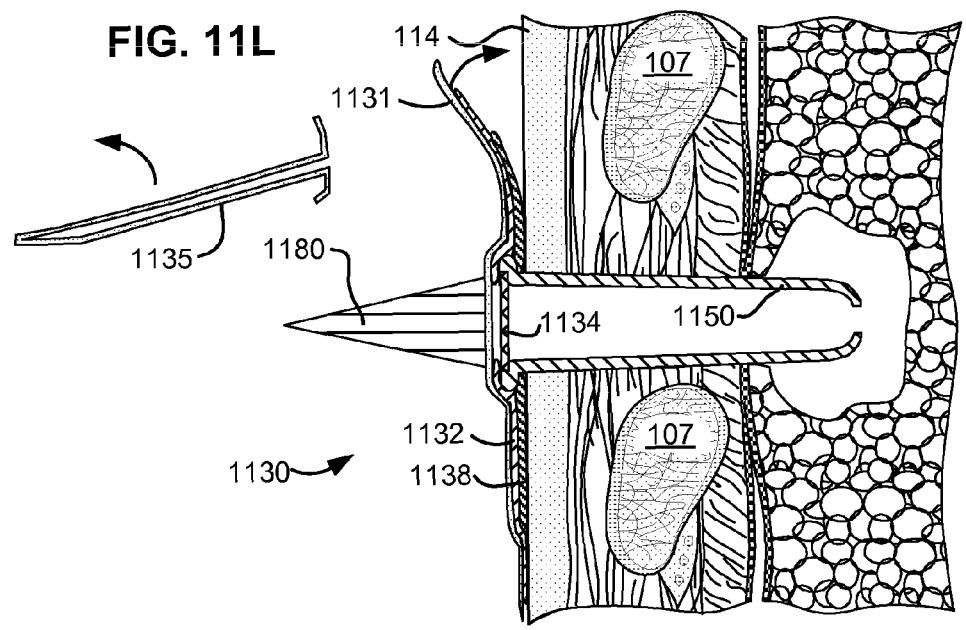
Figure 11M:
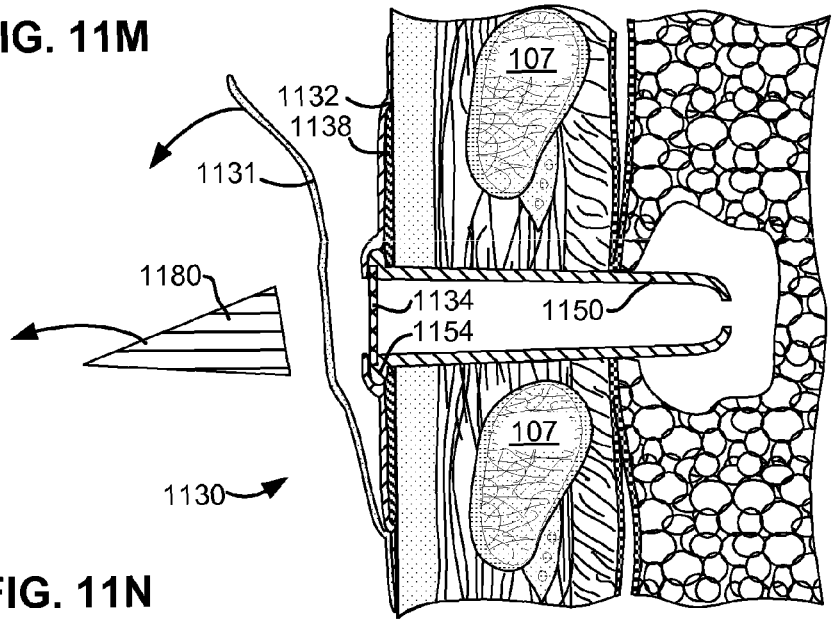
Figure 11N:
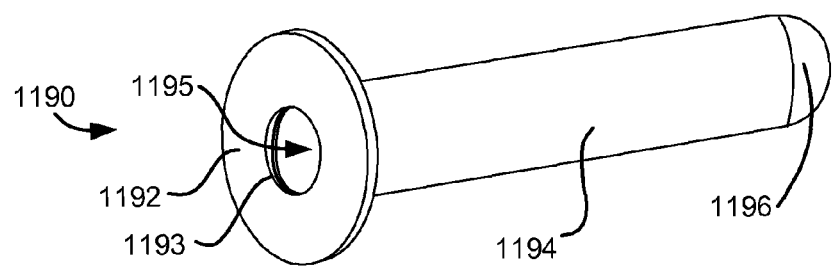
FIG. 11N shows a preferred embodiment of a pneumostoma vent tube for a pneumostoma vent.

Another way to make vent 1106 is illustrated by pneumostoma vent 1190 of FIG. 11N. Pneumostoma vent 1190 is made from two pieces. A washer-shaped flange 1192 and a tube 1194. The flange 1192 preferably has an outer diameter approximately twice the diameter of tube 1194. The aperture 1193 of flange 1192 is approximately the same size as the inner diameter of the proximal opening 1195 in tube 1194. Flange 1192 is preferably heat set to the proximal end of tube 1194 but may also be bonded to tube 1194 using adhesive, ultrasonic welding and/or other reliable methods of securing the components. As before, tube 1194 may be cut to length from extruded stock and then tipped at the distal end 1196 in a heated fixture either before or after attaching flange 1192 to the proximal end.

Referring again to FIGS. 11A and 11B, adhesive patch 1108 is preferably a biocompatible hydrocolloid material. Adhesive patch 1108 has a central aperture 1109 which is sized to fit vent 1106. The hydrocolloid material is provided with a polymer layer and a transitional adhesive on the side facing flange 1124 in order to better secure adhesive patch 1108 to the flange and annular cover. Flange 1124 is too large to fit through aperture 1109. The polymer layer prevents aperture 1109 from deforming sufficiently for the flange 1124 to pass through aperture 1109. During assembly, the distal side of flange 1124 may also be bonded to the polymer layer of adhesive patch 1108 using, for example, pressure sensitive adhesive, UV-cured adhesive or ultrasonic welding. Adhesive patch 1108 is preferably less than 3 mm thick, and is, more preferably, approximately 1 mm in thickness. Exposed portions of adhesive patch 1108 are provided with a paper cover to protect the hydrocolloid adhesive prior to use. Washer 1110 slides over vent 1106 and is bonded to adhesive patch 1108 and vent 1106. Adhesive patch 1108 is sandwiched between washer 1110 and flange 1124 thereby firmly securing adhesive patch 1108 to vent 1106.

Pneumostoma vent system 1100 is preferably preassembled when provided to the patient. FIG. 11B shows a sectional view of pneumostoma vent system 1100 as assembled. Note that tube 1120 fits through the middle of adhesive patch 1108. Note also that flange 1124 is trapped between adhesive cover 1102 and adhesive patch 1108. In this embodiment, filter 1104 is also secured to vent 1106 by adhesive cover 1102. Exposed adhesive regions of adhesive cover 1102 and adhesive patch 1108 on the patient side of the pneumostoma vent system 1100 assembly are provided with protective covers 1105 (for example, paper covers) to protect the adhesive during shipping and prior to use. The completed or partially completed pneumostoma vent system 1100 is provided as a sterile product to the patient or caregiver. The protective covers 1105 are peeled off prior to application of the pneumostoma vent system 1100 to the pneumostoma. After the pneumostoma vent is correctly positioned in the pneumostoma, the carrier liner 1101 is also removed.

FIGS. 11C and 11D show exploded and sectional views of an alternate pneumostoma vent system 1130. Pneumostoma vent system 1130 is designed for use without a chest mount although it could be adapted for use with a chest mount. FIG. 11C shows an exploded view of the main components of pneumostoma vent system 1130. From right to left these components are carrier sheet 1131, adhesive cover 1132, filter 1134, vent 1136, adhesive patch 1138 and protective cover 1135. No washer is present in this embodiment.

Adhesive cover 1132 is a thin porous biocompatible membrane which has adhesive on the surface facing the pneumostoma (the distal surface) and non-adhesive on the outer surface (the proximal surface). Adhesive cover 1132 has an aperture 1133 large enough to allow air to exit through filter 1134. Aperture 1133 is slightly smaller than filter 1134 so that adhesive cover 1132 can be used to secure filter 1134 to vent 1136. Cover 1135 protects the exposed adhesive areas of adhesive cover 1132 prior to use. Adhesive cover 1132 is releasably secured to a carrier liner 1131 for ease of handling during manufacture and application of the finished pneumostoma vent system 1130. Carrier liner 1131 is removed after the pneumostoma vent system 1130 has been correctly positioned in the pneumostoma.

Vent 1136 comprises a tube 1150 for entering the pneumostoma. As previously discussed, tube 1150 has an atraumatic tip 1151 and one or more apertures 1152 in the distal end to allows gases and discharge to enter tube 1150 from a pneumostoma. Tube 1150 has a flange 1154 at the proximal end. Flange 1154 is formed in one piece with tube 1150, for example, by using the process described with respect to FIGS. 11E-11H. Filter 1134 is a circular disc of filter material. Filter 1134 is preferably a hydrophobic filter material. Filter 1134 is larger than the proximal aperture 1153 in pneumostoma vent 1136 and is positioned over the proximal aperture 1153 of vent 1136 to filter gases moving in and out of the vent 1136 as shown in FIG. 11D. In a preferred embodiment, filter 1134 is secured to vent 1136 with a ring of pressure sensitive adhesive (not shown). Filter 1134 is also secured to vent 1136 by adhesive cover 1132.

Adhesive patch 1138 is preferably a biocompatible hydrocolloid material Adhesive patch 1138 has a central aperture 1139 which is sized to fit vent 1136. The hydrocolloid material is provided with a polymer layer and a transitional adhesive on the side facing flange 1154 in order to better secure adhesive patch 1138 to the flange and adhesive cover. Flange 1154 is too large to fit through aperture 1139. The polymer layer prevents aperture 1139 from deforming sufficiently for the flange 1154 to pass through aperture 1139.

Pneumostoma vent system 1130 is preferably preassembled when provided to the patient. FIG. 11D shows a sectional view of pneumostoma vent system 1130 as assembled. Note that tube 1150 fits through the middle of adhesive patch 1138. Note also that flange 1154 is trapped between adhesive cover 1132 and adhesive patch 1138. In this embodiment, filter 1134 is also secured to vent 1136 by adhesive cover 1132. Exposed adhesive regions of adhesive cover 1132 and adhesive patch 1138 on the patient side of the pneumostoma vent system 1130 assembly are provided with protective cover 1135 (for example, a paper cover which may be in one or more parts) to protect the adhesive during shipping and prior to use. The protective covers 1135 are peeled off prior to application of the pneumostoma vent system 1130 to the pneumostoma. After the pneumostoma vent 1136 is correctly positioned in the pneumostoma, the carrier liner 1131 is also removed.

Pneumostoma vent system 1100 and alternate pneumostoma vent system 1130 may be applied to a pneumostoma in the same ways previously described. See, e.g., FIGS. 6C, 7A, 7B and accompanying text. The vent is inserted into the pneumostoma and the tube of the vent passes through the chest wall into the lung. Gases and discharge may enter the vent of the pneumostoma vent system through the distal aperture. The flange is secured to the skin of the patient by the adhesive patch and adhesive cover. The flange, patch and cover cooperate to secure the vent in position within the pneumostoma. Discharge may accumulate in the tube of the vent during use. Periodically, or as needed, the pneumostoma vent system is removed, disposed of and replaced. Typically the pneumostoma vent system will be replaced daily.

The completed pneumostoma vent system 1100 or 1130 is typically provided as an assembled and sterilized product to the patient or caregiver. The adhesive patch 1108, 1138 adhesive cover 1102, 1132, carrier liner 1101, 1131 and protective cover 1105, 1135 are thin and flexible and, thus, may be folded along side the tube 1120, 1150 of vent 1106, 1136 for packaging and transport. This is advantageous in that it reduces the size of packaging required to contain pneumostoma vent system 1100, 1130. In many cases, a patient will change their pneumostoma vent daily. Thus, the space occupied by one month's supply of pneumostoma vents becomes considerable. By folding the outer portion of the pneumostoma vent system 1100, 1130 parallel with the tube 1120, 1150, the overall packaging volume (height*length*width) for the pneumostoma vent 1100, 1130 can be significantly reduced. The reduction in volume weight and amount of packing increases the convenience to the patient. Additionally, the reduction in volume and packing required reduces associated shipping costs and expense.

FIG. 11I shows an example of a pneumostoma vent system 1130 in a folded configuration for shipping and storage. As shown in FIG. 11I, the carrier liner 1131, adhesive cover 1132, adhesive patch 1138 and protective cover 1135 are all folded alongside tube 1150 of vent 1136. The pneumostoma vent system 1130 is unfolded prior to removal of protective cover 1135 and application to the patient.

FIG. 11J shows an alternate packaging of pneumostoma vent system 1130. As shown in FIG. 11J, pneumostoma vent system 1130 is packaged with a mandrel 1180 and cover 1182. Mandrel 1180 is a disposable structural element made of plastic or foam. Mandrel 1180 is positioned in line with tube 1150 of vent 1136. The carrier liner 1131, adhesive cover 1132, adhesive patch 1138 and protective cover 1135 are all folded alongside mandrel 1180. Mandrel 1180 provides support for the components and a gripping point for insertion of tube 1150 into a pneumostoma. Protective cover 1135 holds the remaining components against mandrel 1180 until removed. Cover 1182 is a test-tube shaped plastic molding which protects tube 1150 up until insertion in the pneumostoma thereby helping to keep the tube 1150 free from contaminants.

To use the pneumostoma vent system 1130 as packaged in FIG. 11J, the patient grips mandrel 1180 with one hand and removes and discards cover 1182 with the other hand exposing tube 1150. This arrangement keeps tube 1150 free of contaminants and helps avoid handling of tube 1150 by the patient/caregiver. The patient then inserts tube 1150 into the pneumostoma 110 as shown in FIG. 11K. The patient then peels of protective cover 1135, exposing the adhesive surfaces of adhesive cover 1132 and adhesive patch 1138 and releasing them from mandrel 1180 as shown in FIG. 11L. The patient then pushes the adhesive surfaces of adhesive cover 1132 and adhesive patch 1138 against the skin 114 adjacent the pneumostoma 110 and applies pressure to carrier liner 1131 to smooth them down. Mandrel 1180 may be removed and discarded at this time. Carrier liner 1131 facilitates handling of adhesive cover 1132 which is designed to be flexible and breathable so as not to irritate the skin surrounding the pneumostoma. Carrier liner 1131 may now be peeled away and discarded as shown in FIG. 11M, leaving pneumostoma vent system 1130 correctly positioned and deployed with filter 1134 exposed. Tube 1150 is secured by adhesive patch 1138 and adhesive cover 1132 which, by sandwiching flange 1154 hold tube 1150 in the desired position. Gases may now escape from the pneumostoma via tube 1150 and filter 1134.

Materials

In preferred embodiments the pneumostoma management device and its components are formed from biocompatible polymers or biocompatible metals. A patient will typically wear a pneumostoma management device for extended periods, and, thus, the materials, particularly of the tube entering a pneumostoma, should meet high standards for biocompatibility. In general preferred materials for manufacturing pneumostoma management devices are biocompatible thermoplastic elastomers that are readily utilized in injection molding and extrusion processing. As will be appreciated, other suitable similarly biocompatible thermoplastic or thermoplastic polymer materials can be used without departing from the scope of the invention.

Biocompatible polymers for manufacturing pneumostoma management devices and components thereof may be selected from the group consisting of polyethylenes (HDPE), polyvinyl chloride, polyacrylates (polyethyl acrylate and polymethyl acrylate, polymethyl methacrylate, polymethylcoethyl acrylate, ethylene/ethyl acrylate), polycarbonate urethane (BIONATE®), polysiloxanes (silicones), polytetrafluoroethylene (PTFE, GORE-TEX®, ethylene/chlorotrifluoroethylene copolymer, aliphatic polyesters, ethylene/tetrafluoroethylene copolymer), polyketones (polyaryletheretherketone, polyetheretherketone, polyetherether-ketoneketone, polyetherketoneetherketoneketone polyetherketone), polyether block amides (PEBAX®, PEBA), polyamides (polyamideimide, PA-11, PA-12, PA-46, PA-66), polyetherimide, polyether sulfone, poly(iso)butylene, polyvinyl chloride, polyvinyl fluoride, polyvinyl alcohol, polyurethane, polybutylene terephthalate, polyphosphazenes, nylon, polypropylene, polybutester, nylon and polyester, polymer foams (from carbonates, styrene, for example) as well as the copolymers and blends of the classes listed and/or the class of thermoplastics and elastomers/thermoplastic elastomers in general.

Pneumostoma management devices may be made of a suitable biocompatible plastic/thermoplastic/thermoplastic elastomer. For example in one preferred embodiment the tube is made of PEBAX® a block copolymer with suitable mechanical and chemical properties available from Arkema (Colombes, France). Another suitable material is C-FLEX® thermoplastic elastomer available as extruded tube in a variety of dimensions and durometers from Saint-Gobain Performance Plastics in Clearwater, Fla. Reference to appropriate polymers that can be used for manufacturing PMDs can be found, for example, in the following documents: PCT Publication WO 02/02158, entitled "Bio-Compatible Polymeric Materials;" PCT Publication WO 02/00275, entitled "Bio-Compatible Polymeric Materials;" and, PCT Publication WO 02/00270, entitled "Bio-Compatible Polymeric Materials" all of which are incorporated herein by reference. Other suitable materials for the manufacture of the PMD include medical grade inorganic materials such stainless steel, titanium, ceramics and coated materials.

Additionally, the tube of a pneumostoma vent may be treated and/or coated on the exterior surface to facilitate installation. The tube may be treated and/or coated to make the tube smoother and/or more lubricious to reduce resistance to installation of the vent tube in the pneumostoma. The polymer of the tube may also be treated and/or coated to make the surface hydrophilic thereby attracting water molecules as a lubricant. If a coating is used it should be selected so as to be biocompatible and not cause irritation of the pneumostoma. Lubricious coatings include, for example hydrophilic, TEFLON®, and Parylene/Paralyne films/coatings. A lubricious coating may also include a therapeutic agent (see below).

Additionally, the tube of a pneumostoma vent may be designed to deliver a pharmaceutically-active substance. For purposes of the present disclosure, a "pharmaceutically-active substance" is an active ingredient of vegetable, animal or synthetic origin which is used in a suitable dosage as a therapeutic agent for influencing conditions or functions of the body, as a replacement for active ingredients naturally produced by the human or animal body and to eliminate or neutralize disease pathogens or exogenous substances. The release of the substance in the environment of pneumostoma vent has an effect on the course of healing and/or counteracts pathological changes in the tissue due to the presence of the pneumostoma vent. In particular, it is desirable in some embodiments to coat or impregnate pneumostoma vent with pharmaceutically-active substances that preserve the patency of pneumostoma and/or are antimicrobial in nature but that do not unduly irritate the tissues of the pneumostoma. However, the pneumostoma vent may also deliver, be coated with or be impregnated with time-release therapeutic agents designed to have effects on tissues other than the tissues of the pneumostoma.

In particular cases, suitable pharmaceutically-active substances may have an anti-inflammatory and/or antiproliferative and/or spasmolytic and/or endothelium-forming effect, so that the functionality of the pneumostoma is maintained. Suitable pharmaceutically-active substances include: anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); anti-platelet agents such as G(GP) llb/llla inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6a-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (inaperturethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); silver & silver compounds (e.g. nano-silver, colloidal silver) immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); silver compound and protease inhibitors.

In some embodiments, the active pharmaceutical substance to be coated upon or impregnated in the pneumostoma vent is selected from the group consisting of amino acids, anabolics, analgesics and antagonists, anaesthetics, anti-adrenergic agents, anti-asthmatics, anti-atherosclerotics, antibacterials, anticholesterolics, anti-coagulants, antidepressants, antidotes, anti-emetics, anti-epileptic drugs, antifibrinolytics, anti-inflammatory agents, antihypertensives, antimetabolites, antimigraine agents, antimycotics, antinauseants, antineoplastics, anti-obesity agents, antiprotozoals, antipsychotics, antirheumatics, antiseptics, antivertigo agents, antivirals, appetite stimulants, bacterial vaccines, bioflavonoids, calcium channel blockers, capillary stabilizing agents, coagulants, corticosteroids, detoxifying agents for cytostatic treatment, diagnostic agents (like contrast media, radiopaque agents and radioisotopes), electrolytes, enzymes, enzyme inhibitors, ferments, ferment inhibitors, gangliosides and ganglioside derivatives, hemostatics, hormones, hormone antagonists, hypnotics, immunomodulators, immunostimulants, immunosuppressants, minerals, muscle relaxants, neuromodulators, neurotransmitters and neurotrophins, osmotic diuretics, parasympatholytics, para-sympathomimetics, peptides, proteins, psychostimulants, respiratory stimulants, sedatives, serum lipid reducing agents, smooth muscle relaxants, sympatholytics, sympathomimetics, vasodilators, vasoprotectives, vectors for gene therapy, viral vaccines, viruses, vitamins, oligonucleotides and derivatives, saccharides, polysaccharides, glycoproteins, hyaluronic acid, and any excipient that can be used to stabilize a proteinaceous therapeutic Hydrophobic filter materials for pneumostoma vents should be sufficiently porous to allow air to exit through the filter. In order to facilitate air flow through the filter a filter material with low to extremely low resistance to air flow is preferred consistent with the structural and size requirements for the filter. Materials for hydrophobic filters are available commercially and filters can be fabricated from any suitable hydrophobic polymer, such as tetrafluoroethylene, PTFE, polyolefins, microglass, polyethylene and polypropylene or a mixture thereof. In preferred examples, the hydrophobic filter is a laminated tetrafluoroethylene e.g. TEFLON®, (E.I. du Pont de Nemours Co.) or GORE-TEX® (W.L. Gore, Inc.) of a controlled pore size. In other examples the hydrophobic filter may comprise a felted polypropylene; PTFE/polypropylene filter media or a reticulated polyurethane-based open cell foam. In a preferred embodiment, the filter is an open cell polyurethane or polyester foam or melt blown polyethylene. Exemplary filter materials include DELPORE® DP2001-10P, DELPORE® DP2001-20P, and DELPORE® DP2001-30P available from Delstar Technologies, Inc. (Middletown, Del.). A filter may additionally comprise an antimicrobial, an anti-bacterial, and/or an anti-viral material or agent, for example silver.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

The invention claimed is:

1. A pneumostoma management device adapted to allow gases to exit parenchymal tissue of a lung through a pneumostoma in a chest of a patient, wherein the pneumostoma management device comprises:
   an extruded tube having a first length and adapted to be cut to a second selected length sufficient to pass into the parenchymal tissue of the lung through the pneumostoma,
   the extruded tube having a lumen, a proximal end and a distal end,
   the distal end of the extruded tube having at least one opening adapted to admit gases from the parenchymal tissue of the lung;
   a flange connected to the proximal end of the extruded tube such that an opening in the flange communicates with the lumen of the extruded tube,
   the flange projecting a sufficient distance from the extruded tube to preclude passage of the flange into the pneumostoma, and
   a filter disposed over the opening in the flange and secured to one of the flange and the extruded tube such that gases passing through the lumen of the tube passes through the filter.

2. The pneumostoma management device of claim 1, wherein the tube is connected substantially centrally to the flange.

3. The pneumostoma management device of claim 1, wherein the distal end of the tube is rounded over to provide an atraumatic tip.

4. The pneumostoma management device of claim 1, wherein the flange is made from the proximal end of the tube by heating the proximal end of the tube and deforming it to create the flange.

5. The pneumostoma management device of claim 1, further comprises one or more apertures in a wall of the tube proximate to the distal end of the tube and adapted to admit gases from the pneumostoma.

6. The pneumostoma management device of claim 1 further comprising:
   a flexible patch for securing the pneumostoma management device to the chest of the patient;
   wherein the patch is larger in area than the flange; and
   wherein the patch has an aperture therethrough the aperture being larger than the diameter of the tube and smaller than the diameter of the flange such that the tube may be passed through the aperture and the flange may be secured to the patch.

7. The pneumostoma management device of claim 1 further comprising:
   a flexible patch for securing the pneumostoma management device to the chest of the patient;
   wherein the patch is larger in area than the flange;
   wherein the patch has an aperture therethrough the aperture being larger than the diameter of the tube and smaller than the diameter of the flange such that the tube may be passed through the aperture and the flange may be secured to the patch; and
   wherein the patch comprises a hydrocolloid adhesive for adhering the patch to the chest of the patient.

8. The pneumostoma management device of claim 1, wherein the filter is substantially flush with the flange.

9. The pneumostoma management device of claim 1, wherein the flange, filter and adhesive coating is less than 5 mm in thickness in combination.

10. A medical device for venting gases from parenchymal tissue of a lung of a patient through a stoma formed between skin of the patient and a lung of the patient, wherein the medical device comprises:
- an extruded tube having a first length and adapted to be cut to a second selected length sufficient to pass into the parenchymal tissue of the lung through the chest wall,
  the extruded tube having a lumen, a proximal end and a distal end,
  the distal end of the extruded tube having at least one opening adapted to admit gases from the parenchymal tissue of the lung into the lumen;
- a flange projecting radially from the proximal end of the extruded tube;
  the flange having an opening which communicates with the lumen of the extruded tube; and
- a filter secured over the opening in the flange such that gases in the lumen of the tube exit the lumen of the tube by passing through the filter.

11. The medical device of claim 10, wherein the tube is an extruded thermoplastic elastomer tube.

12. The medical device of claim 10, wherein the tube is an extruded tube and wherein the flange is made from the proximal end of the extruded tube by heating the proximal end of the tube and deforming it to create the flange.

13. The medical device of claim 10, wherein the tube is an extruded tube and wherein the distal end of the tube is rounded over to provide an atraumatic tip.

14. The medical device of claim 10, wherein the tube is an extruded tube and wherein:
- the flange is made from the proximal end of the extruded tube by heating the proximal end of the tube and deforming it to create the flange;
- the distal end of the tube is rounded over to provide an atraumatic tip.

15. The medical device of claim 10, further comprising one or more side openings in the tube adjacent the distal end of the tube and adapted to admit gases from the lung.

16. The medical device of claim 10 further comprising a thin flexible adhesive patch attached to the flange and adapted to secure the medical device to the chest of the patient.

17. The medical device of claim 10 further comprising a hydrocolloid patch attached to the flange and adapted to secure the medical device to the chest of the patient.

18. The medical device of claim 10, wherein the filter is substantially flush with the flange.

19. A medical device for venting gases from parenchymal tissue of a lung of a patient through a stoma formed between the skin of the patient and the lung of the patient, wherein the medical device comprises:
- an extruded tube having a first length and adapted to be cut to a second selected length sufficient to pass into the parenchymal tissue of the lung through the chest wall,
  the extruded tube having a lumen, a proximal end and a distal end,
  the distal end of the extruded tube having at least one opening adapted to admit gases from the parenchymal tissue of the lung into the lumen;
- a flange projecting radially from the proximal end of the extruded tube and adapted to prevent the distal end of the medical device from passing into the stoma;
  the flange having an opening which communicates with the lumen of the extruded tube; and
- a hydrophobic filter secured over the opening in the flange such that gases in the lumen of the tube exit the lumen of the tube by passing through the filter.

* * * * *